(12) United States Patent
Montagne et al.

(10) Patent No.: US 8,889,668 B2
(45) Date of Patent: Nov. 18, 2014

(54) OXADIAZOLE DIARYL COMPOUNDS

(71) Applicant: Merck Serono SA, Vaud (CH)

(72) Inventors: Cyril Montagne, Saint-Genis-Pouilly (FR); Anna Quattropani, Geneva (CH); Wolfgang Sauer, Chambesy (CH); Agnes Bombrun, Chambesy (CH)

(73) Assignee: Merck Serono SA, Coinsins, Vaud (CH)

( * ) Notice: Subject to any disclaimer, the term of this patent is extended or adjusted under 35 U.S.C. 154(b) by 28 days.

(21) Appl. No.: 13/711,934

(22) Filed: Dec. 12, 2012

(65) Prior Publication Data

US 2013/0109676 A1   May 2, 2013

Related U.S. Application Data

(63) Continuation of application No. 12/675,254, filed as application No. PCT/EP2008/063185 on Oct. 1, 2008, now Pat. No. 8,404,676.

(60) Provisional application No. 60/998,136, filed on Oct. 9, 2007.

(30) Foreign Application Priority Data

Oct. 4, 2007   (EP) .................................... 07117925

(51) Int. Cl.
| | | |
|---|---|---|
| C07D 413/10 | (2006.01) | |
| A61K 31/454 | (2006.01) | |
| A61K 31/5377 | (2006.01) | |
| C07D 271/06 | (2006.01) | |
| A61K 31/4245 | (2006.01) | |
| A61K 31/55 | (2006.01) | |
| C07D 413/14 | (2006.01) | |
| A61K 45/06 | (2006.01) | |
| C07D 271/07 | (2006.01) | |

(52) U.S. Cl.
CPC .......... *C07D 413/10* (2013.01); *A61K 31/5377* (2013.01); *A61K 31/454* (2013.01); *C07D 413/14* (2013.01); *A61K 45/06* (2013.01); *A61K 31/4245* (2013.01); *A61K 31/55* (2013.01); *C07D 271/06* (2013.01); *C07D 271/07* (2013.01)
USPC ...................... 514/217.1; 546/209; 546/269.1; 546/256; 544/138; 548/131; 540/603; 514/326; 514/236.2; 514/364; 514/340; 514/333

(58) Field of Classification Search
None
See application file for complete search history.

(56) References Cited

U.S. PATENT DOCUMENTS

| 4,135,910 A | 1/1979 | Howe |
| 6,277,872 B1 * | 8/2001 | Brenner et al. ............... 514/364 |
| 8,202,865 B2 | 6/2012 | Quattropani et al. |
| 2008/0200535 A1 | 8/2008 | Ohmori et al. |

FOREIGN PATENT DOCUMENTS

| DE | 4320801 | 1/1995 |
| GB | 1 584 716 | 2/1981 |
| WO | WO 00/64927 | 11/2000 |
| WO | WO 2004/091502 | 10/2004 |
| WO | WO 2005/032465 | 4/2005 |
| WO | WO 2005/058848 | 6/2005 |
| WO | WO 2005/115382 | 12/2005 |
| WO | WO 2006/131336 | 12/2006 |
| WO | WO 2007/043400 | 4/2007 |
| WO | WO 2008/023783 | 2/2008 |
| WO | WO 2008/037476 | 4/2008 |
| WO | WO 2008/076356 | 6/2008 |
| WO | WO 2008/152149 | 12/2008 |
| WO | WO 2009/043889 | 4/2009 |

OTHER PUBLICATIONS

Kappos et al. in New England Journal of Medicine 355:1124-1140 (2006).*
Gold et al. in Brain 129, 1953-1971(2006).*
Rosen, H. et al. "Tipping the gatekeeper: S1P regulation of endothelial barrier function" *Trends in Immunology*, 2007, pp. 102-107, vol. 28, No. 3.
Yoshida, M. et al. "Study of biodegradable copoly (L-lactic acid/glycolic acid) formulations with controlled release of Z-100 for application in radiation therapy" *International Journal of Pharmaceutics*, 1995, pp. 61-67, vol. 115.
Cyster, J. G. "Chemokines, Sphingosine-1-Phosphate, and Cell Migration in Secondary Lymphoid Organs" *Ann. Rev. Immunol.*, 2005, pp. 127-159, vol. 23.
Rosen, H. et al. "Sphingosine 1-Phosphate and its Receptors: An Autocrine and Paracrine Network" *Nature*, Jul. 2005, pp. 560-570, vol. 5.

(Continued)

Primary Examiner — Dennis Heyer
(74) Attorney, Agent, or Firm — Saliwanchik, Lloyd & Eisenschenk

(57) ABSTRACT

The invention relates to compounds of formula (I):

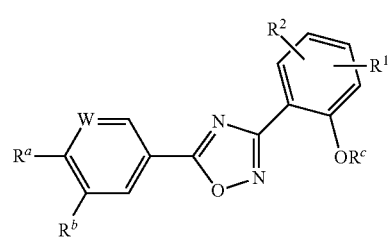

wherein $R^1$, $R^2$, $R^a$, $R^b$, $R^c$ and W, have the meanings given in claim 1. The compounds are useful e.g. in the treatment of autoimmune disorders, such as multiple sclerosis.

12 Claims, No Drawings

(56) References Cited

OTHER PUBLICATIONS

Kappos, L. et al. "Oral Fingolimod (FTY720) for Relapsing Multiple Sclerosis" *N. Eng. J. Med.*, Sep. 14, 2006, pp. 1124-1140, vol. 355.
Massberg, S. et al. "Fingolimod and Sphingosine-1-Phosphate-Modifiers of Lympho-cyte Migration" *N. Eng. J. Med.*, Sep. 14, 2006, pp. 1088-1091, vol. 355, No. 2.
Yopp, A. C. et al. "Sphingosine 1-phosphate receptor modulators: a new class of immunosuppressants" *Clin Transplant*, 2006, pp. 788-795, vol. 20.
Tyle, P. "Iontophoretic Devices for Drug Delivery" *Pharmaceutical Research*, 1986, pp. 318-326, vol. 3, No. 6.
Database CHEMCATS, Accession No. 2028111707, Oxadiazole, Oct. 5, 2007, XP-002466530, p. 1.
Database CHEMCATS, Accession No. 2038041362, Piperazine, Sep. 6, 2007, XP-002466528, pp. 1-3.
Database CHEMCATS, Accession No. 2039084421, 1, 2, 4-Oxadiazole, Oct. 2, 2007, XP-002466529, p. 1.
Bulgarevich, S.B. et al. "Molecular Polarizability of Organic Compounds and Their Complexes. Part XIV.*Kerr Constants and Dipole Moments of Products of the Reaction of 4-Oxo-1,3-Benzoxazinium Salts with Hydroxylamine and Methylhydrazine" *Scientific Research Institute of Physical and Organic Chemistry*, Rostov-on-Don, Sep. 29, 1980, pp. 1418-1422.
Written Opinion in International Application No. PCT/EP2008/063185, Feb. 9, 2009, pp. 1-7.
Cho, S. Y. et al. "Protein Tyrosine Phosphatase 1B Inhibitors: Heterocyclic Carboxylic Acids" *Bull. Korean Chem. Soc.*, 2003, pp. 1455-1464, vol. 24, No. 10, XP-002467994.
Yan, L. et al. "Discovery of 3-arylpropionic acids as potent agonists of sphingosine-1-phosphate receptor-1 ($S1P_1$) with high selectivity against all other known S1P receptor subtypes" *Bioorganic & Medicinal Chemistry Letters*, 2006, pp. 3679-3683, vol. 16, XP-005477311.
Database Registry Chemical Abstracts Service, Columbus, Ohio, Accession No. RN 937669-94-8, Jun. 17, 2007, p. 1, XP-002467995.
Database Registry Chemical Abstracts Service, Columbus, Ohio, Accession No. RN 937669-95-9, Jun. 17, 2007, p. 1, XP-002467996.
Database Registry Chemical Abstracts Service, Columbus, Ohio, Accession No. RN 937670-06-9, Jun. 17, 2007, p. 1, XP-002467997.
Database Registry Chemical Abstracts Service, Columbus, Ohio, Accession No. RN 937681-49-7, Jun. 17, 2007, p. 1, XP-002467998.
Database Registry Chemical Abstracts Service, Columbus, Ohio, Accession No. RN 937697-96-6, Jun. 17, 2007, p. 1, XP-002467999.
Database Registry Chemical Abstracts Service, Columbus, Ohio, Accession No. RN 937681-63-5, Jun. 17, 2007, p. 1, XP-002468000.
Database Registry Chemical Abstracts Service, Columbus, Ohio, Accession No. RN 937681-77-1, Jun. 17, 2007, p. 1, XP-002468001.
Database Chemcats Chemical Abstracts Service, Columbus, Ohio, Accession No. 2037051069, Aug. 13, 2007, p. 1, XP-002468003.
Database Registry Chemical Abstracts Service, Columbus, Ohio, Accession No. RN 894518-34-4, Jul. 19, 2006, p. 1, XP-002531330.
Database Registry Chemical Abstracts Service, Columbus, Ohio, Accession No. RN 832683-65-5, Feb. 17, 2005, p. 1, XP-002531331.
Written Opinion in International Application No. PCT/EP2008/063180, Jun. 10, 2009, pp. 1-13.
Database Registry Chemical Abstract Service, Columbus, Ohio, Accession No. RN 937669-94-8 (Apr. 23, 2007), p. 1.
Ito, N. et al. "A medium-term rat liver bioassay for rapid in vivo detection of carcinogenic potential of chemicals" *Cancer Sci.*, Jan. 2003, pp. 3-8, vol. 94, No. 1.

\* cited by examiner

OXADIAZOLE DIARYL COMPOUNDS

CROSS-REFERENCE TO RELATED APPLICATIONS

This application is a continuation of U.S. Ser. No. 12/675,254, filed Feb. 25, 2010 which is the U.S. national stage application of International Patent Application No. PCT/EP2008/063185, filed Oct. 1, 2008, which claims the benefit of U.S. Provisional Patent Application No. 60/998,136, filed Oct. 9, 2007, the disclosures of which are hereby incorporated by reference in their entirety, including all figures, tables and amino acid or nucleic acid sequences.

The present invention relates to oxadiazole diaryl compounds, their use as medicaments and their use for treating multiple sclerosis and other diseases.

In particular, the invention relates to compounds of formula (I):

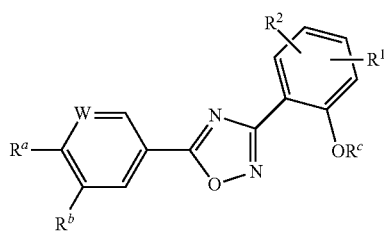

wherein $R^1$, $R^2$ denote H, Hal, $CF_3$, $OCF_3$, CN, or $NO_2$,

W denotes CH or N, $R^a$ is Ar, Het, cycloalkyl having 3-7 atoms, A or $NA_2$, $R^b$ is H, A, Hal, $CF_3$, $OCF_3$, $OR^3$, CN, $NO_2$, $(CH_2)_nN(R^3)_2$, OA, especially $OCH_3$, $(CH_2)_nSO_2N(R^3)_2$, $(CH_2)_nNR^3SO_2A$, $(CH_2)_nN(SO_2A)_2$, $NR^3CON(R^3)_2$, $NR^3COA$ or $(CH_2)_nSO_2R^3$, $R^c$ denotes A, COA, CSA, COOA, CSOA, $CON(R^3)_2$ or $CSN(R^3)_2$ A is branched or linear alkyl having 1 to 12 C-atoms, wherein one or more, preferably all H-atoms may be replaced by Hal, especially F, or 1 to 7H-atoms may be replaced by $OR^3$, CN or $N(R^3)_2$ and wherein one or more, preferably 1 to 7 non adjacent $CH_2$-groups may be replaced by O, $NR^3$ or S and/or by —CH═CH— or —C≡C-groups, or denotes cycloalkyl or cycloalkylkylen having 3-7 ring C atoms Hal is F, Cl, Br or I, Ar denotes a monocyclic or bicyclic, unsaturated or aromatic carbocyclic ring having 6 to 14 carbon atoms which may be unsubstituted or monosubstituted, disubstituted or trisubstituted by Hal, A, $CH_2OA$, $CH_2N(R^3)_2$, $OR^3$, $N(R^3)_2$, $NO_2$, $N(SO_2Me)_2$, CN, $COOR^3$, $CF_3$, $OCF_3$, $CON(R^3)_2$, $NR^3COA$, $NR^3CON(R^3)_2$, $NR^3SO_2A$, $COR^3$, $SO_2N(R^3)_2$, SOA or $SO_2A$, phenyl, pyridyl —$[C(R^3)_2]_n$—$COOR^3$ and/or —$O[C(R^3)_2]_n$—$CON(R^3)_2$, Het denotes a monocyclic or bicyclic, saturated, unsaturated or aromatic heterocyclic ring having 1 N and/or 1 to 3 O and/or S atoms which may be unsubstituted or monosubstituted, disubstituted or trisubstituted by Hal, A, —$[C(R^3)_2]_n$—Ar, —$[C(R^3)_2]_n$-cycloalkyl, $CH_2OA$, $CH_2N(R^3)_2$, $OR^3$, $CF_3$, $OCF_3$, $N(R^3)_2$, $N(SO_2Me)_2$, $NR^3CON(R^3)_2$, $NO_2$, CN, —$[C(R^3)_2]_n$—$COOR^3$, —$[C(R^3)_2]_n$—$CON(R^3)_2$, $NR^3COA$, $NR^3SO_2A$, $COR^3$, $SO_2N(R^3)_2$, SOA, phenyl, pyridyl and/or $SO_2A$, $R^3$ is H or A and n is 0, 1, 2, 3, 4, 5, 6, 7 or 8, and pharmaceutically acceptable derivatives, solvates, tautomers, salts and stereoisomers thereof, including mixtures thereof in all ratios.

The compounds of formula (I) are preferably binding on receptors for sphingosine 1-phosphate (S1P). S1P is a bioactive sphingolipid metabolite that is secreted by hematopoietic cells and stored and released from activated platelets. It acts as an agonist on a family of G protein-coupled receptors (GPCR). Five sphingosine 1-phosphate receptors have been identified ($S1P_1$, $S1P_2$, $S1P_3$, $S1P_4$, and $S1P_5$, also known as endothelial differentiation genes, which are Edg1, Edg5, Edg3, Edg6 and Edg8 respectively), that have widespread cellular and tissue distribution and are well conserved in human and rodent species.

S1P is involved in a number of cellular functions such as survival, proliferation and immunological responses. The compounds of the present invention are preferably acting as $S1P_1$/Edg1 receptor agonists and thus have immunosuppressive activities by modulating leukocyte trafficking, sequestering lymphocytes in secondary lymphoid tissues, and interfering with cell-cell interactions required for an efficient immune response. The invention is also directed to pharmaceutical compositions containing such compounds and methods of treatment or prevention.

FTY720 or fingolimod, a non selective $S1P_1$ agonist, exerts immunosuppressive activity and shows therapeutic effects in the treatment of relapsing-remitting multiple sclerosis. Numerous publications have been already published using this compound: Cyster J G Annu Rev Immunol 23:127-59, 2005, Rosen H Nat Rev Immunol 5:560-570, 2005, Rosen H Trends Immunol 28:102-107, 2007, Yopp A C Clin Transplant 20:788-795, 2006, Kappos L N Engl J Med 355:1124-1140, 2006, Massberg S N Engl J Med 355:1088-1089, 2006.

Immunosuppressive agents are further useful in a wide variety of autoimmune and chronic inflammatory diseases, including systemic lupus erythematosus, chronic rheumatoid arthritis, type I diabetes mellitus, inflammatory bowel diseases, biliary cirrhosis, uveitis and other disorders such as Crohn's diseases, ulcerative colitis, bullous pemphigoid, sarcoidosis, psoriasis, autoimmune myositis, Wegener's granulomatosis, ichthyosis, Graves ophthalmopathy, atopic dermatitis and asthma. They are also useful as part of chemotherapeutic regimens for the treatment of cancers, lymphomas and leukemias.

It has been found that the compounds of the present invention are selective $S1P_1$ agonists with improved pharmacological and/or other properties.

The present invention uses compounds of Formula (I) and pharmaceutically usable derivatives, salts, tautomers, solvates and stereoisomers thereof, including mixtures thereof in all ratios, for the preparation of a medicament for the treatment and/or prophylaxis of diseases in which the inhibition, activation, regulation, and/or modulation of $S1P_1$ receptor signal transduction plays a role.

Thus, the present invention preferably comprises compounds which are agonists of the $S1P_1$/Edg1 receptor, especially having selectivity over the $S1P_3$/Edg3 receptor. An $S1P_1$/Edg1 receptor selective agonist has advantages over current therapies and extends the therapeutic window of lymphocyte sequestration agents, allowing better tolerability with higher dosing and thus improving efficacy.

The invention further relates to the manufacture of a medicament for the improvement of vascular function, either alone or in combination with other active compounds or therapies.

The oxadiazole diaryl compounds according to Formula (I) may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The following abbreviations refer respectively to the definitions below:

aq. (aqueous), h (hour), g (gram), L (liter), mg (milligram), MHz (Megahertz), µM (micromolar) min. (minute), mm (millimeter), mmol (millimole), mM (millimolar), m.p. (melting point), eq. (equivalent), mL (milliliter), µL (microliter), ACN (acetonitrile), BINAP (2,2'-bis(disphenylphosphino)-1,1'-binaphthalene, BOC (tert-butoxy-carbonyl), CBZ (carbobenzoxy), CDCl$_3$ (deuterated chloroform), CD$_3$OD (deuterated methanol), CH$_3$CN (acetonitrile), conc. (concentrated), c-hex (cyclohexane), DCC (dicyclohexyl carbodiimide), DCE (dichloroethane), DCM (dichloromethane), DIC (diisopropyl carbodiimide), DIEA (diisopropylethyl-amine), DMF (dimethylformamide), DMSO (dimethylsulfoxide), DMSO-d$_6$ (deuterated dimethylsulfoxide), EDC (1-(3-dimethyl-amino-propyl)-3-ethylcarbodiimide), ESI (Electro-spray ionization), Ethyl acetate (ethyl acetate), Et$_2$O (diethyl ether), EtOH (ethanol), FMOC (fluorenylmethyloxycarbonyl), HATU (dimethylamino-([1,2,3] triazolo[4,5-b]pyridin-3-yloxy)-methylene]-dimethyl-ammonium hexafluorophosphate), HPLC (High Performance Liquid Chromatography), i-PrOH (2-propanol), K$_2$CO$_3$ (potassium carbonate), LC (Liquid Chromatography), MeOH (methanol), MgSO$_4$ (magnesium sulfate), MS (mass spectrometry), MTBE (Methyl tert-butyl ether), Mtr. (4-Methoxy-2,3,6-trimethylbenzensulfonyl), MW (microwave), NaHCO$_3$ (sodium bicarbonate), NaBH$_4$ (sodium borohydride), NMM (N-methyl morpholine), NMR (Nuclear Magnetic Resonance), Pd(PPh$_3$)$_4$ (tetrakis(triphenylphosphine) palladium), POA (phenoxyacetate), PyBOP® (benzotriazole-1-yl-oxy-tris-pyrrolidino-phosphonium hexafluorophosphate), RT (room temperature), Rt (retention time), sat. (saturated), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

Depending on the nature of R$^a$, R$^b$, R$^c$, R$^1$, R$^2$ and W different synthetic strategies may be selected for the synthesis of compounds of Formula (I). In the process illustrated in the following schemes R$^a$, R$^b$, R$^c$, R$^1$, R$^2$ and W are as above-defined in the description.

In general, the oxadiazole diaryl compounds according to Formula (I) of this invention may be prepared from readily available starting materials. If such starting materials are not commercially available they may be prepared by standard synthetic techniques. The following general methods and procedures described hereinafter in the examples may be employed to prepare compounds of Formula (I).

Generally, compounds of Formula (I) can be prepared by coupling an aryl amidoxime of Formula (III) and an aryl carboxylic acid of Formula (IV) (or an activated derivative thereof, such as formula II) and by dehydrating the resulting intermediate, wherein R$^a$, R$^b$, R$^c$, R$^1$, R$^2$ and W are defined as above, as outlined in Scheme 1. General protocols for such couplings and dehydrations are given below in the Examples, using conditions and methods well known to those skilled in the art to prepare an oxadiazole from an aryl carboxylic acid and an aryl amidoxime, by forming an acid derivative such as an acid chloride by reacting the carboxylic acid with oxalyl chloride, thionyl chloride or trichloroacetonitrile and a suitable phosphine (e.g. Polymer supported triphenyl phosphine) in the presence or absence of bases such as TEA, DIEA, NMM in a suitable solvent such as DCM, THF or DMF, at a temperature rising from 20° C. to 200° C., for a few hours, e.g. one hour to 24 h. The obtained acid chloride may be coupled to an amidoxime of Formula (III) and the resulting intermediate dehydrated in the presence or absence of bases such as TEA, DIEA, NMM or pyridine in a suitable solvent such as DCM, THF or toluene at a temperature rising from about 20° C. to about 200° C., preferably 150° C. for a time ranging from about 10 minutes to about 24 h, preferably 30 minutes. Alternatively, coupling agents, such as but not limited to polymer-supported 1-alkyl-2-chloropyridinium salt (polymer-supported Mukaiyama's reagent), 1-methyl-2-chloropyridinium iodide (Mukaiyama's reagent), EDC or HATU in the presence or absence of bases such as TEA, DIEA, NMM in a suitable solvent such as DCM, THF or DMF, at a temperature rising from about 20° C. to about 50° C., preferably at room temperature, for a few hours, e.g. one hour to 24 h, may be used.

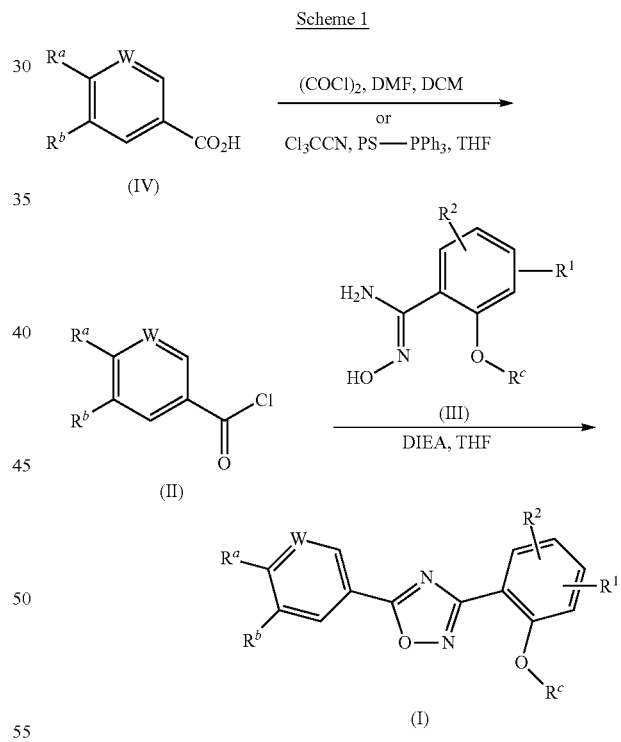

Scheme 1

Compounds of Formula (Ia) can be obtained from Compounds of Formula (Ib) as outlined in Scheme 2 by the reduction of the nitro to an amine, using hydrogen (which can be generated in situ from ammonium formate or formic acid) in the presence of a metal catalyst such as Pd/C or Raney nickel, or using reducing agents such as iron or tin(II) chloride, or using metal hydrides such as lithium aluminium hydride, in a suitable solvent such as a lower alcohol, water, THF, dioxane or ether, or a mixture thereof, at a temperature ranging from about −100° C. to about 100° C., preferably from 0° C. to 80° C., for a few hours.

Scheme 2

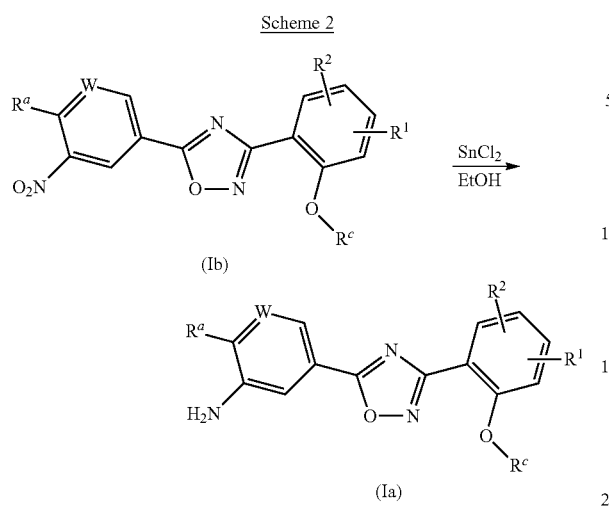

Compounds of Formula (Ic) and/or (Id), can be obtained from compounds of Formula (Ie) as outlined in Scheme 3, by sulfonylation of the amino group, using alkylsulfonylchlorides. This reaction can be done in the absence or the presence of a base such as TEA, DIEA or pyridine, in a suitable solvent such as DCM, DCE, THF, dioxane, DMF or DMA or a mixture thereof. This reaction is preferably performed at a temperature ranging from about 0° C. to about 100° C., preferably from 0° C. to 40° C., for a few hours.

Scheme 3

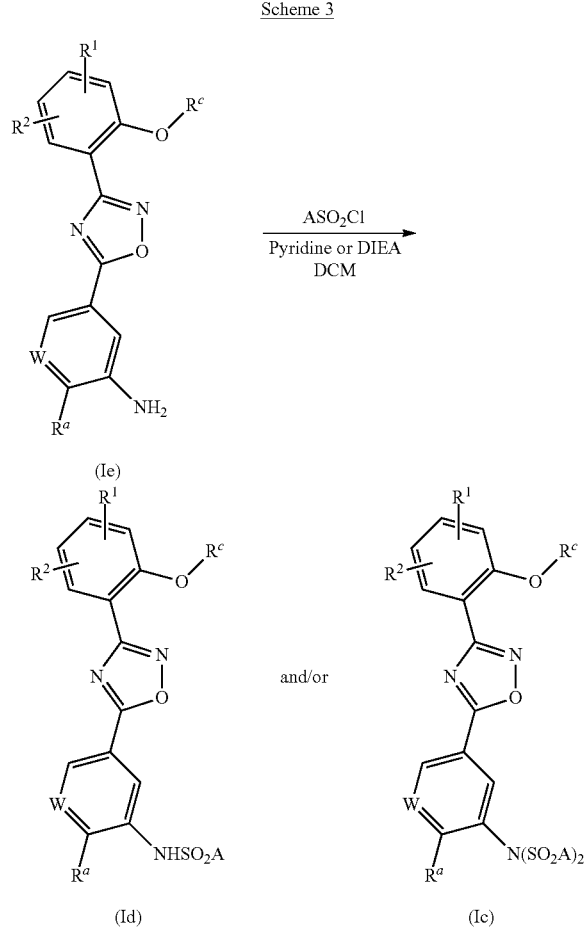

Compounds of Formula (If) can be obtained from compounds of Formula (Ih) as outlined in Scheme 4 by transforming the hydroxyl moiety into a leaving group such as, but not limited to, alkyl- or aryl-sulfonates or halogens (preferably Cl, Br and I). The obtained intermediate (Ig) is then reacted with an amine of Formula $HN(R^3)_2$ in the absence or the presence of a base such as TEA, DIEA or pyridine, in a suitable solvent such as DCM, DCE, THF, dioxane DMF or DMA or a mixture thereof. This reaction is preferably performed at a temperature ranging from about 0° C. to about 100° C., preferably from 0° C. to 40° C., for a few hours, preferably from 1 to 5 hours.

Scheme 4

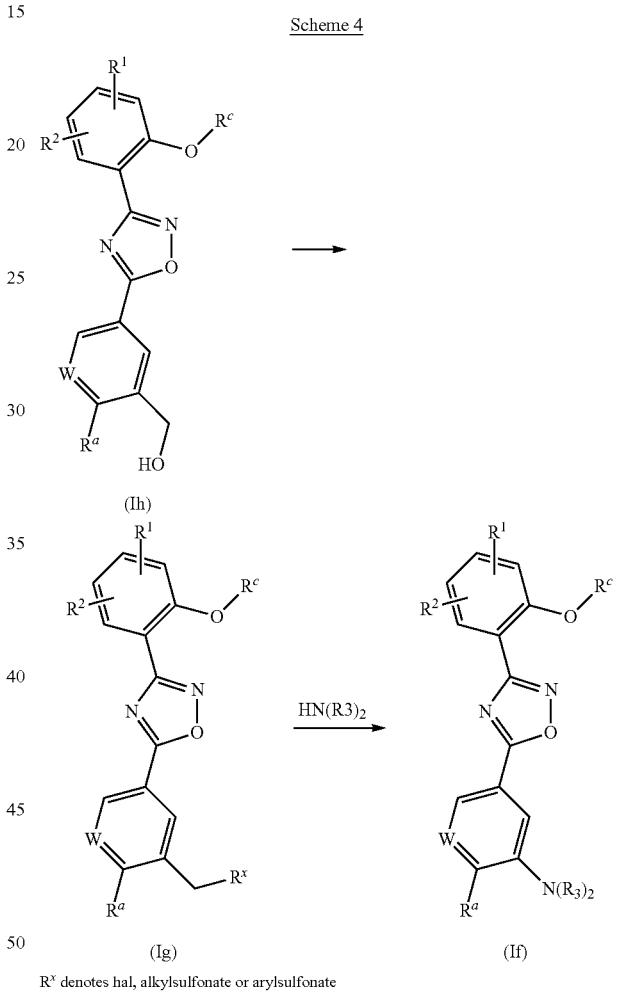

$R^x$ denotes hal, alkylsulfonate or arylsulfonate

Compounds of Formula (Ii) can be obtained from compounds of Formula (Ih) by one step oxidation using reagents such as $KMnO_4$ or $K_2Cr_2O_7$. Compounds of Formula (II) can also be obtained by a two-step procedure as outlined in scheme 5. The first step is the transformation of the —$CH_2OH$ moiety into an aldehyde (—CHO) using conventional conditions such as, but not limited to, $MnO_2$ or Swern oxidation. The second step consists in reacting the intermediate (Ij) with an oxidant such as sodium chlorite. This reaction can be performed in the presence or the absence of a base such as sodium dihydrogenphosphate, in a suitable solvent such as water, THF, dioxane or a mixture thereof. This reaction is preferably performed at a temperature ranging from about −20° C. to about 60° C., preferably from 0° C. to 40° C., for a few hours, preferably from 10 to 40 hours.

Scheme 5

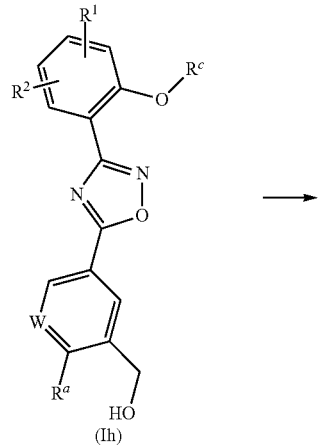

The compounds of Formula (III), wherein $R^1$, $R^2$ and $R^c$ are defined as above, can be obtained as outlined in Scheme 6 by reacting a commercially available aryl nitrile derivative with hydroxylamine in a suitable solvent such as water, MeOH, EtOH or a mixture thereof, preferably EtOH at a temperature ranging from about 20° C. to about 100° C., preferably 20° C. to 60° C. for a few hours.

Scheme 6

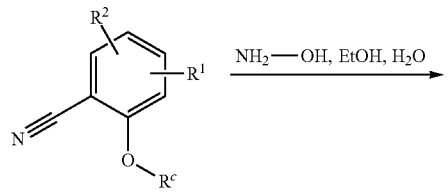

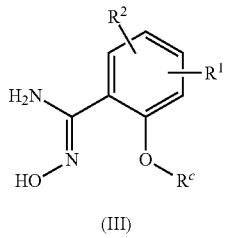

The method for preparing the compounds of Formula (III) selected below:
N'-hydroxy-2-methoxybenzenecarboximidamide
N'-hydroxy-2-(trifluoromethoxy)benzenecarboximidamide
2-ethoxy-N'-hydroxybenzenecarboximidamide
5-fluoro-N'-hydroxy-2-methoxybenzenecarboximidamide
is more particularly described in the Examples.

The compounds of Formula (IV), wherein $R^a$ and $R^b$ are defined as above, can be obtained as outlined in Scheme 7 when $R^a$ is a tertiary amino group. The first step consists of the reaction of a commercially available secondary amine ($R^a$—H) with a commercially available 4-fluorobenzoic ester derivative in the presence or absence of bases such as TEA, DIEA or NMM at a temperature ranging from about 20° C. to about 150° C., preferably at room temperature, for a few hours, e.g. one hour to 24 h in a suitable solvent such as DMF, EtOH. The resulting ester can then be hydrolysed to give compounds of Formula (IV) using conditions and methods well known to those skilled in the art, such as but not limited to the use of a metal hydroxide, e.g. lithium hydroxide, sodium hydroxide or potassium hydroxide, in a suitable solvent such as THF, methanol or water or mixtures thereof, at a temperature ranging from about 20° C. to about 50° C., preferably at room temperature, for a few hours, e.g. one hour to 24 h.

Scheme 7

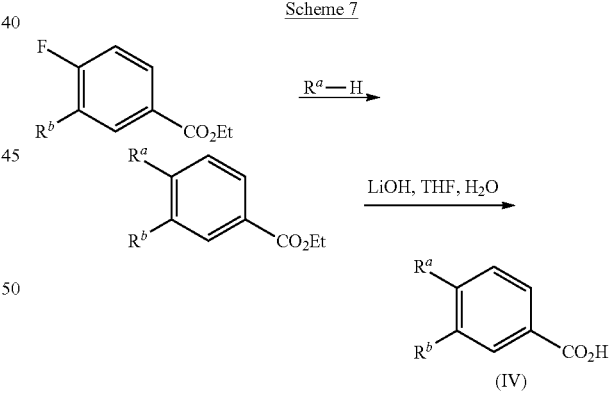

Alternatively, compounds of Formula (IV), wherein $R^a$ and $R^b$ are defined as above, can be obtained as outlined in Scheme 8 when $R^a$ is a tertiary amino group. The first step consists in the reaction of a commercially available secondary amine ($R^a$—H) with a commercially available 4-fluorobenzonitrile derivative in the presence or absence of bases such as TEA, DIEA or NMM at a temperature rising from about 20° C. to about 150° C., preferably at 60° C., for a few hours, preferably 8 h, neat or in a suitable solvent such as DMF, or EtOH. The resulting nitrile derivative can then be transformed into the corresponding ester derivative using conditions and methods well known to those skilled in the art, such as but not limited to the use of a mineral acid such as HCl in an alcohol such as MeOH, EtOH, preferably MeOH at a temperature rising from about 20° C. to about 100° C., preferably 60° C. for a few hours, preferably 24 h. The resulting ester can then be hydrolysed to give compounds of Formula (IV) by the use of a metal hydroxide, e.g. lithium hydroxide, sodium hydroxide or potassium hydroxide, in a suitable solvent such as THF, methanol or water or mixtures thereof, at a temperature rising from 20° C. to 50° C., preferably at room temperature, for a few hours, e.g. one hour to 24 h.

Scheme 8

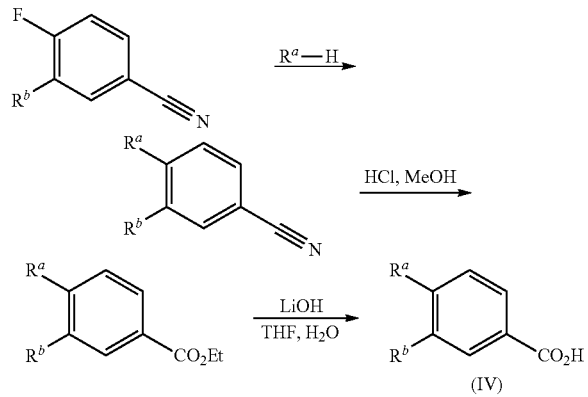

The compounds of Formula (IV), wherein $R^b$ is defined as above and wherein $R^a$ is a tertiary amino group, can be obtained as outlined in Scheme 9. The first step consists of the reaction of a commercially available secondary amine ($R^a$—H) with a 4-bromobenzoic ester derivative in the presence of a palladium source such as Pd(OAc)$_2$, a ligand such as BINAP and a base such as Cs$_2$CO$_3$, K$_2$CO$_3$, tBuOK, tBuONa, TEA, DIEA or NMM. The reaction is preferably performed at a temperature rising from about 20° C. to about 150° C., preferably between 80° C. and 120° C., for a few hours, e.g. one hour to 24 h in a suitable solvent such as DMF, EtOH or dioxane. The resulting ester can then be hydrolysed to give compounds of Formula (IV) using conditions and methods well known to those skilled in the art, such as but not limited to the use of a metal hydroxide, e.g. lithium hydroxide, sodium hydroxide or potassium hydroxide, in a suitable solvent such as THF, methanol or water or mixtures thereof, at a temperature ranging from about 20° C. to about 50° C., preferably at room temperature, for a few hours, e.g. one hour to 24 h.

Scheme 9

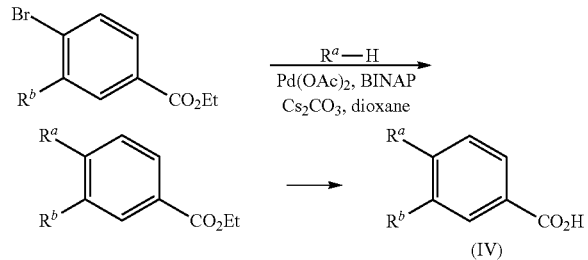

The method for preparing the compounds of Formula (IV) selected below:

3-nitro-4-piperidin-1-ylbenzoic acid
4-morpholin-4-yl-3-nitrobenzoic acid
4-piperidin-1-ylbenzoic acid
4-[cyclohexyl(methyl)amino]-3-nitrobenzoic acid
4-(2-methylpiperidin-1-yl)-3-nitrobenzoic acid
4-(3,3-difluoropiperidin-1-yl)-3-nitrobenzoic acid
3-nitro-4-pyrrolidin-1-ylbenzoic acid
4-azepan-1-yl-3-nitrobenzoic acid
4-(2-methylpiperidin-1-yl)-3-(trifluoromethyl)benzoic acid
4-(2,5-dimethylpyrrolidin-1-yl)-3-nitrobenzoic acid
4-[bis(2-methoxyethyl)amino]-3-nitrobenzoic acid
3-cyano-4-(2-methylpiperidin-1-yl)benzoic acid
6-(2-methylpiperidin-1-yl)nicotinic acid
5-methyl-6-(2-methylpiperidin-1-yl)nicotinic acid
6-[2-(methoxymethyl)pyrrolidin-1-yl]-5-methylnicotinic acid
3-methyl-4-piperidin-1-ylbenzoic acid
4-piperidin-1-yl-3-(trifluoromethyl)benzoic acid is more particularly described in the Examples.

Alternatively, compounds of Formula (IV), wherein $R^b$ is defined as above and wherein $R^a$ is an aryl or heteroaryl group, can be obtained as outlined in Scheme 10. The first step consists of coupling a commercially available 4-bromobenzoic ester derivative with a commercially available aryl- or heteroaryl-boronic acid ($R^a$—B(OH)$_2$), a commercially available aryl- or heteroaryl-boronic pinacol ester or a commercially available aryl- or heteroaryl-tributylstannane, in the presence of a source of palladium such as tetrakis(triphenylphosphine)palladium(0) in a suitable solvent such as a mixture of toluene and water at a temperature rising from about 20° C. to about 150° C., preferably 120° C. for a few hours, preferably 1 to 14 hours in the presence or absence of a base such as TEA, DIEA, NaHCO$_3$ or K$_2$CO$_3$. The 4-arylbenzoic ester derivative obtained can then be hydrolysed to give compounds of Formula (IV) by the use of a metal hydroxide, e.g. lithium hydroxide, sodium hydroxide or potassium hydroxide, in a suitable solvent such as THF, methanol or water or mixtures thereof, at a temperature ranging from about 20° C. to about 50° C., preferably at room temperature, for a few hours, e.g. one hour to 24 h.

Scheme 10

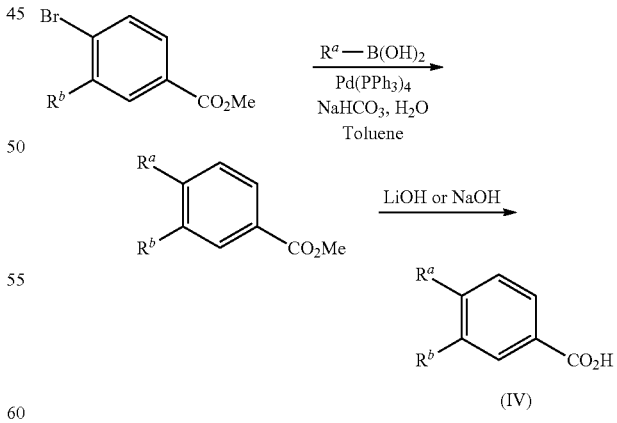

Alternatively, compounds of Formula (IV), wherein $R^a$ and $R^b$ are defined as above can be obtained as outlined in Scheme 11 when $R^a$ is an aryl or heteroaryl group. The first step consists of the esterification of a commercially available 4-boronicester-benzoic acid derivative using conditions and methods well known to those skilled in the art, such as thionyl chloride in methanol. This 4-boronicester-benzoic ester derivative intermediate can then be reacted with an halogenated- or trifluoromethanesulfonyl-aromatic or heteroaromatic in the presence of a source of palladium such as Pd(PPh₃)₄ in a suitable solvent such as a mixture of toluene and water at a temperature rising from about 20° C. to about 150° C., preferably 120° C. for a few hours, preferably 1 to 14 hours in the presence or absence of a base such as TEA, DIEA, NaHCO₃ or K₂CO₃. The 4-arylbenzoic ester derivative obtained can then be hydrolysed to give compounds of Formula (IV) by the use of a metal hydroxide, e.g. lithium hydroxide, sodium hydroxide or potassium hydroxide, in a suitable solvent such as THF, methanol or water or mixtures thereof, at a temperature ranging from about 20° C. to about 50° C., preferably at room temperature, for a few hours, e.g. one hour to 24 h.

hours, preferably 1 to 14 hours in the presence or absence of a base such as TEA, DIEA, NaHCO₃ or K₂CO₃. The 4-arylbenzoic ester derivative obtained can then be hydrolysed to give compounds of Formula (V) by the use of a metal hydroxide, e.g. lithium hydroxide, sodium hydroxide or potassium hydroxide, in a suitable solvent such as THF, methanol or water or mixtures thereof, at a temperature rising from about 20° C. to about 50° C., preferably at room temperature, for a few hours, e.g. one hour to 24 h.

Scheme 11

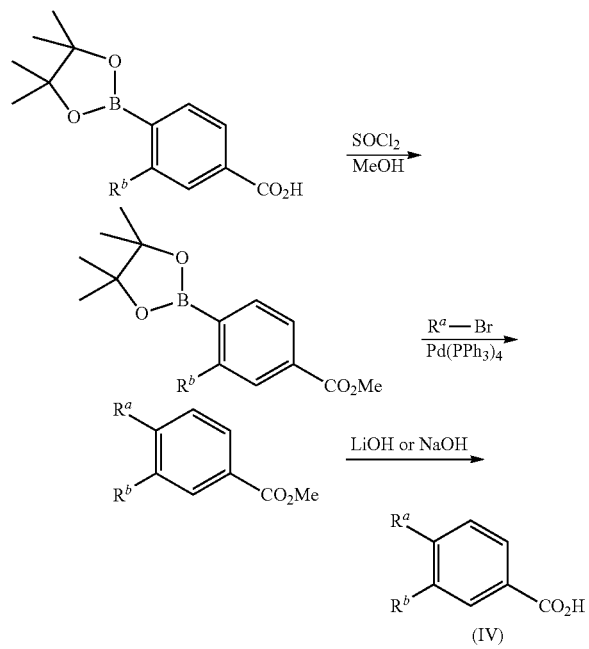

Scheme 12

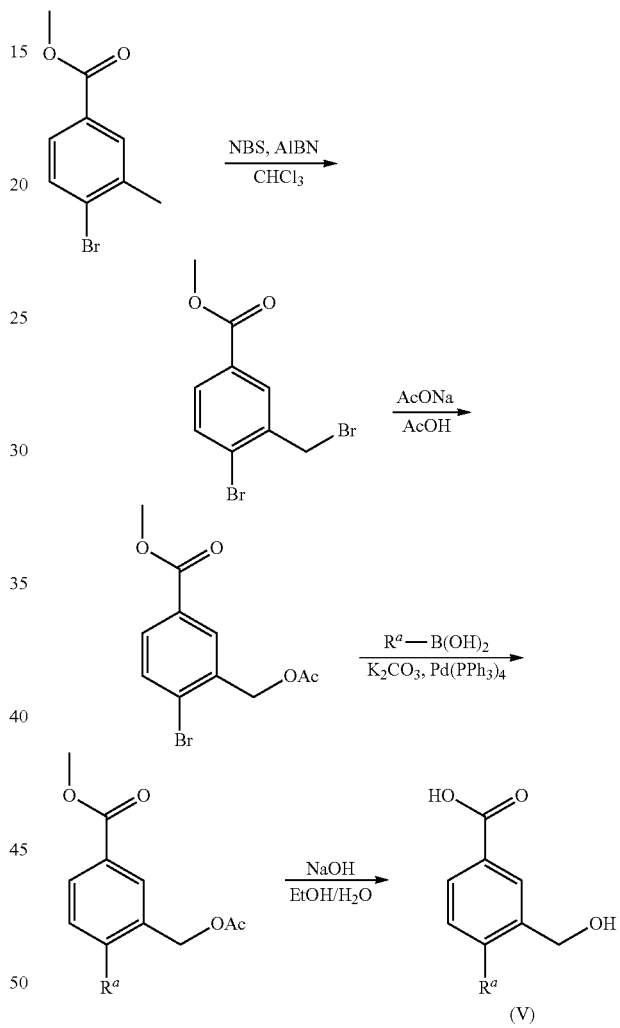

Alternatively, compounds of Formula (V), wherein R^a is an aryl or heteroaryl group, can be obtained as outlined in Scheme 12. The first step consists in bromination of 4-bromo-3-methyl-benzoic ester derivatives using conditions known by one skill in the art such as NBS in the presence of AIBN, in a suitable solvent such as CHCl₃ or DCE at a temperature rising from room temperature to about 120°, preferably between 60° C. and 100° C. for a few hours. The benzylic bromine of this intermediate can then be substituted by an alkylcarboxylate such as an acetate by reaction with AcONa in AcOH, at a temperature rising from room temperature to about 150°, preferably between 80° C. and 120° C. for a few hours, preferably between 5 and 24 hours. This intermediate can then be coupled with a commercially available aryl- or heteroaryl-boronic acid (R^a—B(OH)₂), a commercially available aryl- or heteroaryl-boronic pinacol ester or a commercially available aryl- or heteroaryl-tributylstannane, in the presence of a source of palladium such as tetrakis(triphenylphosphine)palladium(0) in a suitable solvent such as a mixture of toluene and water at a temperature rising from about 20° C. to about 150° C., preferably 120° C. for a few The method for preparing the compounds of Formula (V) selected below:
2,2'-dimethyl-1,1'-biphenyl-4-carboxylic acid
2-methyl-2'-(trifluoromethyl)biphenyl-4-carboxylic acid
3-methyl-4-(4-methyl-3-thienyl)benzoic acid
2'-methyl-2-nitro-1,1'-biphenyl-4-carboxylic acid
2'-methoxy-2-methylbiphenyl-4-carboxylic acid
2-methoxy-2'-methylbiphenyl-4-carboxylic acid
2',4'-dimethoxy-2-methylbiphenyl-4-carboxylic acid
3-methoxy-4-(4-methyl-3-thienyl)benzoic acid
4-(3,5-dimethylisoxazol-4-yl)-3-methylbenzoic acid
3-methyl-4-(2-methylpyridin-3-yl)benzoic acid
2-(hydroxymethyl)-2'-methylbiphenyl-4-carboxylic acid
is more particularly described in the Examples.

If the above set out general synthetic methods are not applicable for the obtention of compounds of Formula (I), suitable methods of preparation known by a person skilled in the art should be used.

The pharmaceutically acceptable cationic salts of compounds of the present invention are readily prepared by reacting the acid forms with an appropriate base, usually one equivalent, in a co-solvent. Typical bases are sodium hydroxide, sodium methoxide, sodium ethoxide, sodium hydride, potassium hydroxide, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of the cation (sodium ethylhexanoate, magnesium oleate), employing a solvent in which the desired cationic salt precipitates, or can be otherwise isolated by concentration and addition of a non-solvent.

According to a further general process, compounds of Formula (I) can be converted to alternative compounds of Formula (I), employing suitable interconversion techniques well known by a person skilled in the art.

In general, the synthesis pathways for any individual compound of Formula (I) will depend on the specific substitutents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, $3^{rd}$ Edition 1999.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) and, which contain an acid center, with a suitable base. Both types of salts may be formed or interconverted using ion-exchange resin techniques.

Depending on the conditions used, the reaction times are generally between a few minutes and 14 days, and the reaction temperature is between about −30° C. and 140° C., normally between −10° C. and 90° C., in particular between about 0° C. and about 70° C.

Compounds of the formula (I) can furthermore be obtained by liberating compounds of the formula (I) from one of their functional derivatives by treatment with a solvolysing or hydrogenolysing agent.

Preferred starting materials for the solvolysis or hydrogenolysis are those which conform to the formula (I), but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' denotes an amino-protecting group, instead of an HN group, and/or those which carry a hydroxyl-protecting group instead of the H atom of a hydroxyl group, for example those which conform to the formula (I), but carry a —COOR" group, in which R" denotes a protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or hetero-cyclic carboxylic acids or sulfonic acids, and, in particular, alkoxy-carbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-carbonyl, ethoxycarbonyl, 2,2,2-trichloroethoxycarbonyl, BOC (tert-butoxy-carbonyl) and 2-iodoethoxycarbonyl; aralkoxycarbonyl, such as CBZ ("carbo-benz-oxy"), 4-methoxybenzyloxycarbonyl and FMOC; and aryl-sulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitro-benzoyl, p-toluenesulfonyl, tert-butyl and acetyl, where benzyl and tert-butyl are particularly preferred.

The compounds of the formula (I) are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBu and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, tri-fluoro-methylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl-formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be saponified, for example, using acetic acid or using LiOH, NaOH or KOH in water, water/THF, water/THF/ethanol or water/dioxane, at temperatures between 0 and 100° C.

Free amino groups can furthermore be acylated in a conventional manner using an acid chloride or anhydride or alkylated using an unsubstituted or substituted alkyl halide or reacted with CH$_3$—C(=NH)—OEt, advantageously in an inert solvent, such as dichloromethane or THF and/or in the presence of a base, such as triethylamine or pyridine, at temperatures between −60° C. and +30° C.

Therefore, the invention also relates to the preparation of the compounds of formula (I), and salts thereof, characterized in that
a) a compound of formula A

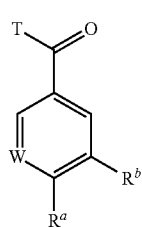

A wherein W, $R^a$ and $R^b$ have the meanings given above, and T is OH, or a leaving group, such as Cl, Br, I, imidazolyl, pentafluorophenoxy or the product of the reaction of isobutyl chloroformate with formula A, wherein T is OH, is reacted with a compound of formula B

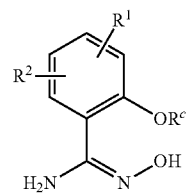

wherein $R^1$, $R^2$ and $R^c$ have the meanings given above, preferably in the presence of a solvent and of a suitable base, such as an amine like TEA, DIEA or NMM, or in case T is OH, in the presence of a suitable condensation reagent, such as EDC and the resulting product is cyclized, preferably in the presence of an amine, such as DIEA, TEA or tetrabutylammonium fluoride and optionally a base or acid of the formula (I) is converted into one of its salts.

Throughout the specification, the term leaving group preferably denotes Cl, Br, I or a reactively modified OH group, such as, for example, an activated ester, an imidazolide or alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N-hydroxysuccinimide.

The formula (I) also encompasses the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds of the formula (I) and so-called prodrug compounds.

The term "prodrug derivatives" is taken to mean compounds of the formula (I) which have been modified with, for example, alkyl or acyl groups, sugars or oligopeptides and which are rapidly cleaved in the organism to form the active compounds.

These also include biodegradable polymer derivatives of the compounds according to the invention, as described, for example, in Int. J. Pharm. 115, 61-67 (1995).

The Formula (I) also encompasses compounds wherein $R^a$ is OA wherein A is as above described.

The formula (I) also encompasses compounds wherein $R^c$ is H.

The Formula (I) also encompasses compounds wherein Het denotes a saturated, unsaturated or aromatic heterocyclic ring having 1 to 4 N atoms.

The formula (I) also encompasses mixtures of the compounds of the formula (I), for example mixtures of two diastereomers, for example in the ratio 1:1, 1:2, 1:3, 1:4, 1:5, 1:10, 1:100 or 1:1000.

These are particularly preferably mixtures of stereoisomeric compounds.

In a preferred embodiment, the invention provides compounds of Formula (I')

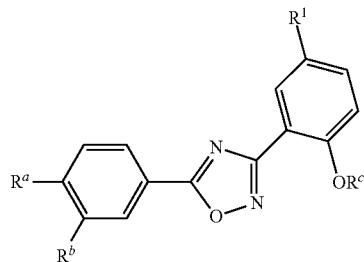

I' wherein $R^a$, $R^b$, are as above defined
$R^1$ is H or F
$R^c$ is $CF_3$ or Me In another preferred embodiment, the invention provides compounds of Formula (I")

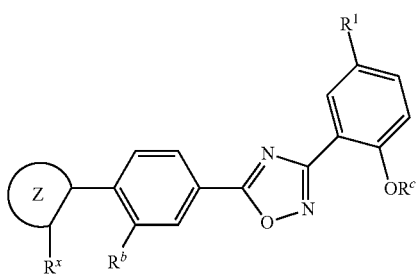

I"

wherein $R^b$, $R^c$ and $R^1$ are as defined under Formula (I) and wherein $R^x$ denotes Hal, A, $CH_2OA$, $CH_2N(R_3)_2$, $OR^3$, $N(R^3)_2$, $NO_2$, $N(SO_2)Me)_2$, CN, $COOR^3$, $CF_3$, $OCF_3$, CON$(R^3)_2$, $NR^3COA$, $NR^3CON(R^3)_2$, $NR^3SO_2A$, $COR^3$, $SO_2N(R^3)_2$, SOA or $SO_2A$, phenyl, pyridyl, $-[C(R^3)_2]_n-COOR^3$ or $-O[C(R^3)_2]_nCON(R^3)_2$. Preferably $R^x$ is in such position that it limits the rotation of the ring Z with respect to the ring bearing $R^b$, by the meaning of steric hindrance or electrostatic interactions with $R^b$. $R^x$ is preferably an alkyl or an alkoxy chain containing 1 to 5 carbon atoms. $R^x$ is most preferably attached to the atom adjacent to the atom which links the ring Z to the rest of the molecule. $R^x$ is most preferably $-CH_3$, $-C_2H_5$, F, Cl, $-OCH_3$, $-CH_2OCH_3$ and $R^b$ is simultaneously $-CH_3$, $-C_2H_5$, F, Cl, $-OCH_3$, $-OC_2H_5$, $-CH_2OCH_3$, $-CH_2OH$, $-CH_2N(CH_3)_2$, $CF_3$.

Preference is given to the compounds of the present invention selected from the following group I1 to I79:

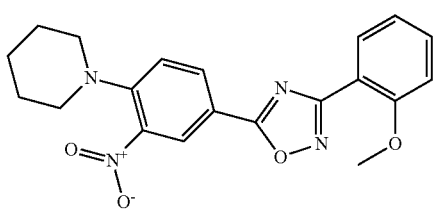

I1

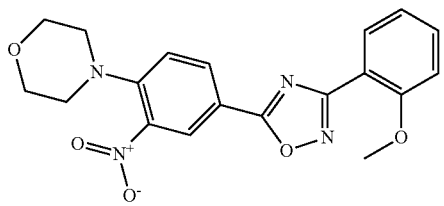

I2

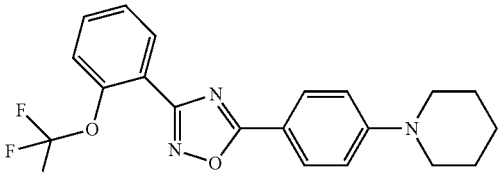

I3

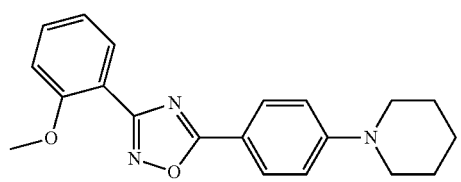

I4

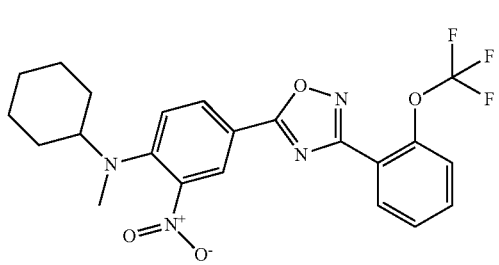

I5

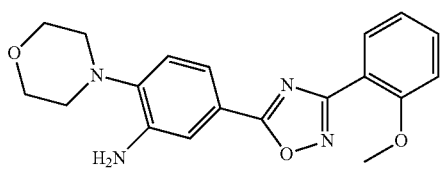

I6

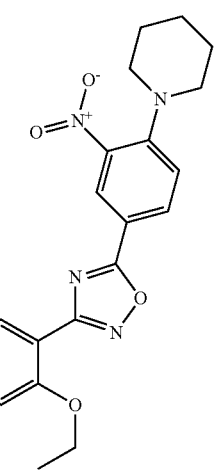

I7

-continued

-continued
I22
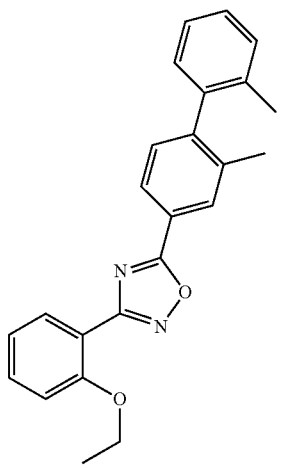
I23
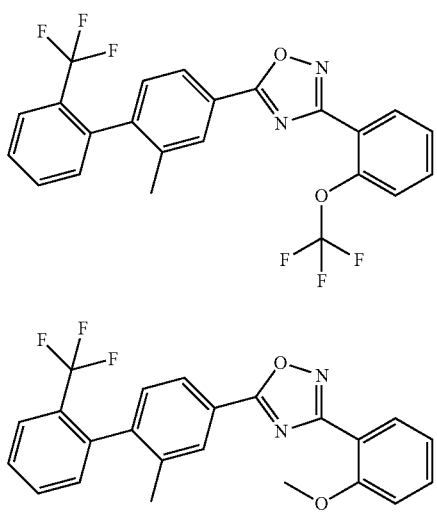
I24
I25
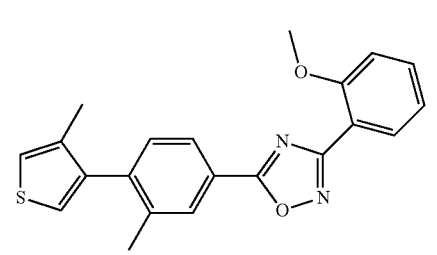
I26
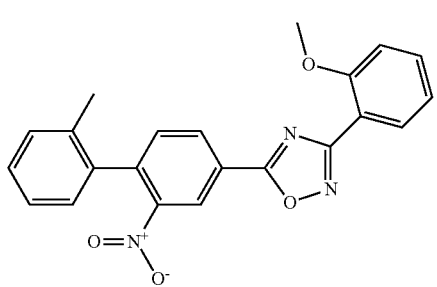
-continued
I27
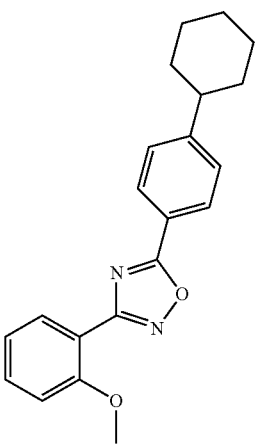
I28
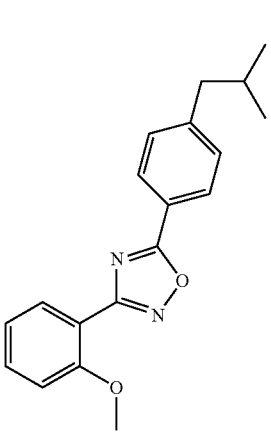
I29
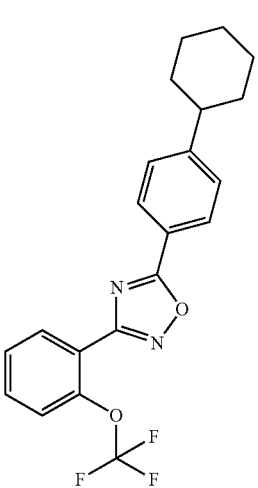

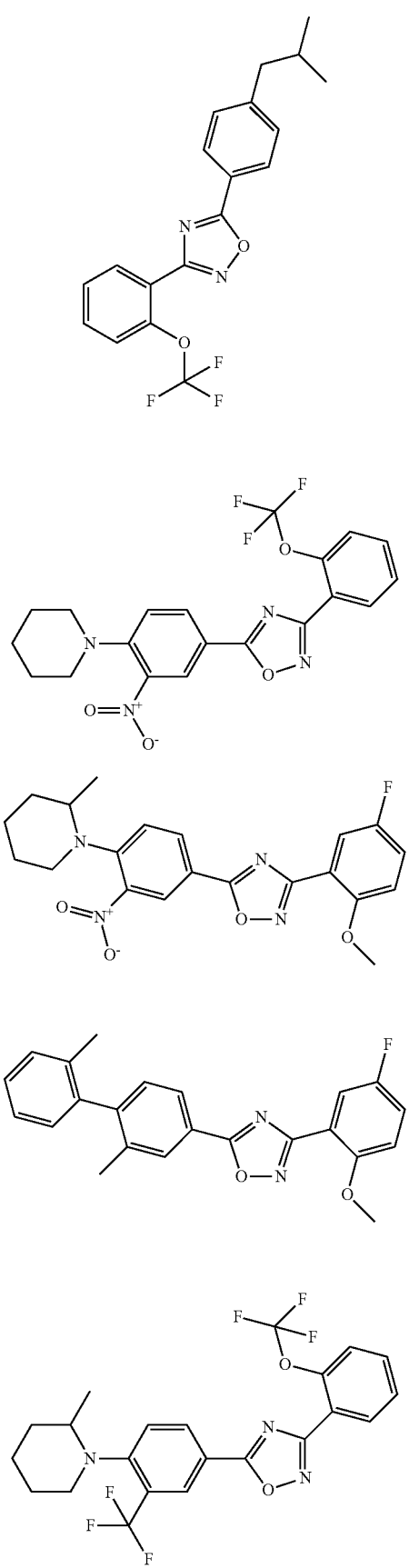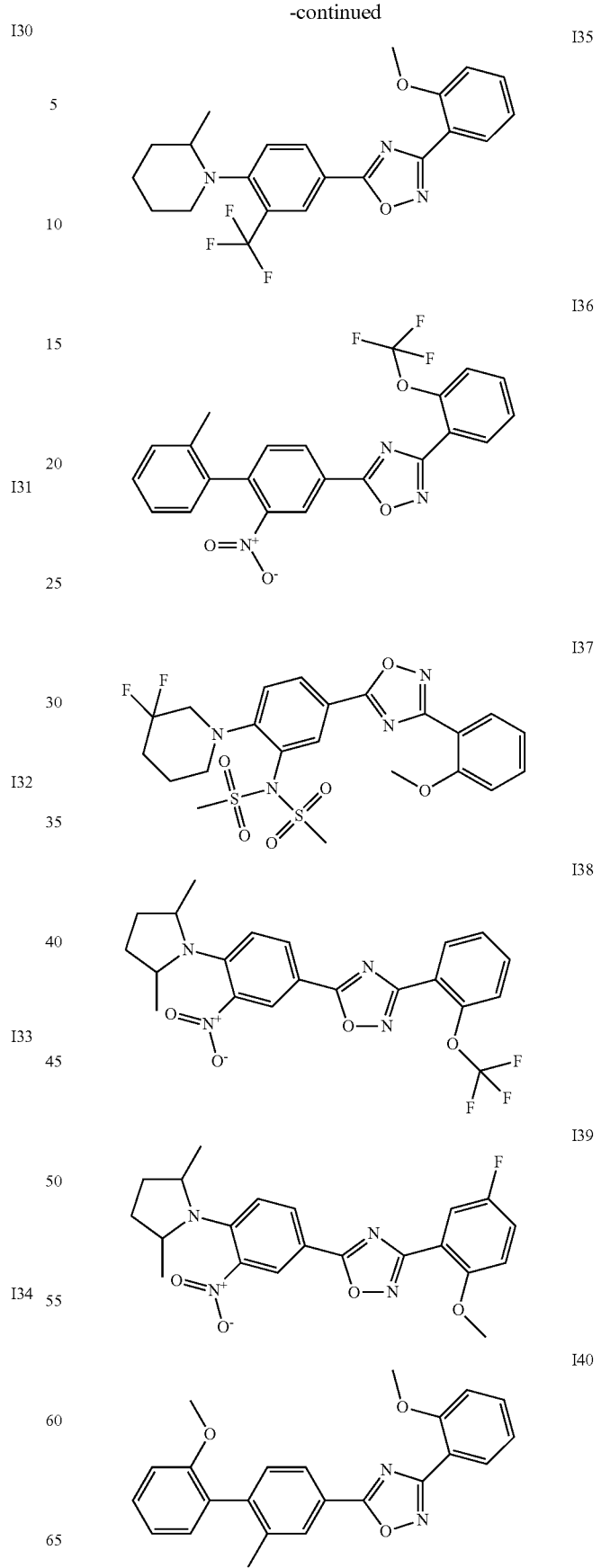

I41 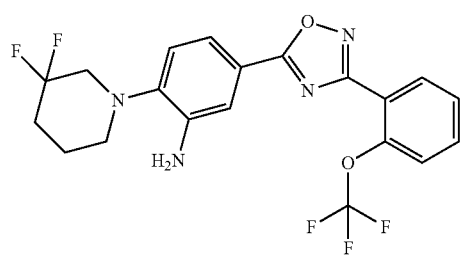
I42 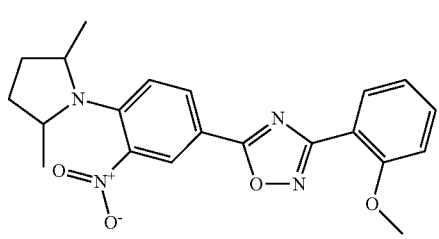
I43 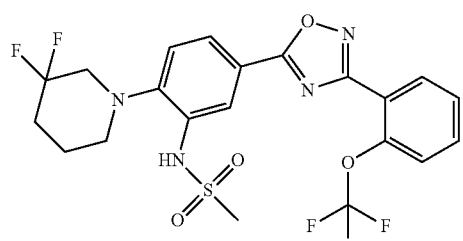
I44 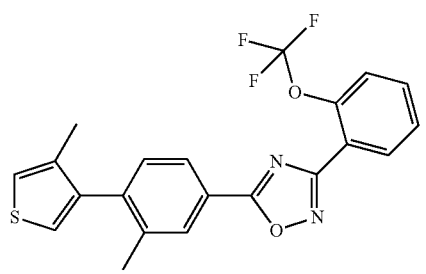
I45 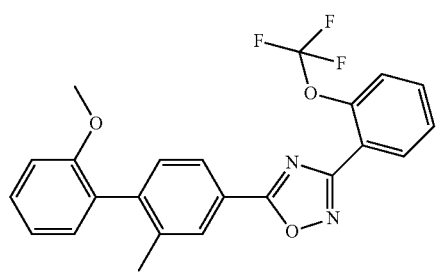
I46 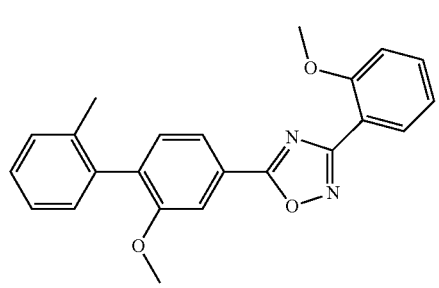
I47 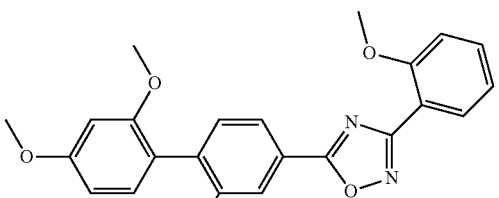
I48 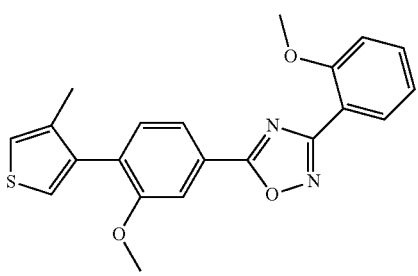
I49 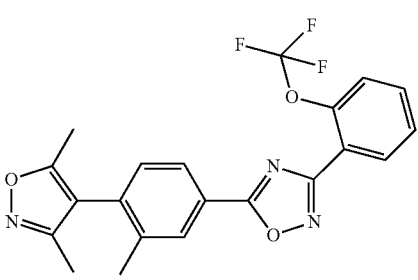
I50 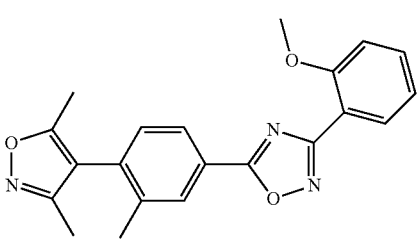
I51 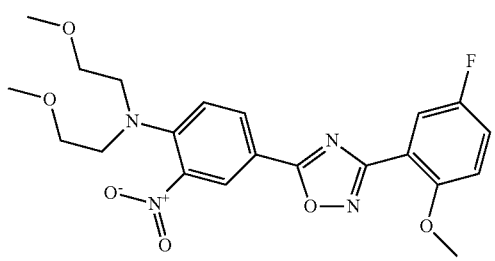
I52 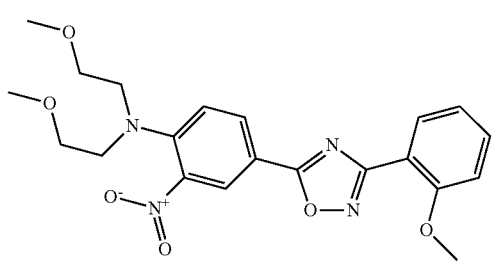

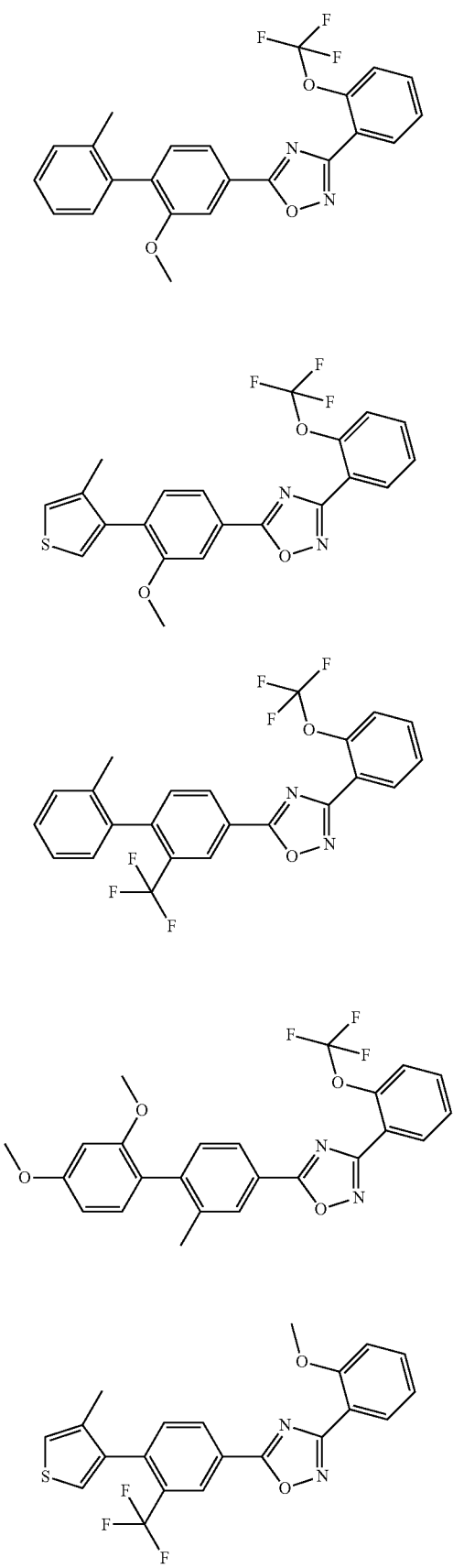
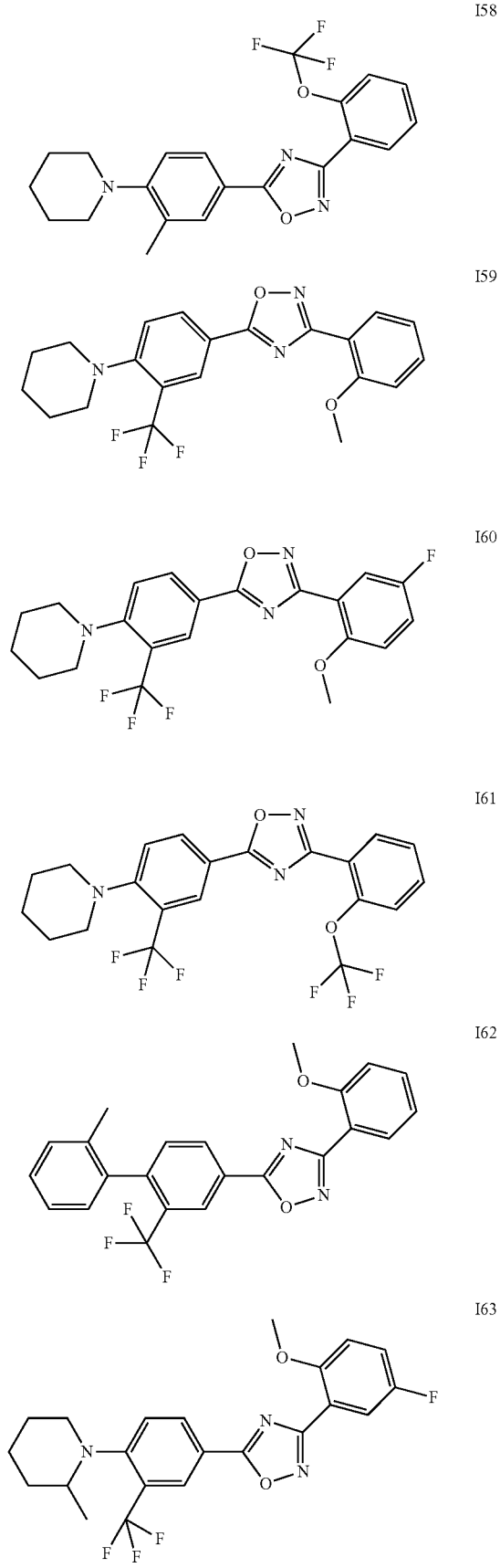

I64
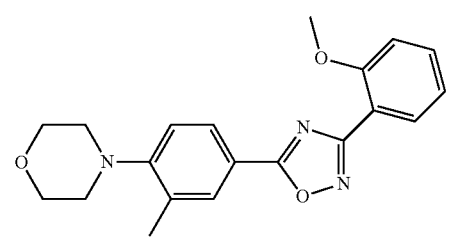
I65
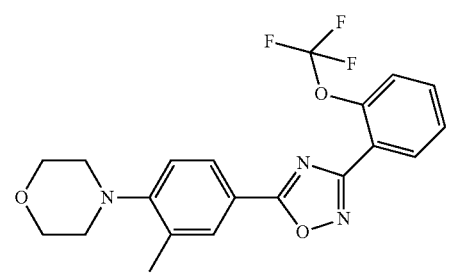
I66
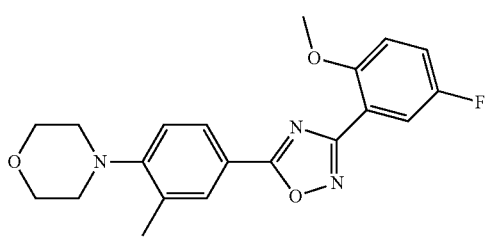
I67
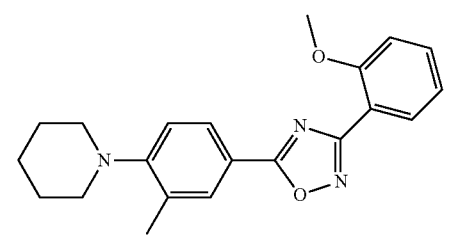
I68
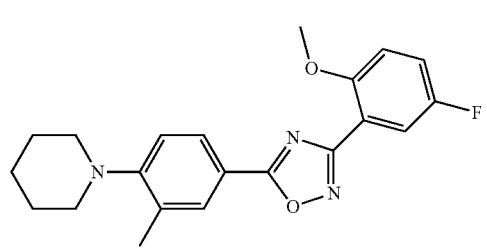
I69
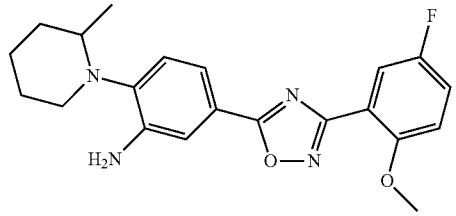
I70
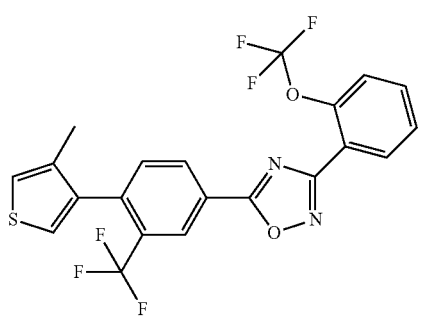
I71
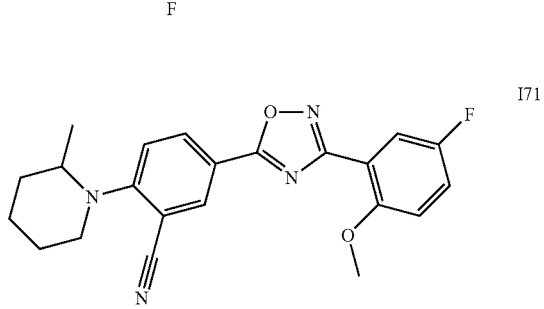
I72
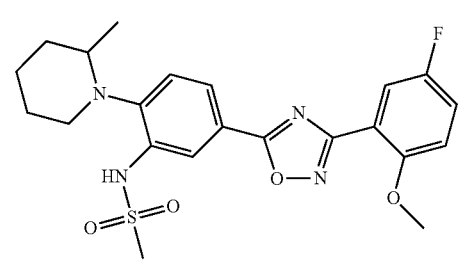
I73
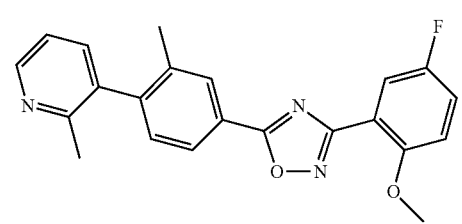
I74
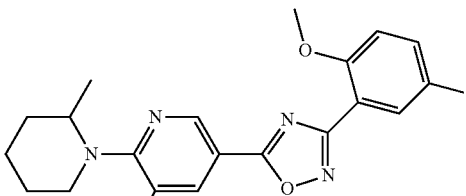
I75
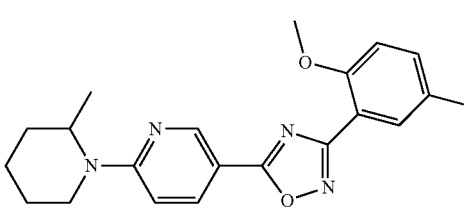

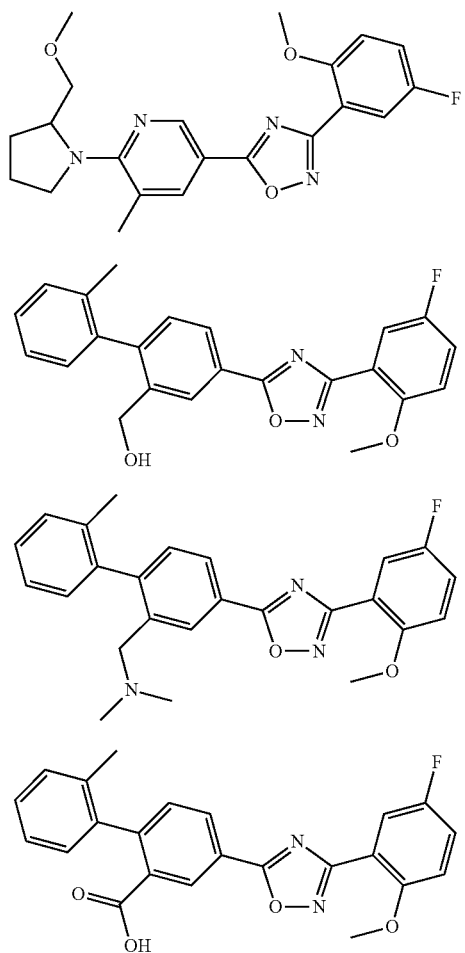

and pharmaceutically usable derivatives, solvates, salts and stereoisomers thereof, including mixtures thereof in all ratios.

For all radicals which occur more than once, their meanings are independent of one another.

Above and below, the radicals or parameters $R^a$, $R^b$, $R^c$, $R^1$, $R^2$, $R^3$, W, T, X, A, Ar, Het and n have the meaning indicated under the formula I, unless expressly stated otherwise.

A denotes alkyl, is unbranched (linear) or branched, and has 1, 2, 3, 4, 5, 6, 7, 8, 9, 10, 11 or 12 carbon atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 carbon atoms, preferably methyl, ethyl, propyl, isopropyl, butyl, isobutyl, sec-butyl, tert-butyl, pentyl, hexyl, trifluoromethyl, pentafluoroethyl, 1,1,1-trifluoroethyl. In a preferred embodiment A is perfluorated. A furthermore denotes —(CH$_2$)$_n$O(CH$_2$)$_n$OR$^3$, —(CH$_2$)$_n$NR$^3$(CH$_2$)$_2$N(R$^3$)$_2$, especially —(CH$_2$)$_2$O(CH$_2$)$_2$OR$^3$ or —(CH$_2$)$_2$NH(CH$_2$)$_2$N(R$^3$)$_2$.

Cycloalkyl are cyclic alkyl containing 3 to 12 carbon atoms.

Cycloalkyl preferably denotes cyclopropyl, cyclobutyl, cyclopentyl, cyclohexyl or cycloheptyl.

Cycloalkylalkylene is a cycloalkyl group bond to the rest of the molecule via a carbon chain and having 1, 2, 3, 4, 5, 6, 7, 8, 9, 10, 11, 12, 13, 14, 15, 16, 17, or 18 carbon atoms. Cycloalkylalkylene preferably denotes cyclopropylmethylene, cyclobutylmethylene, cyclopentylmethylene, cyclohexylmethylene or cycloheptylmethylene.

Alkylene is a bivalent carbon chain having 1, 2, 3, 4, 5, 6, 7, 8, 9, 10, 11, or 12 carbon atoms. Alkylene is preferably methylene, ethylene, propylene, butylene, pentylene or hexylene, furthermore branched alkylene.

$R^a$ is preferably Ar, Het or OA especially Ar or Het.

If Het denotes a N-Atom bearing saturated heterocycle, Het is preferably linked to the rest of the molecule via an N-Atom. The alpha position is next to this N-Atom.

$R^b$ is preferably H, A, OH, OA, especially —OCH$_3$, —OCF$_3$, —CH$_3$, —NO$_2$, Hal, —CH$_2$OR$^3$, —CH$_2$NHSO$_2$A, —NHSO$_2$A, —NH$_2$, —CH$_2$NHCOCH$_3$, —CH$_2$N(CH$_3$)$_2$, —CH$_2$NH$_2$, —NHCONH$_2$, —(CH$_2$)$_n$SO$_2$R$^3$, —N(SO$_2$A)$_2$, —CO$_2$R$^3$, or —CF$_3$.

The invention also encompasses compounds of Formula (I) wherein $R^b$, OR$^3$, CN, or Hal.

$R^c$ preferably denotes alkyl, polyfluoralkyl or perfluoralkyl, especially —CH$_3$, —C$_2$H$_5$ or —CF$_3$.

Compounds of formula (I), wherein $R^c$ denotes H are preferred as intermediates for the synthesis of other compounds of formula I.

$R^3$ is preferably A.

Hal is preferably F, Cl or Br and especially F or Cl.

Preferably, at least one of $R^1$ and $R^2$ denotes F or Cl.

$R^1$ preferably denotes F or H.

$R^1$ is preferably in para position to the group OR$^c$.

$R^2$ is preferably F or H, especially H.

W preferably denotes CH.

N is preferably 0, 1, 2, 3, 4 or 5 and more preferably 0, 1, 2, 3 or 4.

An aromatic carbocyclic ring preferably denotes phenyl, naphthyl or biphenyl.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)-phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o, m or pamino-sulfanyl-phenyl, o-, m- or p-phenoxyphenyl, further preferably 2,3-, 2,4-, 2,5-, 2,6-, 3,4- or 3,5-dimethylphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4- methoxyphenyl, 3-amino-6-methylphenyl, 3-chloro-4-acetamidophenyl or 2,5-dimethyl-4-chlorophenyl.

Ar preferably denotes, for example, phenyl which is unsubstituted or monosubstituted, disubstituted or trisubstituted by A, Hal, $OR^3$, $CF_3$, $OCF_3$, $NO_2$ and/or CN. If Ar is phenyl, it is preferably substituted in 2' position, i.e. in ortho-position to the oxadiazole bearing moiety. Ar is preferably substituted by A, $OR^3$, $CF_3$ $OCF_3$.

Ar particularly preferably denotes, for example, phenyl which is unsubstituted or monosubstituted or disubstituted preferably monosubstituted, by F, $OCH_3$, $CH_3$, $CF_3$, phenyl and/or pyridyl, such as, for example, 2'-methoxy-phenyl-, 2'-trifluoromethyl-phenyl- (aryl bearing at least a 2' substituent), 2'-chloro-phenyl, 2',6'-dimethyl-phenyl- or 2'-alkyl-phenyl-, preferably 2'-methyl-phenyl.

Ar very particularly preferably denotes one of the following groups:

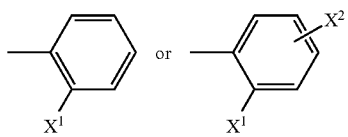

preferably

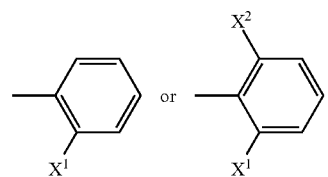

Wherein $X^1$ and $X^2$ are independently of one another F, Cl, —$OCH_3$, —$CH_3$, —$C_2H_5$, —$CF_3$, —$OCF_3$, —O-isoPropyl, —O-isobutyl, —$OCH_2CN$, —$OCH_2$cyclopropyl, —$CH_2OH$, —$CH_2$O-isoPropyl, —$CH_2$O-isobutyl, —$CH_2OCH_2$cyclopropyl, —$CH_2NMe_2$, —$CH_2OC_2H_5$, —NHCOMe, —NHCOEt, —$NHSO_2NMe_2$, —$NHSO_2$propyl, —$CH_2$morpholine, —$CH_2$pirolidine, —$CH_2NHMe$, —$SO_2Me$, —$CH_2SO_2Me$, —C≡C— $CH_2OMe$, —$(CH_2)_3OMe$, —$O(CH_2)_2OMe$, —$CO_2H$, —OH, —$NO_2$, —CN, —$NHSO_2CH_3$, and/or phenyl or pyridyl or piperidine or morpholine, which is preferably unsubstituted.

More preferably, $X^1$ and $X^2$ denote independently of one another —F, —$OCH_3$, —$CH_3$, —$CF_3$, —$OCF_3$, —OH, —$NO_2$, —CN, and/or phenyl or pyridyl, which is preferably unsubstituted.

Het is preferably a 6 to 14 membered ring system and denotes, not withstanding further substitutions, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, indazolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxane-6-yl, 2,1,3-benzothiadiazol-4- or -5-yl or 2,1,3-benzoxadiazol-5-yl.

The heterocyclic radicals may also be partially or fully hydrogenated.

Het can thus also denote, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-,-3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het very particularly denotes one of the following groups:

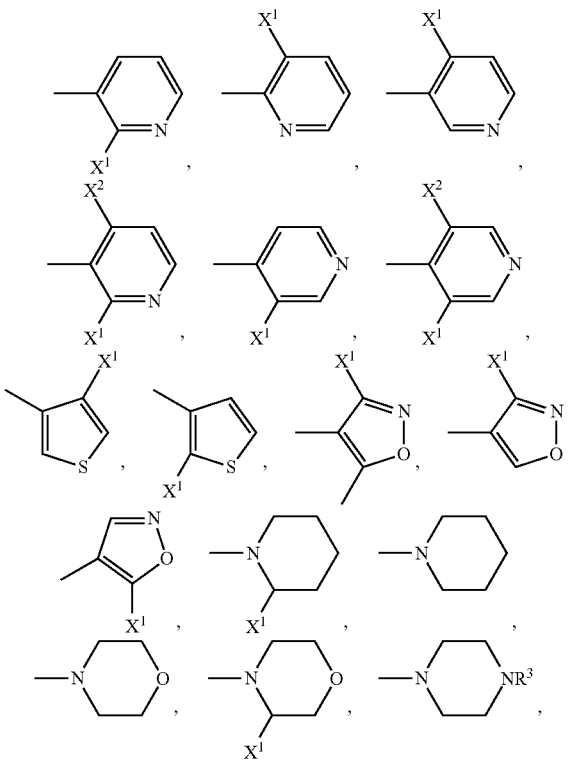

-continued

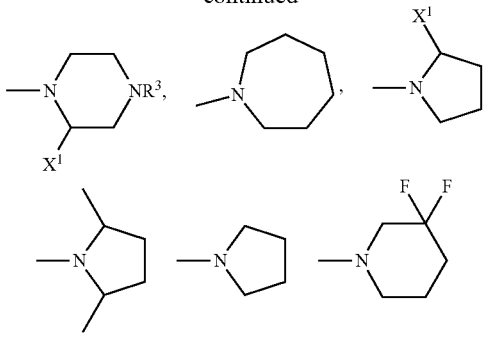

wherein $X^1$, $X^2$, and $R^3$ are as defined above.

The compounds of the formula (I) can have one or more centres of chirality and can therefore occur in various stereoisomeric forms. The formula (I) covers all these forms.

Accordingly, the invention relates, in particular, to compounds of Formula (I) and its use, in which at least one of the said radicals has one of the preferred meanings indicated above. Some preferred groups of compounds can be expressed by the following sub-formulae Ia to Ih, which conform to the formula I and in which the radicals not designated in greater detail have the meaning indicated under the formula (I), but in which in Ia $R^a$ Ar or Het.

in Ib $R^a$ is heterocycloalkyl or heteroaryl which both may be unsubstituted or monosubstituted or disubstituted, preferably monosubstituted, by F, $OCH_3$, $CH_3$, $CF_3$, such as, for example, morpholino-4-yl or 2-methyl-piperidin-1-yl, in Ic $R^1$ and $R^2$ denote H.

in Id $R^a$ is heterocycloalkyl such as morpholino-4-yl and 2-methyl-piperidin-1-yl $R^b$ is polyfluoroalkyl, $R^c$ is selected from alkyl, polyfluoroalkyl, in Ie $R^a$ is heterocycloalkyl such as morpholino-4-yl $R^b$ is amino, $R^c$ is selected from alkyl, in If $R^a$ is heterocycloalkyl such as morpholino-4-yl, 2-methyl-piperidin-1-yl, 3,3-difluoropiperidin-1-yl and piperidin-1-yl $R^b$ is nitro, $R^c$ is alkyl, in Ig $R^a$ is heterocycloalkyl such as morpholino-4-yl, 2-methyl-piperidin-1-yl, 3,3-difluoropiperidin-1-yl and piperidin-1-yl $R^b$ is nitro, $R^c$ is polyfluoroalkyl, in Ih $R^a$ is pyrrolidin-1-yl $R^b$ is nitro, $R^c$ is selected from alkyl, polyfluoroalkyl, in Ii $R^a$ is aryl or heteroaryl such as tol-2-yl, 2-trifluoromethylphen-1-yl and 4 methylthien-3-yl $R^b$ is selected from alkyl, nitro, $R^c$ is selected from alkyl, polyfluoroalkyl, and pharmaceutically usable derivatives, solvates, salts and stereoisomers thereof, including mixtures thereof in all ratios.

The compounds of the formula (I) and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), under reaction conditions which are known and suitable for the said reactions. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, $3^{rd}$ Edition 1999.

Use can also be made here of variants which are known per se, but are not mentioned here in greater detail.

If desired, the starting materials can also be formed in situ so that they are not isolated from the reaction mixture, but instead are immediately converted further into the compounds of the formula (I).

The starting compounds for the preparation of compounds of formula (I) are generally known. If they are novel, they can, however, be prepared by methods known per se.

The reactions are preferably carried out in an inert solvent.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Pharmaceutical Salts and Other Forms

The said compounds of the formula (I) can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula (I) are for the most part prepared by conventional methods. If the compound of the formula (I) contains an acidic center, such as a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example sodium- or potassiumethoxide and sodium or potassiumpropoxide, alkalihydrides, such as sodium- or potassiumhydride; and various organic bases, such as piperidine, diethanolamine and N-methyl-glutamine, benzathine, choline, diethanolamine, ethylenediamine, meglumine, benethamine, diethylamine, piperazine and tromethamine. The aluminium salts of the compounds of the formula (I) are likewise included. In the case of certain compounds of the formula (I), which contain a basic center, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoaryl-sulfonates, such as ethanesulfonate, toluenesulfonate and benzene-sulfonate, and other organic acids and corresponding salts thereof, such as acetate, trifluoro-acetate, tartrate, maleate, succinate, citrate, benzoate, salicylate, ascorbate and the like. Accordingly, pharmaceutically acceptable acid-addition salts of the compounds of the formula (I) include the following: acetate, adipate, alginate, arginate, aspartate, benzoate, benzene-sulfonate (besylate), bisulfate, bisulfite, bromide, butyrate, camphorate, camphor-sulfonate, caprylate, chloride, chlorobenzoate, citrate, cyclo-pentane-propionate, digluconate, dihydrogen-phosphate, dinitrobenzoate, dodecyl-sulfate, ethanesulfonate, fumarate, galacterate (from mucic acid), galacturonate, glucoheptanoate, gluco-nate, glutamate, glycerophosphate, hemi-succinate, hemisulfate, heptanoate, hexanoate, hippurate, hydro-chloride, hydrobromide, hydroiodide, 2-hydroxy-ethane-sulfonate, iodide, isethionate, isobutyrate, lactate, lactobionate, malate, maleate, malonate, mandelate, metaphosphate, methanesulfonate, methylbenzoate, mono-hydrogen-phosphate, 2-naphthalenesulfonate, nicotinate, nitrate, oxalate, oleate, palmo-ate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of the formula (I) include aluminium, ammonium, calcium, copper, iron(III), iron(II), lithium, magne-sium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula (I) which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzyl-ethylen-ediamine (benzathine), dicyclohexylamine, diethanol-amine, diethyl-amine, 2-diethyl-amino-ethanol, 2-dimethyl-amino-ethanol, ethanolamine, ethylenediamine, N-ethylmorpholine, N-ethyl-piperidine, glucamine, glucosamine, histidine, hydrabamine, isopropyl-amine, lidocaine, lysine, meglumine (N-methyl-D-glucamine), morpholine, piperazine, piperidine, polyamine resins, procaine, purines, theobromine, triethanol-amine, triethylamine, trimethylamine, tripropyl-amine and tris(hydroxy-methyl)-methylamine (tromethamine), but this is not intended to represent a restriction.

Compounds of the formula (I) of the present invention which contain basic nitrogen-containing groups can be quaternised using agents such as (C1-C4)-alkyl halides, for example methyl, ethyl, isopropyl and tert-butyl chloride, bromide and iodide; di(C1-C4)alkyl sulfates, for example dimethyl, diethyl and diamyl sulfate; (C10-C18)alkyl halides, for example decyl, do-decyl, lauryl, myristyl and stearyl chloride, bromide and iodide; and aryl-(C1-C4)alkyl halides, for example benzyl chloride and phenethyl bromide. Both water- and oil-soluble compounds of the formula (I) can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, me-glumine, nitrate, oleate, phosphonate, pivalate, sodium phosphate, stea-rate, sulfate, sulfosalicylate, tartrate, thiomalate, tosylate and tro-meth-amine, but this is not intended to represent a restriction.

The acid-addition salts of basic compounds of the formula (I) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula (I) are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine.

The base-addition salts of acidic compounds of the formula (I) are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound of the formula (I) contains more than one group which is capable of forming pharmaceutically acceptable salts of this type, the formula (I) also encompasses multiple salts. Typical multiple salt forms include, for example, bitartrate, diacetate, difumarate, dimeglumine, di-phosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula (I) in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula (I) can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of compounds of formula (I), in combination with at least one further medicament active ingredient, preferably medicaments used in the treatment of multiple sclerosis such as cladribine or another co-agent, such as interferon, e.g. pegylated or non-pegylated interferons, preferably interferon beta and/or with compounds improving vascular function. These further medicaments, such as interferon beta, may be administered concomitantly or sequentially, e.g. by subcutaneous, intramuscular or oral routes.

These compositions can be used as medicaments in human and veterinary medicine.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting molds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I) and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula (I) and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insuf-flators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the rec-ipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula (I) and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a sphingosine 1-phosphate associated disorder, comprising administering to said subject an effective amount of a compound of formula (I). The present invention preferably relates to a method, wherein the sphingosine 1-phosphate-1 associated disorder is an autoimmune disorder or condition associated with an overactive immune response.

The present invention furthermore relates to a method of treating a subject suffering from an immunerogulatory abnormality, comprising administering to said subject a compound of formula (I) in an amount that is effective for treating said immunoregulatory abnormality. The present invention preferably relates to a method wherein the immunoregulatory abnormality is an autoimmune or chronic inflammatory disease selected from the group consisting of: amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Preferred compounds of formula (I) exhibit a binding constant Ki for the binding to the $S1P_1$ receptor of less than about 5 μM, preferably less than about 1 μM and even more preferred less than about 0.1 μM.

Nomenclature of the compounds of this invention has been determined using ACD/Name Version 7.10 software.

In the following the present invention shall be illustrated by means of some examples, which are not construed to be viewed as limiting the scope of the invention.

EXAMPLES

The HPLC data provided in the examples described below were obtained as followed: Method A: HPLC columns: Xbridge™ $C_8$ column 50 mm×4.6 mm at a flow of 2 mL/min with 8 min gradient from 0.1% TFA in $H_2O$ to 0.07% TFA in $CH_3CN$. UV detection (maxplot).

Method B: HPLC columns: BDS $C_{18}$ column 50 mm×4.6 mm at a flow of 0.8 mL/min with 8 minutes gradient from 0.1% TFA in $H_2O$ to $CH_3CN$. UV detection (maxplot).

The MS data provided in the examples described below were obtained as followed:
LC/MS Waters ZMD (ESI).

The NMR data provided in the examples described below were obtained as followed: $^1$H-NMR: Bruker DPX-300 MHz or 400 MHz.

The microwave chemistry is performed on a single mode microwave reactor Emrys™ Optimiser from Personal Chemistry.

General Procedure 1 for the Formation of Oxadiazole Derivatives

Trichloroacetonitrile was added to a suspension of the benzoic acid of Formula (IV) and polymer bound triphenylphosphine in THF (2 mL) and the reaction mixture was stirred at 100° C. for 5 minutes in the microwave. A solution of the amidoxime of Formula (III) and DIEA in THF (2 mL) was then added and the reaction mixture was stirred at 150° C. for 15 minutes in the microwave. The reaction mixture was then filtered through a SPE-$NH_2$ column, which was further washed with THF. After concentration in vacuo, the residue was purified by column chromatography and/or crystallization.

General Procedure 2 for the Formation of Oxadiazole Derivatives

Oxalyl chloride was added to a suspension of the benzoic acid of Formula (IV) and DMF (catalytic amount) in DCM (2 mL) and the reaction mixture was stirred at room temperature for 30 minutes to 1 hour. After concentration to dryness, the residue was taken up in THF (2 mL) and added to a solution of the amidoxime of Formula (III) and DIEA in THF (1 mL). The reaction mixture was then stirred at 150° C. for 30 minutes in the microwave. After cooling, the mixture was filtered through a SPE-$NH_2$ column, which was further washed with THF. After concentration in vacuo, the residue was purified by column chromatography and/or crystallization.

Intermediate 1:
N'-Hydroxy-2-methoxybenzenecarboximidamide

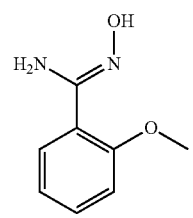

Hydroxylamine (Fluka 55458; 50% in water; 11.28 mL; 187.76 mmol; 5 eq.) was added to a solution of 2-methoxybenzonitrile (Alrich 231231; 4.59 mL; 37.55 mmol; 1 eq.) in EtOH (50 mL) and the resulting mixture was stirred at room temperature for 16 hours then at 55° C. for 24 hours. The solvent was then evaporated and the resulting colourless oil was further dried under high vacuum to give a white solid. The latter was triturated in n-hexane, filtered and dried to afford the title compound (6.29 g, quantitative) as a white solid.

HPLC (Method A): Rt 0.96 min (purity 99.2%).

Intermediate 2: N'-Hydroxy-2-(trifluoromethoxy)benzenecarboximidamide

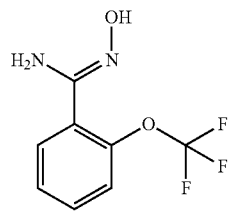 [SMILES: N/C(=N\O)c1ccccc1OC(F)(F)F]

Hydroxylamine (Fluka 55458; 50% in water; 4.81 mL; 80.16 mmol; 5 eq.) was added to a solution of 2-(trifluoromethoxy)benzonitrile (Apollo PC7438E; 3 g; 16.03 mmol; 1 eq.) in EtOH (20 mL) and the reaction mixture was stirred at 60° C. for 10 hours. Evaporation in vacuo gave a white solid, which was further dried under high vacuum to afford the title compound (3.30 g, 94%) as a white solid.

$^1$H NMR (DMSO-d$_6$, 300 MHz) δ 9.61 (1H, s), 760-7.47 (2H, m), 7.45-7.35 (2H, m), 5.80 (2H, s).

Intermediate 3: 2-Ethoxy-N'-hydroxybenzenecarboximidamide

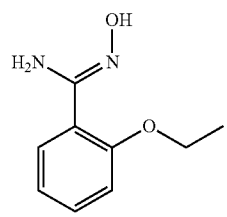

Hydroxylamine (Fluka 55458; 50% in water; 4.08 mL; 67.95 mmol; 5 eq.) was added to a solution of 2-ethoxybenzonitrile (Fluorochem 18661; 2 g; 13.59 mmol; 1 eq.) in EtOH (30 mL) and the reaction mixture was stirred at 50° C. for 12 hours. Evaporation in vacuo gave a white solid, which was further dried under high vacuum to afford the title compound (2.38 g, 97%) as a white solid.

HPLC (Method A): Rt 1.22 min (purity 98.2%). LC/MS: 181.0 (M+H)$^+$.

Intermediate 4: 3-Nitro-4-piperidin-1-ylbenzoic acid

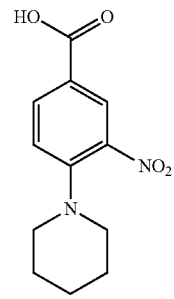 [SMILES: O=C(O)c1ccc(N2CCCCC2)c([N+](=O)[O-])c1]

A mixture of ethyl 4-fluoro-3-nitrobenzoate (Chontech 01072; 500 mg; 2.35 mmol; 1 eq.) and piperidine (Fluka 80640; 599.18 mg; 7.04 mmol; 3 eq.) in DMF (2 mL) was stirred at 50° C. for 3 hours. The reaction was then allowed to cool to room temperature and diluted with water. Extraction with ethyl acetate, drying over sodium sulfate and concentration in vacuo gave a yellow oil. The oil was taken up in THF (15 mL) and lithium hydroxide (280.86 mg; 11.73 mmol; 5 eq.) was added, followed by water (15 mL). The reaction mixture was then stirred at room temperature for 5 hours. THF was evaporated and the residue diluted with water. The aqueous phase was washed with Et$_2$O and acidified to pH 5 with acetic acid. Extraction with Et$_2$O followed by drying over magnesium sulfate and concentration in vacuo afforded the title compound (562 mg, 96%) as a yellow solid.

HPLC (Method A): Rt 3.69 min (purity 99.7%). LC/MS: 250.9 (M−H)$^-$, 252.9 (M+H)$^+$. $^1$H NMR (DMSO-d$_6$, 300 MHz) δ 13.01 (1H, s), 8.23 (1H, s), 7.96 (1H, d, J=8.3 Hz), 7.29 (1H, d, J=8.3 Hz), 3.09 (4H, s), 1.58 (6H, s).

Intermediate 5: 4-Morpholin-4-yl-3-nitrobenzoic acid

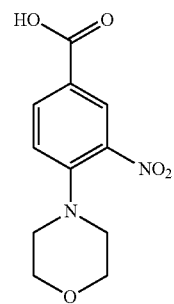 [SMILES: O=C(O)c1ccc(N2CCOCC2)c([N+](=O)[O-])c1]

A mixture of ethyl 4-fluoro-3-nitrobenzoate (Chontech 01072; 500 mg; 2.35 mmol; 1 eq.) and morpholine (Fluka 69880; 613.06 mg; 7.04 mmol; 3 eq.) in DMF (2 mL) was stirred at 50° C. for 3 hours. The reaction was then allowed to return to room temperature and diluted with water. Extraction with ethyl acetate, drying over sodium sulfate and concentration in vacuo gave a yellow oil. The latter was taken up in THF (15 mL) and lithium hydroxide (280.86 mg; 11.73 mmol; 5 eq.) was added followed by water (15 mL). The reaction mixture was stirred at room temperature for 5 hours. The THF was evaporated and the residue diluted with water. The aqueous phase was washed with Et$_2$O and acidified to pH 5 with acetic acid. Extraction with Et$_2$O followed by drying over magnesium sulfate and concentration in vacuo afforded the title compound (548 mg, 93%) as a yellow solid.

$^1$H NMR (DMSO-d$_6$, 300 MHz) δ 13.12 (1H, s), 8.27 (1H, s), 8.02 (1H, d, J=8.3 Hz), 7.32 (1H, d, J=8.3 Hz), 3.72-3.65 (4H, m), 3.16-3.10 (4H, m).

Intermediate 6: 4-Piperidin-1-ylbenzoic acid

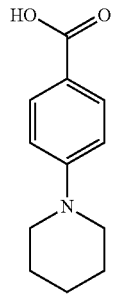

A mixture of methyl 4-fluorobenzoate (Lancaster 14154; 500 mg; 3.24 mmol; 1 eq.) and piperidine (Fluka 80640; 828.62 mg; 9.73 mmol; 3 eq.) in DMF (2 mL) was stirred at 50° C. for 16 hours. The reaction mixture was then passed through a short pad of silica and the obtained solution evaporated in vacuo to give a colourless oil. The oil was taken up in THF (15 mL) and lithium hydroxide (388.41 mg; 16.22 mmol; 5 eq.) was added followed by water (15 mL). The reaction mixture was stirred at room temperature for 6 hours then at 60° C. for 16 hours. NaOH (155.5 mg, 6.48 mmol, 2 eq) was then added and the reaction mixture was refluxed for 24 hours. After cooling, the solution was diluted with water and washed with Et$_2$O. The aqueous layer was then acidified to pH 5-6 with acetic acid and the formed precipitate was collected by filtration, washed with water and dried under high vacuum to afford the title compound as a white solid.

HPLC (Method A): Rt 1.43 min (purity 93.9%). LC/MS: 205.9 (M+H)$^+$, 203.9 (M–H)$^-$.

Intermediate 7:
4-[Cyclohexyl(methyl)amino]-3-nitrobenzoic acid

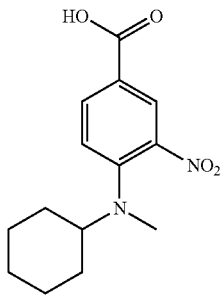 [SMILES: CN(c1ccc(C(=O)O)cc1[N+](=O)[O-])C1CCCCC1]

A mixture of ethyl 4-fluoro-3-nitrobenzoate (Chontech 01072; 500 mg; 2.35 mmol; 1 eq.) and N-methylcyclohexylamine (Aldrich 10, 332-2; 796.59 mg; 7.04 mmol; 3 eq.) in DMF (2 mL) was stirred at 50° C. for 3 hours. The reaction was then allowed to return to room temperature and diluted with water. Extraction with ethyl acetate, drying over sodium sulfate and concentration in vacuo gave a yellow oil. The oil was taken up in THF (15 mL) and lithium hydroxide (280.86 mg; 11.73 mmol; 5 eq.) was added followed by water (15 mL). The reaction mixture was stirred at room temperature for 5 hours. After evaporation of the solvent, the solution was diluted with water and washed with Et$_2$O. The aqueous layer was acidified to pH 4 with AcOH, extracted with Et$_2$O, dried over magnesium sulfate and concentrated in vacuo to afford the title compound as a yellow solid.

HPLC (Method A): Rt 4.42 min (purity 98.3%). LC/MS: 277.0 (M–H)$^-$.

Intermediate 8:
4-(2-Methylpiperidin-1-yl)-3-nitrobenzoic acid

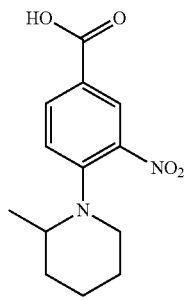 [SMILES: CC1CCCCN1c1ccc(C(=O)O)cc1[N+](=O)[O-]]

A mixture of ethyl 4-fluoro-3-nitrobenzoate (Chontech 01072; 1.00 g; 4.69 mmol; 1 eq.) and 2-methylpiperidine (Aldrich M7, 280-3; 1.396 g; 14.07 mmol; 3 eq.) in DMF (4 mL) was stirred at 50° C. for 3 hours. The reaction was then allowed to return to room temperature and diluted with water. Extraction with ethyl acetate, drying over sodium sulfate and concentration in vacuo gave a yellow oil. The oil was taken up in THF (10 mL) and lithium hydroxide (561.73 mg; 23.46 mmol; 5 eq.) was added followed by water (10 mL). The reaction mixture was stirred at room temperature for 16 hours. After evaporation of the THF, the solution was diluted with water and washed with Et$_2$O. The aqueous layer was acidified to pH 5 with AcOH, extracted with Et$_2$O, dried over magnesium sulfate and concentrated in vacuo to afford the title compound (1.17 g, 94%) as a yellow solid.

LC/MS: 265.0 (M+H)$^+$, 263.0 (M–H)$^-$. $^1$H NMR: (DMSO-d$_6$, 300 MHz) δ 13.07 (s, 1H), 8.23 (d, J=2.1 Hz, 1H), 8.02 (dd, J=9.0, 2.3 Hz, 1H), 7.44-7.41 (d, J=8.9 Hz, 1H), 3.64-3.60 (m, 1H), 3.25-3.17 (m, 1H), 2.90-2.84 (m, 1H), 1.82-1.43 (m, 6H), 1.05 (d, J=6.4 Hz, 3H).

Intermediate 9:
4-(3,3-Difluoropiperidin-1-yl)-3-nitrobenzoic acid

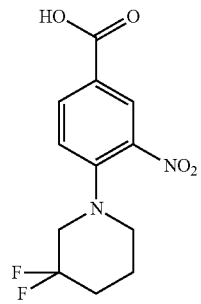 [SMILES: O=C(O)c1ccc(N2CCCC(F)(F)C2)c([N+](=O)[O-])c1]

A mixture of ethyl 4-fluoro-3-nitrobenzoate (Chontech 01072; 500 mg; 2.35 mmol; 1 eq.), 3,3-difluoropiperidine hydrochloride (Aldrich 665517; 554.47 mg; 3.52 mmol; 1.5 eq.) and triethylamine (712.07 mg; 7.04 mmol; 3 eq.) in DMF (3 mL) was stirred at 60° C. for 4 hours. The reaction mixture was then partitioned between ethyl acetate and aq. NH$_4$Cl. The organic layer was washed three times with aq. NH$_4$Cl then brine, dried over magnesium sulfate and concentrated in vacuo to give a yellow oil. The oil was taken up in THF (15 mL) and lithium hydroxide (280.86 mg; 11.73 mmol; 5 eq.) then water (15 mL) were added. The reaction mixture was stirred at room temperature for 4 hours and the THF was evaporated under vacuum. The resulting solution was washed with Et$_2$O, acidified with acetic acid and extracted twice with Et$_2$O. The combined organic layer was dried over magnesium sulfate and concentrated in vacuo to give a yellow oil which was crystallized from water. Filtration and drying under high vacuum afforded the title compound (630 mg, 94%) as a yellow solid.

HPLC (Method A): Rt 3.61 min (purity 99.4%). LC/MS: 286.9 (M+H)$^+$, 284.9 (M–H)$^-$.

Intermediate 10: 3-Nitro-4-pyrrolidin-1-ylbenzoic acid

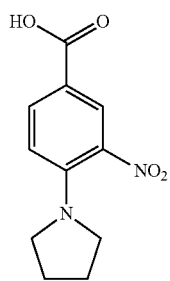

A mixture of ethyl 4-fluoro-3-nitrobenzoate (Chontech 01072; 500 mg; 2.35 mmol; 1 eq.) and pyrrolidine (Fluka 83240; 500.48 mg; 7.04 mmol; 3 eq.) in DMF (2 mL) was stirred at 60° C. for 4 hours. The reaction mixture was then partitioned between ethyl acetate and aq. NH$_4$Cl. The organic layer was washed three times with aq. NH$_4$Cl then brine, dried over magnesium sulfate and concentrated in vacuo to give a yellow oil. The latter was taken up in THF (5 mL) and lithium hydroxide (280.86 mg; 11.73 mmol; 5 eq.) then water (5 mL) were added. The reaction mixture was stirred at room temperature for 16 hours then the THF was evaporated and the residue was diluted with water. After acidification with AcOH, the formed precipitate was filtered and dried under high vacuum to afford the title compound (497 mg, 90%) as a yellow solid.

HPLC (Method A): Rt 3.75 min (purity 99.0%). LC/MS: 236.8 (M+H)$^+$, 234.9 (M–H)$^-$.

Intermediate 11: 4-Azepan-1-yl-3-nitrobenzoic acid

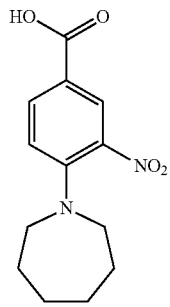

A mixture of ethyl 4-fluoro-3-nitrobenzoate (Chontech 01072; 500 mg; 2.35 mmol; 1 eq.) and hexamethyleneimine (Fluka 52660; 697.89 mg; 7.04 mmol; 3 eq.) in DMF (2 mL) was stirred at 60° C. for 4 hours. The reaction mixture was then partitioned between ethyl acetate and aq. NH$_4$Cl. The organic layer was washed with brine, dried over magnesium sulfate and concentrated in vacuo to give a yellow solid. The latter was taken up in THF (5 mL) and lithium hydroxide (280.86 mg; 11.73 mmol; 5 eq.) then water (5 mL) were added. The reaction mixture was stirred at room temperature for 16 hours then the solvent was evaporated and the residue was diluted with water. After acidification to pH 5 with AcOH, the resulting precipitate was filtered and dried under high vacuum to afford the title compound (534 mg, 86%) as a yellow solid.

HPLC (Method A): Rt 3.16 min (purity 99.4%). LC/MS: 264.9 (M+H)$^+$, 262.9 (M–H)$^-$.

Intermediate 12: 4-Morpholin-4-yl-3-(trifluoromethyl)benzonitrile

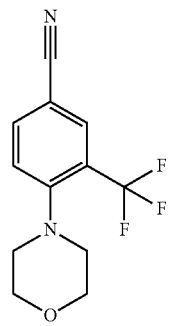 [SMILES: N#Cc1ccc(N2CCOCC2)c(C(F)(F)F)c1]

A mixture of 4-fluoro-3-trifluoro-methylbenzonitrile (Fluorochem 2223; 10 g; 52.8 mmol; 1 eq.) and morpholine (Fluka 69880; 9.25 mL; 105.7 mmol; 2 eq.) was stirred at 60° C. for 8 hours. The mixture was cooled and diluted with water. The precipitate was filtered and dried to afford the title compound (12.9 g, 95%) as a white solid.

HPLC (Method B): Rt 3.61 min (purity 99.1%). LC/MS: 257.1 (M+H)$^+$. $^1$H NMR (CDCl$_3$, 400 MHz) δ 7.92 (1H, s), 7.78-7.81 (1H, d), 7.32-7.35 (1H, d), 3.84-3.87 (4H, m), 3.04-3.06 (4H, m).

Intermediate 13: Methyl 4-morpholin-4-yl-3-(trifluoromethyl)benzoate

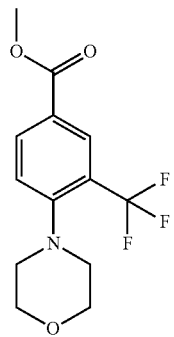 [SMILES: COC(=O)c1ccc(N2CCOCC2)c(C(F)(F)F)c1]

A mixture of intermediate 12 (5 g, 19.5 mmol; 1 eq.) and HCl in Methanol (250 mL) was stirred at 60° C. for 24 hours. The reaction mixture was evaporated to dryness and the residue partitioned between ethyl acetate and 10% aq. NaHCO$_3$. The separated organic layer was washed successively with water and brine, dried over magnesium sulfate and concentrated in vacuo to afford the title compound (4.45 g, 97%) as a yellow oil.

¹H NMR (CDCl₃, 400 MHz) δ 8.32 (1H, s), 8.17-8.19 (1H, d), 7.31-7.33 (1H, d), 3.94 (1H, s), 3.85-3.89 (4H, m), 3.02-3.07 (4H, m).

Intermediate 14: 4-Morpholin-4-yl-3-(trifluoromethyl)benzoic acid

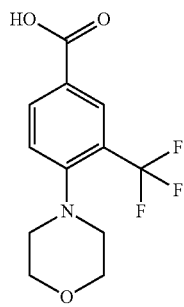 [SMILES: O=C(O)c1ccc(N2CCOCC2)c(C(F)(F)F)c1]

To a solution of intermediate 13 (5 g; 17.2 mmol; 1 eq.) in THF (50 mL) and water (5 mL) was added lithium hydroxide (1.5 g; 34.4 mmol; 2 eq.) and the reaction mixture was stirred at room temperature for 12 hours. The solvent was evaporated in vacuo and the residue diluted with water. This solution was washed with dichloromethane, acidified to pH 4 with conc. HCl and extracted with ethyl acetate. The organic layer was washed with brine, dried over sodium sulfate and evaporated in vacuo to afford the title compound as a white solid.

HPLC (Method B): Rt 2.97 min (purity 99.7%). LC/MS: 275.9 (M+H)⁺. ¹H NMR (DMSO-d₆, 400 MHz) δ 13.5 (1H, bs), 8.13-8.16 (2H, m), 7.55-7.57 (1H, d), 3.69-3.71 (4H, m), 2.94-2.96 (4H, m).

Intermediate 15: Methyl 2,2'-dimethyl-1,1'-biphenyl-4-carboxylate

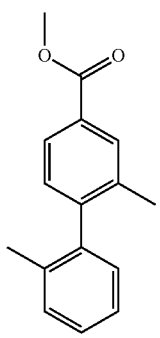

A suspension of methyl 4-bromo-3-methylbenzoate (ABCR AV19078; 15 g; 65.48 mmol; 1 eq.), o-tolylboronic acid (Aldrich 393606; 10.68 g; 78.5 mmol; 1.2 eq.), potassium carbonate (45.25 g, 327.4 mmol, 5 eq.) and tetrakis(triphenylphosphine)palladium(0) (3.78 g; 3.27 mmol; 0.05 eq.) in toluene (200 mL) and water (200 mL) was stirred at 120° C. for 6 hours. The resulting mixture was allowed to return to room temperature and the two phases were separated. The organic layer was concentrated in vacuo and purified by column chromatography (c-hexane) to afford the title compound (15 g, 95%) as a white solid.

HPLC (Method B): Rt 3.01 min (purity 98.7%). ¹H NMR (DMSO-d₆, 400 MHz) δ 7.91 (1H, s), 7.83-7.81 (1H, m), 7.33-7.30 (2H, m), 7.28-7.26 (1H, m), 7.25-7.22 (1H, m), 7.07-7.05 (1H, d), 3.86-3.81 (3H, s), 2.09-2.00 (3H, s), 1.97-1.92 (3H, s).

Intermediate 16: 2,2'-Dimethyl-1,1'-biphenyl-4-carboxylic acid

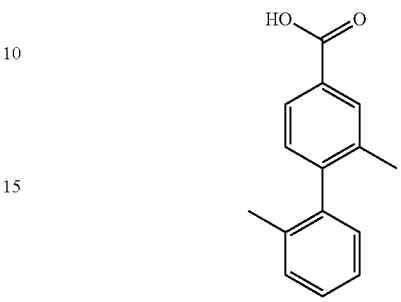

Sodium hydroxide (10% in water; 10 mL) was added to a solution of intermediate 15 (15 g, 62.24 mmol; 1 eq.) in THF (100 mL) and the reaction mixture was stirred at 70° C. for 16 hours. The solvent was evaporated in vacuo and the aqueous residue washed with ethyl acetate. The aqueous layer was then acidified pH 2-3 with 3M HCl and extracted with dichloromethane. The organic layer was washed with water, dried over sodium sulfate and concentrated in vacuo to afford the title compound (13.5 g, 95%) as a white solid.

HPLC (Method B): Rt 4.10 min (purity 99.6%). LC/MS: 227.0 (M+H)⁺. ¹H NMR (DMSO, 400 MHz) δ 12.89 (1H, bs), 7.89 (1H, s), 7.82-7.80 (1H, d), 7.32-7.23 (3H, m), 7.19-7.11 (1H, d), 7.07-7.05 (1H, d), 2.04 (3H, s), 1.98 (3H, s).

Intermediate 17: Methyl 2-methyl-2'-(trifluoromethyl)biphenyl-4-carboxylate

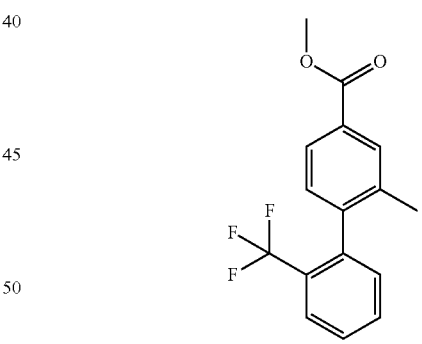

A suspension of methyl 4-bromo-3-methylbenzoate (ABCR AV19078; 3 g; 13.10 mmol; 1 eq.), 2-(trifluoromethyl)phenylboronic acid (Aldrich 393606; 2.74 g; 14.41 mmol; 1.10 eq.), potassium carbonate (9.05 g; 65.48 mmol; 5 eq.) and tetrakis(triphenylphosphine)palladium(0) (1.51 g; 1.31 mmol; 0.10 eq.) in toluene (15 mL) and water (15 mL) was refluxed for 3 hours. The resulting mixture was filtered through a short pad of Celite, which was further washed with toluene. After evaporation of the solvent, the residue was taken up in ethyl acetate and washed successively with sat. aq. NaHCO₃, water and brine, dried over magnesium sulfate and concentrated in vacuo to afford the title compound (3.7 g, 96%) as a brown oil.

HPLC (Method A): Rt 5.34 min (purity 70.9%). LC/MS: 294.9 (M+H)+.

Intermediate 18: 2-Methyl-2'-(trifluoromethyl)biphenyl-4-carboxylic acid

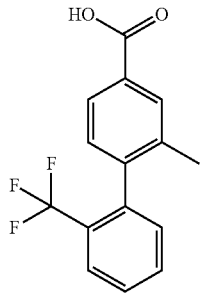 [SMILES: Cc1cc(C(=O)O)ccc1-c1ccccc1C(F)(F)F]

Sodium hydroxide (6.12 mL; 5M; 30.58 mmol; 3 eq.) was added to a solution of intermediate 17 (3 g; 10.19 mmol; 1 eq.) in EtOH (90 mL) and the resulting mixture was stirred at 60° C. for 1 hour. After evaporation of the solvent, the residue was taken up in water and washed with ethyl acetate. The aqueous phase was acidified to pH 2 with conc. HCl and the obtained solution was concentrated in vacuo until crystallization. The solid was collected by filtration and dried under high vacuum to afford the title compound (2.41 g, 84%) as a beige solid.

HPLC (Method A): Rt 4.49 min (purity 95.7%). LC/MS: 279.0 (M−H)−. $^1$H NMR (DMSO-$d_6$, 300 MHz) δ 13.03 (s, 1H), 7.91-7.68 (m, 5H), 7.38-7.36 (d, J=8.3 Hz, 1H), 7.27-7.25 (d, J=8.2 Hz, 1H), 2.05 (s, 3H).

Intermediate 19: Methyl 3-methyl-4-(4-methyl-3-thienyl)benzoate

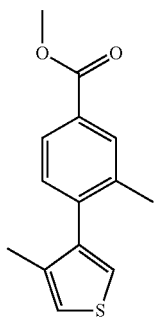

A suspension of methyl 4-bromo-3-methylbenzoate (ABCR AV19078; 3 g; 13.10 mmol; 1 eq.), 4-methyl-3-thiopheneboronic acid (Aldrich 542393; 2.05 g; 14.41 mmol; 1.10 eq.), potassium carbonate (9.05 g; 65.48 mmol; 5 eq.) and tetrakis(triphenylphosphine)palladium(0) (1.51 g; 1.31 mmol; 0.10 eq.) in toluene (15 mL) and water (15 mL) was refluxed for 3 hours. The resulting mixture was filtered through a short pad of Celite, which was further washed with toluene. After evaporation of the solvent, the residue taken up in ethyl acetate and washed successively with sat. aq. NaHCO$_3$, water and brine, dried over magnesium sulfate and concentrated in vacuo to afford the title compound (2.96 g, 92%) as a brown oil.

HPLC (Method A): Rt 5.14 min (purity 58.3%). LC/MS: 246.8 (M+H)+.

Intermediate 20: 3-Methyl-4-(4-methyl-3-thienyl)benzoic acid

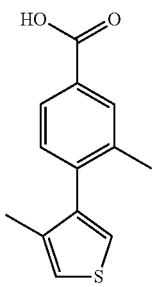

Sodium hydroxide (4.87 mL; 5M; 24.36 mmol; 3 eq.) was added to a solution of intermediate 19 (2 g; 8.12 mmol; 1 eq.) in EtOH (60 mL) and the resulting mixture was stirred at 60° C. for 2 hours. After evaporation of the solvent, the residue was taken up in water and washed with ethyl acetate. The aqueous phase was acidified to pH 2 with conc. HCl and the obtained solution was concentrated in vacuo until crystallization. The solid was collected by filtration and dried under high vacuum to afford the title compound as a beige solid.

HPLC (Method A): Rt 4.26 min (purity 99.6%). LC/MS: 232.9 (M+H)+, 231.0 (M−H)−. $^1$H NMR: (DMSO-$d_6$, 300 MHz) δ 12.97 (s, 1H), 7.91 (s, 1H), 7.84-7.81 (dd, J=8.1 Hz, J=1.9 Hz; 1H), 7.41 (d, J=3.2 Hz, 1H), 7.35-7.34 (m, 1H), 7.28-7.26 (d, J=7.8 Hz, 1H), 2.18 (s, 3H), 2.00 (s, 3H).

Intermediate 21: Methyl 2'-methyl-2-nitro-1,1'-biphenyl-4-carboxylate

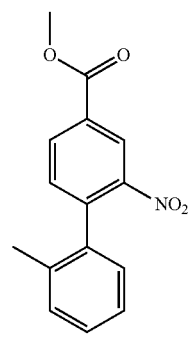 [SMILES: COC(=O)c1ccc(-c2ccccc2C)c([N+](=O)[O-])c1]

A suspension of methyl 4-bromo-3-nitrobenzoate (Chess 1687; 3 g; 11.53 mmol; 1 eq.), o-tolylboronic acid (Aldrich 393606; 1.88 g; 13.84 mmol; 1.2 eq.), potassium carbonate (7.97 g, 57.68 mmol, 5 eq.) and tetrakis(triphenylphosphine)palladium(0) (668.2 mg, 0.577 mmol, 0.05 eq.) in toluene (15 mL) and water (15 mL) was stirred at 120° C. for 14 hours. The resulting mixture was allowed to return to room temperature and the two phases were separated. The organic layer was concentrated in vacuo and purified by column chromatography (c-hexane) to afford the title compound (2.5 g, 79%) as a white solid.

¹H NMR (DMSO-d₆, 400 MHz) δ 8.52 (1H, s), 8.29-8.26 (1H, m), 7.63-7.61 (1H, m), 7.34-7.33 (2H, m), 7.23 (1H, m), 7.13 (1H, m), 3.94 (3H, s), 2.04 (3H, s).

Intermediate 22: 2'-Methyl-2-nitro-1,1'-biphenyl-4-carboxylic acid

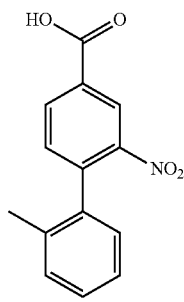 [SMILES: Cc1ccccc1-c1ccc(C(=O)O)cc1[N+](=O)[O-]]

Lithium hydroxide (1.15 g, 27.6 mmol, 3 eq.) was added to a solution of intermediate 21 (2.5 g, 9.2 mmol, 1 eq.) in THF (20 mL) and water (5 mL) and the reaction mixture was stirred at room temperature for 4 hours. The solvent was evaporated in vacuo and the aqueous residue washed with ethyl acetate. The aqueous layer was then acidified pH 2-3 with 1.5M HCl and extracted with dichloromethane. The organic layer was washed with water, dried over sodium sulfate and concentrated in vacuo to afford the title compound (1.6 g, 70%) as a yellow solid.

HPLC (Method B): Rt 3.70 min (purity 99.9%). LCMS: 255.9 (M–H)⁻. ¹H NMR (DMSO-d₆, 400 MHz) δ 13.67 (1H, bs), 8.49 (1H, s), 8.26-8.24 (1H, d), 7.58-7.56 (1H, m), 7.35-7.32 (2H, m), 7.27-7.12 (1H, d), 7.10 (1H, d), 2.09-1.99 (3H, s).

Intermediate 23: 5-fluoro-N'-hydroxy-2-methoxy-benzenecarboximidamide

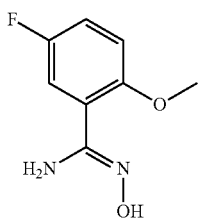

Hydroxylamine (4.97 ml; 82.7 mmol; 5 eq.) was added to a suspension of 5-fluoro-2-methoxybenzonitrile (Aldrich 527734; 2.5 g; 16.5 mmol; 1 eq.) in EtOH (30 mL) and the resulting mixture was stirred at room temperature for 3 days then to dryness to afford the title compound (3.04 g, 100%) as a white solid.

¹H NMR (DMSO-d₆, 300 MHz) δ 9.53 (s, 1H), 7.25-7.15 (m, 2H), 7.11-7.03 (m, 1H), 5.69 (s, 2H), 3.78 (s, 3H).

Intermediate 24: 4-(2-Methylpiperidin-1-yl)-3-(trifluoromethyl)benzoic acid

Step 1: 4-(2-Methylpiperidin-1-yl)-3-(trifluoromethyl)benzonitrile

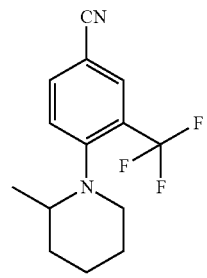 [SMILES: CC1CCCCN1c1ccc(C#N)cc1C(F)(F)F]

A mixture of 4-fluoro 3-trifluoro-methylbenzonitrile (ABCR F043738; 25 g; 132 mmol; 1 eq.) and 2-methylpiperidine (30.3 mL; 264 mmol; 2 eq.) was stirred at 100° C. 12 hours. The reaction mixture was cooled, diluted with water (200 mL) and extracted with ethyl acetate (2×200 mL). The combined organic layer was washed with water (100 mL) and brine (100 mL), dried over sodium sulphate and concentrated in vacuo. The residue was purified by column chromatography (petroleum ether/ethyl acetate, 80/20) to afford the title compound of the title compound as an off-white solid.

LC/MS: 269 (M+H)⁺. ¹H NMR (DMSO-d₆, 400 MHz) δ 8.19 (s, 1H), 8.18-8.15 (m, 1H), 7.90-7.80 (m, 1H), 3.19-3.15 (m, 1H), 2.90-2.85 (m, 1H), 2.71-2.60 (m, 1H), 1.81-1.75 (m, 2H), 1.60-1.31 (m, 3H), 1.31-1.21 (m, 1H), 0.70 (d, J=6.4 Hz, 3H).

Step 2: Methyl 4-(2-methylpiperidin-1-yl)-3-(trifluoromethyl)benzoate. Hydrochloride salt

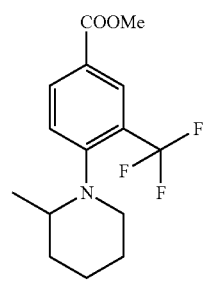 [SMILES: COC(=O)c1ccc(N2CCCCC2C)c(C(F)(F)F)c1]

A mixture of 4-(2-methylpiperidin-1-yl)-3-(trifluoromethyl)benzonitrile (21 g, 78.4 mmol) and HCl in methanol (4M, 500 mL) was stirred at 80° C. for 20 hours, then concentrated to dryness to afford the title compound (25 g, 96%) as a beige solid.

LC/MS: 301.9 (M+H)⁺. ¹H NMR (DMSO-d₆, 400 MHz) δ 8.20-8.18 (m, 2H), 7.69-7.62 (m, 1H), 3.89 (s, 3H), 3.20-3.12

(m, 1H), 2.90-2.85 (m, 1H), 2.60-2.50 (m, 1H), 1.85-1.79 (m, 2H), 1.69-1.65 (m, 2H), 1.51-1.45 (m, 1H), 1.31-1.23 (m, 1H), 0.75 (d, J=6.4 Hz, 3H).

Step 3: 4-(2-methylpiperidin-1-yl)-3-(trifluoromethyl)benzoic acid

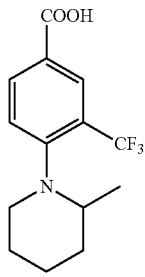

A solution of methyl 4-(2-methylpiperidin-1-yl)-3-(trifluoromethyl)benzoate. Hydrochloride salt (25 g, 74 mmol) in HCl 4M (200 mL) was stirred at 100° C. for 16 hours. After cooling to room temperature, the precipitate was filtered off and dried under vacuum to afford the title compound (18 g, 85%) of as a white solid.

HPLC (Method B): Rt 5.53 min (purity 98.3%). LC/MS: 287.9 (M+H)$^+$. $^1$H NMR (DMSO-d$_6$, 400 MHz) δ 13.30 (s, 1H), 8.19-8.15 (m, 2H), 7.70-7.67 (m, 1H), 3.08-3.06 (m, 1H), 2.89-2.86 (m, 1H), 2.60-2.49 (m, 1H), 1.90-1.89 (m, 2H), 1.76-1.74 (m, 2H), 1.46-1.43 (m, 1H), 1.41-1.40 (m, 1H), 0.77 (d, J=6.4 Hz, 3H).

Intermediate 25:
4-(2,5-dimethylpyrrolidin-1-yl)-3-nitrobenzoic acid

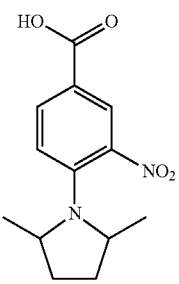 [SMILES: CC1CCC(C)N1c1ccc(C(=O)O)cc1[N+](=O)[O-]]

A mixture of 4-fluoro-3-nitrobenzoic acid (300 mg; 1.62 mmol; 1 eq.) and 2,5-dimethylpyrrolidine (Maybridge AC11676DA; 0.70 mL; 5.72 mmol; 3.53 eq.) was stirred at 100° C. for 5 minutes in the MW. The solution was concentrated in vacuo and the residue taken up in water (100 mL). The aqueous phase was washed with diethyl ether (2×20 mL) then acidified to pH 5 with acetic acid. Extraction with diethyl ether (150 mL), drying over magnesium sulfate and concentration in vacuo afforded the title compound (360 mg, 84%) as an orange solid.

HPLC (Method A): Rt 3.82 min (purity 100%). LC/MS: 264.9 (M+H)$^+$.

Intermediate 26:
2'-methoxy-2-methylbiphenyl-4-carboxylic acid

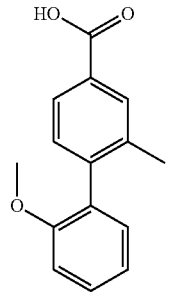 [SMILES: COc1ccccc1-c1ccc(C(=O)O)cc1C]

Step 1: methyl 2'-methoxy-2-methylbiphenyl-4-carboxylate

A suspension of methyl 4-bromo-3-methylbenzoate (4.9 g; 21.4 mmol; 1 eq.), 2-methoxyphenylboronic acid (Aldrich 44, 523-1; 3.6 g; 23.5 mmol; 1.1 eq.), potassium carbonate (14.8 g; 107 mmol; 5 eq.) and Pd(PPh$_3$)$_4$ (2.47 g; 2.14 mmol; 0.1 eq.) in toluene (24.5 mL) and water (24.5 mL) was refluxed for 6 hours. The reaction mixture was cooled down to room temperature and filtered through a pad of CELITE which was further washed with toluene (500 mL). The filtrate was concentrated in vacuo and the residue taken up in ethyl acetate (500 mL). The organic layer was washed with sat. aq. NaHCO$_3$ (200 mL), water (200 mL) and brine (200 mL) then dried over magnesium sulfate and concentrated in vacuo. The crude was purified by column chromatography (c-hexane/ethyl acetate, 90/10) to afford the title compound (4.38 g, 80%) as a colorless oil. HPLC (Method A): Rt 4.85 min (purity 98.9%). LC/MS: 257.0 (M+H)$^+$.

Step 2: 2'-methoxy-2-methylbiphenyl-4-carboxylic acid

Sodium hydroxide (5M; 4.7 mL; 23.4 mmol; 3 eq.) was added to a solution of methyl 2'-methoxy-2-methylbiphenyl-4-carboxylate (2 g; 7.8 mmol; 1 eq.) in EtOH (60 mL) and the reaction mixture was stirred at 60° C. for one hour then concentrated in vacuo. The residue was taken up in water (400 mL) and washed with ethyl acetate (2×200 mL) then acidified to pH 2 with conc. HCl. The solution was concentrated to ca. 80 mL, the precipitate filtered off and dried to afford the title compound as a brown solid.

HPLC (Method A): Rt 4.05 min (purity 98.5%). LC/MS: 240.9 (M−H)⁻.

Intermediate 27:
2-methoxy-2'-methylbiphenyl-4-carboxylic acid

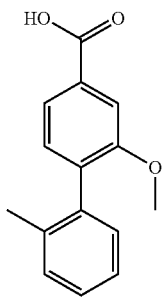

A suspension of methyl 4-bromo-3-methoxybenzoate (Combi-blocks CA-4192; 2.5 g; 10.2 mmol; 1 eq.), o-tolylboronic acid (Aldrich 393606; 1.53 g; 11.2 mmol; 1.1 eq.), potassium carbonate (7.05 g; 51 mmol; 5 eq.) and Pd(PPh$_3$)$_4$ (1.18 g; 1.02 mmol; 0.1 eq.) in toluene (12.5 mL) and water (12.5 mL) was refluxed for 2 hours. The reaction mixture was cooled down to room temperature and filtered through a pad of CELITE which was further washed with toluene (200 mL). The filtrate was concentrated in vacuo and the residue taken up in Ethyl acetate (500 mL). The organic layer was washed with sat. aq. NaHCO$_3$ (150 mL), water (150 mL) and brine (150 mL) then dried over magnesium sulfate and concentrated in vacuo. The residue (2.5 g; 9.75 mmol; 1 eq.) was taken up in EtOH (75 mL), sodium hydroxide (5M; 5.85 mL; 29.3 mmol; 3 eq.) was added and the reaction mixture was stirred at 60° C. for two hours. After concentration in vacuo, the residue was taken up in water (400 mL) and the aqueous phase was washed with Ethyl acetate then acidified to pH 2 with conc. HCl. The solution was concentrated to ca. 80 mL and the precipitate filtered off and dried to afford the title compound (1.95 g, 79%) as a beige solid.

HPLC (Method A): Rt 4.05 min (purity 97.3%). LC/MS: 240.9 (M−H)⁻.

Intermediate 28: 2',4'-dimethoxy-2-methylbiphenyl-4-carboxylic acid

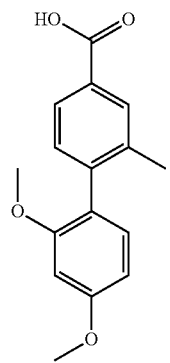 [SMILES: COc1ccc(-c2ccc(C(=O)O)cc2C)c(OC)c1]

A suspension of methyl 4-bromo-3-methylbenzoate (3.0 g; 13.1 mmol; 1 eq.), 2,4-dimethoxyphenylboronic acid (Aldrich 483486; 2.62 g; 14.4 mmol; 1.1 eq.), potassium carbonate (9.05 g; 65.5 mmol; 5 eq.) and Pd(PPh$_3$)$_4$ (1.51 g; 1.31 mmol; 0.1 eq.) in toluene (15 mL) and water (15 mL) was refluxed for 6 hours. The reaction mixture was cooled down to room temperature and filtered through a pad of CELITE which was further washed with toluene (200 mL). The filtrate was concentrated in vacuo and the residue taken up in Ethyl acetate (300 mL). The organic layer was washed with sat. aq. NaHCO$_3$ (100 mL), water (100 mL) and brine (100 mL) then dried over magnesium sulfate and concentrated in vacuo. The residue (2.0 g; 6.99 mmol; 1 eq.) was taken up in EtOH (60 mL), sodium hydroxide (5M; 4.19 mL; 21 mmol; 3 eq.) was added and the reaction mixture was stirred at 60° C. for one hour. After concentration in vacuo, the residue was taken up in water (400 mL) and the aqueous phase was washed with Ethyl acetate then acidified to pH 2 with conc. HCl. The solution was concentrated to ca. 80 mL and the precipitate filtered off and dried to afford the title compound as an orange solid.

HPLC (Method A): Rt 3.87 min (purity 99.7%). LC/MS: 270.9 (M−H)⁻.

Intermediate 29:
3-methoxy-4-(4-methyl-3-thienyl)benzoic acid

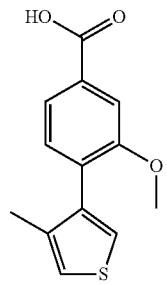

A suspension of methyl 4-bromo-3-methoxybenzoate (2.5 g; 10.2 mmol; 1.00 eq.), 4-methyl-3-thiopheneboronic acid (Aldrich 542393; 1.59 g; 11.2 mmol; 1.1 eq.), potassium carbonate (7.05 g; 51 mmol; 5 eq.) and Pd(PPh$_3$)$_4$ (1.18 g; 1 mmol; 0.1 eq.) in toluene (12.5 mL) and water (12.5 mL) was refluxed for 5 hours. The reaction mixture was cooled down to room temperature and filtered through a pad of CELITE which was further washed with toluene (200 mL). The filtrate was concentrated in vacuo and the residue taken up in Ethyl acetate (400 mL). The organic layer was washed with sat. aq. NaHCO$_3$ (100 mL), water (100 mL) and brine (100 mL) then dried over magnesium sulfate and concentrated in vacuo. The residue (2.3 g; 8.77 mmol; 1 eq.) was taken up in EtOH (69 mL), sodium hydroxide (5M; 5.26 mL; 26.3 mmol; 3 eq.) was added and the reaction mixture was stirred at 60° C. for one hour. After concentration in vacuo, the residue was taken up in water (200 mL) and the aqueous phase was washed with Ethyl acetate then acidified to pH 2 with conc. HCl. The solution was concentrated to ca. 100 mL and the precipitate filtered off and dried to afford the title compound (1.81 g, 71%) as a brown solid.

Intermediate 30: 4-(3,5-dimethylisoxazol-4-yl)-3-methylbenzoic acid

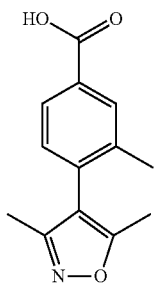

A suspension of methyl 4-bromo-3-methylbenzoate (4 g; 17.5 mmol; 1 eq.), 3,5-dimethyl-4-(4,4,5,5-tetramethyl-1,3,2-dioxaborolane-2-yl)isoxazole (Fluorochem 11035; 4.28 g; 19.2 mmol; 1.1 eq.), potassium carbonate (12.1 g; 87.3 mmol; 5 eq.) and Pd(PPh$_3$)$_4$ (2.02 g; 1.75 mmol; 0.1 eq.) in toluene (20 mL) and water (20 mL) was refluxed for 4 hours. The reaction mixture was cooled down to room temperature and filtered through a pad of CELITE which was further washed with toluene (200 mL). The filtrate was concentrated in vacuo and the residue taken up in Ethyl acetate (250 mL). The organic layer was washed with sat. aq. NaHCO$_3$ (100 mL), water (100 mL) and brine (100 mL) then dried over magnesium sulfate and concentrated in vacuo. The residue (3 g; 12.2 mmol; 1 eq.) was taken up in EtOH (90 mL), sodium hydroxide (5M; 7.34 mL; 36.7 mmol; 3 eq.) was added and the reaction mixture was stirred at 60° C. for one hour. After concentration in vacuo, the residue was taken up in water (200 mL) and the aqueous phase was washed with Ethyl acetate then acidified to pH 2 with conc. HCl. The solution was concentrated to ca. 100 mL and the precipitate filtered off and dried. Trituration in Et$_2$O and filtration afforded the title compound as a beige solid.

HPLC (Method A): Rt 3.13 min (purity 97.1%).

Intermediate 31: 4-[bis(2-methoxyethyl)amino]-3-nitrobenzoic acid

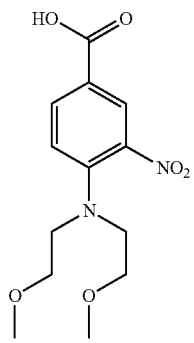 [SMILES: COCCN(CCOC)c1ccc(C(=O)O)cc1[N+](=O)[O-]]

Bis(2-methoxyethyl)amine (Aldrich B4, 820-7; 1.6 g; 12 mmol; 3 eq.) was added to a solution of 4-fluoro-3-nitrobenzoic acid (740 mg; 4 mmol; 1 eq.) in EtOH (20 mL) and the resulting mixture was stirred at room temperature for 2 hours then at 70° C. for 20 hours. The solution was concentrated in vacuo and the residue was partitioned between NaOH 0.5M and Et$_2$O. The aqueous layer was acidified to pH 2 with HCl 5M, extracted with ethyl acetate (3×) and the combined organic phase was dried over magnesium sulfate. After evaporation of the solvent, the residue was crystallised from ethyl acetate/n-pentane to afford the title compound (1.12 g, 94%) as a yellow solid.

$^1$H NMR (DMSO-d$_6$, 300 MHz) δ 12.95 (s, 1H), 8.17 (d, J=2.2 Hz, 1H), 7.93 (dd, J=8.9, 2.2 Hz, 1H), 7.39 (d, J=8.9 Hz, 1H) 3.50-3.36 (m, 8H), 3.18 (s, 6H).

Intermediate 32: 4-(4-methyl-3-thienyl)-3-(trifluoromethyl)benzoic acid

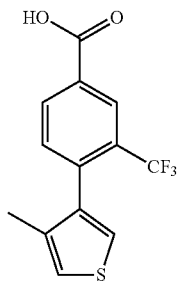 [SMILES: Cc1cscc1-c1ccc(C(=O)O)cc1C(F)(F)F]

Step 1: methyl 4-bromo-3-(trifluoromethyl)benzoate

Thionyl chloride (16.2 mL; 223 mmol; 4 eq.) was added to a suspension of 4-bromo-3-(trifluoromethyl)benzoic acid (15 g; 55.8 mmol; 1 eq.) in MeOH (300 mL) and the reaction mixture was stirred at room temperature for 16 hours.

The solvent was concentrated in vacuo and the residue was diluted with ethyl acetate (500 mL). The organic layer was washed with sat. aq. NaHCO$_3$ (200 mL), water (200 mL) and brine (200 mL) then dried over magnesium sulphate and concentrated in vacuo to afford the title compound (14.8 g, 94%) as an orange solid.

HPLC (Method A): Rt 4.71 min (purity 99.0%).

Step 2: methyl 4-(4-methyl-3-thienyl)-3-(trifluoromethyl)benzoate

A mixture of methyl 4-bromo-3-(trifluoromethyl)benzoate (3.5 g; 12.4 mmol; 1 eq.), 4-methyl-3-thiopheneboronic acid (1.93 g; 13.6 mmol; 1.1 eq.), potassium carbonate (8.54 g; 61.8 mmol; 5 eq.) and Pd(PPh$_3$)$_4$ (1.43 g; 1.24 mmol; 0.1 eq.) in toluene (17.5 mL) and water (17.5 mL) was refluxed for 24 h whereupon 4-methyl-3-thiopheneboronic acid (0.88 g; 6.2 mmol; 0.5 eq.) was added. The reaction mixture was stirred for a further 3 hours then cooled down to room temperature and filtered through a pad of CELITE which was washed with toluene (200 mL). The filtrate was concentrated in vacuo and the residue taken up in ethyl acetate (300 mL). The organic layer was washed with sat. aq. NaHCO$_3$ (100 mL), water (100 mL) and brine (100 mL), dried over magnesium sulphate and concentrated in vacuo to afford the title compound (3 g, 81%) as a brown oil.

HPLC (Method A): Rt 5.21 min (purity 68.1%).

Step 3: 4-(4-methyl-3-thienyl)-3-(trifluoromethyl)benzoic acid

Sodium hydroxide (5M: 6 mL; 30 mmol; 3 eq.) was added to a solution of methyl 4-(4-methyl-3-thienyl)-3-(trifluoromethyl)benzoate (3 g; 10 mmol; 1 eq.) in EtOH (90 mL) and the reaction mixture was stirred at 60° C. for 2 hours. After evaporation of the solvent, the residue was taken up in water (300 mL) and the aqueous phase was washed with ethyl acetate (2×100 mL) then acidified to pH 2 with conc. HCl. The solution was concentrated to ca. 100 mL and extracted with ethyl acetate. The organic layer was dried over magnesium sulphate and concentrated in vacuo to afford the title compound (2.6 g, 91%) as a brown oil.

HPLC (Method A): Rt 4.53 min (purity 95.5%). LC/MS: 284.9 (M−H)⁻.

Intermediate 33: 3-Methyl-4-piperidin-1-ylbenzoic acid

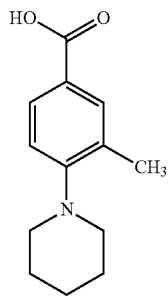

Step 1: Methyl 3-methyl-4-piperidin-1-ylbenzoate

BINAP (0.67 g; 1.1 mmol; 0.05 eq.) and palladium acetate (0.24 g; 1.1 mmol; 0.05 eq.) were added to a suspension methyl 4-bromo-3-methylbenzoate (5 g; 21.8 mmol; 1 eq.), $Cs_2CO_3$ (10.65 g; 32.7 mmol; 1.5 eq.) and piperidine (2.2 g; 26 mmol; 1.2 eq.) in dioxane (100 mL) and the reaction mixture was refluxed for 15 hours. After filtration through a pad of CELITE, the solution was concentrated in vacuo and the residue purified by column chromatography (petroleum ether/ethyl acetate, 80/20) to afford the title compound (4.9 g, 96%) as a brown solid.

LC/MS: 233.9 (M+H)⁺. ¹H NMR (CDCl₃, 400 MHz) δ 7.84-7.82 (m, 2H), 6.99-6.97 (m, 1H), 3.92 (s, 3H), 2.93-2.90 (m, 4H), 1.76-1.67 (m, 4H, m), 1.63-1.62 (m, 2H).

Step 2: 3-Methyl-4-piperidin-1-ylbenzoic acid

Lithium hydroxide (2.5 g; 103 mmol; 5 eq.) was added to a solution of methyl 3-methyl-4-piperidin-1-ylbenzoate (4.8 g; 20.6 mmol; 1 eq.) in THF (100 mL) and water (5 mL) and the reaction mixture was stirred at 50° C. for 12 hours. The solvent was removed in vacuo, the residue diluted with water and the aqueous layer washed with DCM (2×50 mL). The aqueous layer was acidified to pH 4 with conc. HCl and extracted with ethyl acetate (2×100 mL). The combined organic layer was washed with brine, dried over sodium sulfate and concentrated in vacuo to afford the title compound (4.0 g, 89%) as a yellow solid.

HPLC (Method B): Rt 5.47 min (purity 99.0%). LC/MS: 219.9 (M+H)⁺.

¹H NMR (DMSO-d₆, 400 MHz) δ 7.71-7.70 (m, 2H), 7.01-6.99 (m, 1H), 2.84-2.82 (m, 4H), 2.25 (s, 3H), 1.64-1.59 (m, 4H), 1.54-1.53 (m, 2H).

Intermediate 34: 2'-methyl-2-(trifluoromethyl)biphenyl-4-carboxylic acid

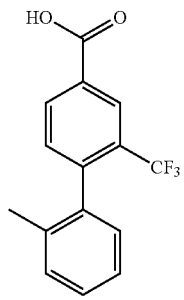 [SMILES: Cc1ccccc1-c1ccc(C(=O)O)cc1C(F)(F)F]

Step 1: methyl 2'-methyl-2-(trifluoromethyl)biphenyl-4-carboxylate

A mixture of methyl 4-bromo-3-(trifluoromethyl)benzoate (6 g; 21.2 mmol; 1 eq.), o-tolylboronic acid (3.17 g; 23.3 mmol; 1.1 eq.), potassium carbonate (14.65 g; 106 mmol; 5 eq.) and Pd(PPh₃)₄ (2.45 g; 2.12 mmol; 0.1 eq.) in toluene (30 mL) and water (30 mL) was refluxed for 3 hours. After cooling to room temperature, the reaction mixture was filtered through a pad of CELITE which was further washed with toluene (20 mL). The filtrate was concentrated in vacuo, the residue taken up in ethyl acetate (200 mL) and washed with sat. aq. NaHCO₃ (100 mL), water (100 mL) and brine (100 mL), dried over magnesium sulphate and concentrated in vacuo to afford the title compound (5 g, 80%) as a brown oil.

HPLC (Method A): Rt 5.33 min (purity 60.0%).

Step 2: 2'-methyl-2-(trifluoromethyl)biphenyl-4-carboxylic acid

Sodium hydroxide (5M; 10.2 mL; 51 mmol; 3 eq.) was added to a solution of methyl 2'-methyl-2-(trifluoromethyl)biphenyl-4-carboxylate (5 g; 17 mmol; 1 eq.) in EtOH (150 mL) and the reaction mixture was stirred at 60° C. for 2 hours. After concentration in vacuo, the residue was taken up in water (300 mL) and the aqueous phase was washed with ethyl acetate (2×100 mL). The pH was adjusted to 2 with conc. HCl and the solution was concentrated to ca. 150 mL. The precipitate was filtered off and dried to afford the title compound (3.33 g, 70%) as a beige solid.

HPLC (Method A): Rt 4.57 min (purity 98.7%). LC/MS: 278.9 (M−H)−.

Intermediate 35: 3-Methyl-4-morpholin-4-ylbenzoic acid

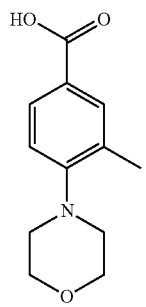

Step 1: Methyl 3-methyl-4-morpholin-4-ylbenzoate

BINAP (0.67 g; 1.1 mmol; 0.05 eq.) and palladium acetate (0.24 g; 1.1 mmol; 0.05 eq.) were added to a suspension methyl 4-bromo-3-methylbenzoate (5 g; 21.8 mmol; 1 eq.), $Cs_2CO_3$ (10.65 g; 32.7 mmol; 1.5 eq.) and morpholine (2.3 g; 26 mmol; 1.2 eq.) in dioxane (100 mL) and the reaction mixture was refluxed for 15 hours. After filtration through a pad of CELITE, the solution was concentrated in vacuo and the residue purified by column chromatography (petroleum ether/ethyl acetate, 80/20) to afford the title compound (4.3 g, 84%) as a yellow solid.

LC/MS: 236.0 (M+H)+. $^1$H NMR (CDCl$_3$, 400 MHz) δ 7.90-7.86 (m, 2H), 7.16-7.13 (m, 1H), 4.00-3.98 (m, 4H), 3.91 (s, 3H), 3.12-3.10 (m, 4H), 2.45 (s, 3H).

Step 2: 3-Methyl-4-morpholin-4-ylbenzoic acid

Lithium hydroxide (2 g; 84.6 mmol; 5 eq.) was added to a solution of methyl 3-methyl-4-morpholin-4-ylbenzoate (4 g; 17 mmol; 1 eq.) in THF (100 mL) and water (5 mL) and the reaction mixture was stirred at 50° C. for 12 hours. The solvent was removed in vacuo, the residue diluted with water and the aqueous layer washed with DCM (2×50 mL). The aqueous layer was acidified to pH 4 with conc. HCl and extracted with ethyl acetate (2×100 mL). The combined organic layer was washed with brine, dried over sodium sulfate and concentrated in vacuo to afford the title compound (3.6 g, 97%) as a yellow solid.

HPLC (Method B): Rt 2.36 min (purity 99.3%). LC/MS: 222.1 (M+H)+.

$^1$H NMR (DMSO-d$_6$, 400 MHz) δ 12.5 (s, 1H), 7.74-7.72 (m, 2H), 7.06-7.04 (m, 1H), 3.75-3.72 (m, 4H), 2.90-2.88 (m, 4H), 2.33 (s, 3H).

Intermediate 36: 3-cyano-4-(2-methylpiperidin-1-yl)benzoic acid

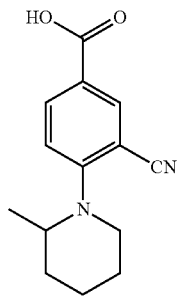 [SMILES: CC1CCCCN1c1ccc(C(=O)O)cc1C#N]

2-Methylpiperidine (744 mg; 7.5 mmol; 5 eq.) was added to a solution of methyl 3-cyano-4-fluorobenzoate (269 mg; 1.5 mmol; 1 eq.) in DMF (2 mL) and the resulting mixture was stirred at room temperature for 2 days. The solution was partitioned between ethyl acetate and water and the phases separated. The organic layer was washed with HCl 0.1 M then brine, dried over magnesium sulfate and concentrated in vacuo. The residue was taken up in THF (5 mL) and LiOH (126 mg; 3 mmol; 2 eq.) then water (5 mL) were added and the reaction mixture was stirred at room temperature for 5 hours. The resulting solution was diluted with water and washed with Et$_2$O. The aqueous layer was acidified to pH 2 with HCl 0.1 M and extracted with ethyl acetate. The organic phase was dried over magnesium sulfate and concentrated in vacuo to afford the title compound (294 mg, 80%) as an off-white solid.

LC/MS: 245.2 (M+H)+. $^1$H NMR (DMSO-d$_6$, 300 MHz) δ 12.99 (s, 1H), 8.07 (d, J=2.1 Hz, 1H), 8.00 (dd, J=2.1, 8.8 Hz, 1H), 7.17 (d, J=8.8 Hz, 1H), 4.14-4.04 (m, 1H), 3.29-3.21 (m, 2H), 1.87-1.46 (m, 6H), 1.09 (d, J=6.6 Hz, 3H)

Intermediate 37: 3-methyl-4-(2-methylpyridin-3-yl)benzoic acid

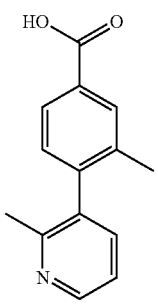

Step 1: methyl 3-methyl-4-(4,4,5,5-tetramethyl-1,3,2-dioxaborolan-2-yl)benzoate To a suspension of 3-methyl-4-(4,4,5,5-tetramethyl-1,3,2-dioxaborolan-2-yl)benzoic acid (Synthech BC3558-001, 800 mg; 3.05 mmol; 1 eq.) in MeOH (16 mL) was added dropwise thionyl chloride (0.89 mL; 12.2 mmol; 4 eq.) and the reaction mixture was stirred at room temperature for 4 hours. The solvent evaporated in vacuo and the crude residue was diluted with Ethyl acetate (20 mL). The organic layer was washed with a sat. aq. NaHCO$_3$ (5 mL), water (5 mL) and brine (5 mL), dried over magnesium sulfate and concentrated in vacuo to afford the title compound (751 mg, 89%) as a white solid.

HPLC (Method A): Rt 5.28 min (purity 78.4%). LC/MS: 276.9 (M+H)$^+$.

Step 2: 3-methyl-4-(2-methylpyridin-3-yl)benzoic acid

A mixture of 3-bromo-2-methylpyridine (0.13 mL; 1.16 mmol; 1 eq.), methyl 3-methyl-4-(4,4,5,5-tetramethyl-1,3,2-dioxaborolan-2-yl)benzoate (353 mg; 1.28 mmol; 1.1 eq.), potassium carbonate (803 mg; 5.81 mmol; 5 eq.) and tetrakis(triphenylphosphine)palladium(0) (134 mg; 0.12 mmol; 0.1 eq.) in toluene (1 mL) and water (1 mL) was refluxed for 2 hours. The reaction mixture was cooled down to room temperature and filtered through a pad of CELITE which was further washed with toluene (20 mL). The filtrate was concentrated in vacuo and the residue taken up in Ethyl acetate (10 mL). The organic layer was washed with a sat. aq. NaHCO$_3$, water and brine, dried over MgSO$_4$ and concentrated in vacuo. The residue (250 mg; 1.04 mmol; 1 eq.) was taken up in EtOH (7.5 mL) and sodium hydroxide (5M; 0.62 mL; 3.11 mmol; 3 eq.). The reaction mixture was stirred at 60° C. for 2 hours then concentrated in vacuo. The residue was taken up in water (50 mL) and the aqueous phase was washed with Ethyl acetate (2×20 mL) then acidified pH 2 with conc. HCl. The solution was concentrated in vacuo to ca. 15 mL, the precipitate filtered off and washed with ACN to afford the title compound (190 mg, 72%) as a beige solid.

HPLC (Method A): Rt 0.88 min (purity 97.1%). $^1$H NMR (DMSO-d6, 300 MHz) 13.04 (s, 1H), 8.78-8.77 (d, J=5.4 Hz, 1H), 8.16-8.13 (m, 1H), 7.98-7.95 (dd, J=1.9, 8.0 Hz, 1H), 7.77-7.76 (m, 2H), 7.56-7.54 (d, J=8.0 Hz, 1H), 2.37 (s, 3H), 2.13 (s, 3H).

Intermediate 38: 6-(2-methylpiperidin-1-yl)nicotinic acid

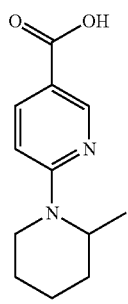 [SMILES: CC1CCCCN1c1ccc(C(=O)O)cn1]

A mixture of 6-chloronicotinonitrile (Maybridge SPB04745; 1.5 g; 10.8 mmol; 1 eq.) and 2-methylpiperidine (25.6 ml; 216.5 mmol; 20 eq.) was stirred at 90° C. for 24 hours. The mixture was diluted with ethyl acetate, washed with water and brine, dried over magnesium sulphate and concentrated in vacuo. To the residue (1.5 g; 7.45 mmol; 1 eq.) in water (90 mL) was added potassium hydroxide (2.09 g; 37.3 mmol; 5 eq.) and the reaction mixture was refluxed for 16 hours. After cooling to room temperature, the precipitate was filtered off and the filtrate acidified to pH 6 with HCl 1M. The precipitate was filtered off and dried to afford the title compound as a beige solid.

HPLC (Method A): Rt 3.41 min (purity 97.9%). LC/MS: 221.2 (M+H)$^+$.

Intermediate 39: 5-methyl-6-(2-methylpiperidin-1-yl)nicotinic acid

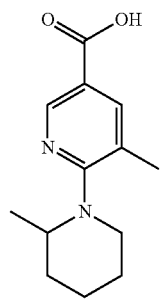

Step 1: 5-methyl-6-(2-methylpiperidin-1-yl)nicotinonitrile

A mixture of 5-cyano-2-fluoro-3-methylpyridine (Molekula M52391889; 1.5 g; 11 mmol; 1 eq.) and 2-methylpiperidine (5.2 mL; 44.1 mmol; 4 eq.) was stirred at 90° C. for 16 hours.

The reaction mixture was allowed to return to room temperature then diluted with ethyl acetate, washed with water, dried over magnesium sulphate and concentrated in vacuo to afford the title compound (2.2 g, 93%) as a brown oil.

HPLC (Method A): Rt 3.60 min (purity 84.5%). LC/MS: 216.2 (M+H)$^+$.

Step 2: 5-methyl-6-(2-methylpiperidin-1-yl)nicotinic acid

A mixture of 5-methyl-6-(2-methylpiperidin-1-yl)nicotinonitrile (1 g; 4.64 mmol; 1 eq.) and potassium hydroxide (1.3 g; 23.2 mmol; 5 eq.) in water (60 mL) was stirred at reflux for 16 hours. The pH was adjusted to 5-6 with HCl 1M and the aqueous layer extracted with ethyl acetate. The combined organic phase was dried over magnesium sulphate and concentrated in vacuo to afford the title compound (1.1 g, 100%) as a yellow oil.

HPLC (Method A): Rt 1.82 min (purity 88.7%). LC/MS: 235.2 (M+H)+.

Intermediate 40: 6-[2-(methoxymethyl)pyrrolidin-1-yl]-5-methylnicotinic acid

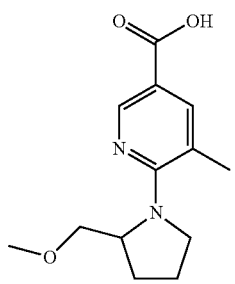

Step 1: 6-[2-(methoxymethyl)pyrrolidin-1-yl]-5-methylnicotinonitrile 2-(Methoxymethyl)pyrrolidine (Acb-blocks C5A-0029; 406 mg; 3.53 mmol; 1.2 eq.) and DIEA (1.52 ml; 8.82 mmol; 3 eq.) were added to a solution of 5-cyano-2-fluoro-3-methylpyridine (400 mg; 2.94 mmol; 1 eq.) in 1-butanol (1 mL) and the reaction mixture was stirred at 90° C. for 16 hours. The reaction mixture was allowed to return to room temperature then diluted with ethyl acetate, washed with water, dried over magnesium sulphate and concentrated in vacuo to afford the title compound (0.59 g, 87%) as a yellow oil.

HPLC (Method A): Rt 2.42 min (purity 99.1%). LC/MS: 200.1 (M+H)+.

Step 2: 6-[2-(methoxymethyl)pyrrolidin-1-yl]-5-methylnicotinic acid

A mixture of 6-[2-(methoxymethyl)pyrrolidin-1-yl]-5-methylnicotinonitrile (591 mg; 2.56 mmol; 1 eq.) and potassium hydroxide (717 mg; 12.8 mmol; 5 eq.) in water (20 mL) was stirred at reflux for 16 hours. The pH was adjusted to 5-6 with HCl 1M and the aqueous layer extracted with ethyl acetate. The combined organic phase was dried over magnesium sulphate and concentrated in vacuo to afford the title compound (0.63 g, 99%) as a white solid.

HPLC (Method A): Rt 1.44 min (purity 96.6%). LC/MS: 219.1 (M+H)+.

Intermediate 41: 2-(hydroxymethyl)-2'-methylbiphenyl-4-carboxylic acid

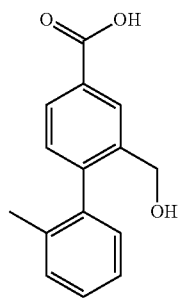 [SMILES: Cc1ccccc1-c1ccc(C(=O)O)cc1CO]

Step 1: Methyl 4-bromo-3-(bromomethyl)benzoate

To a solution of methyl 4-bromo-3-methylbenzoate (Aldrich 532878, 50 g; 218 mmol; 1 eq.) in CHCl3 (1 L) were added NBS (46.6 g; 262 mmol; 1.2 eq.) in one portion and α,α'-azoisobutyronitrile (0.72 g; 4.37 mmol; 0.02 eq.) and the reaction mixture was stirred at 70° C. for 2 days. The mixture was cooled down to room temperature and water (500 mL) was added. The organic layer was washed with aq. NaHCO3 (400 mL), then brine (500 mL), dried over MgSO4 and concentrated in vacuo. The residue was washed with n-pentane (2×500 mL) to afford the title compound as a yellow solid.

HPLC (Method A): Rt 4.44 min (purity 97.9%). $^1$H NMR (DMSO-d$_6$, 400 MHz) δ 8.24 (d, J=1.9 Hz, 1H), 7.88-7.82 (m, 2H), 4.87 (s, 2H), 3.91 (s, 3H).

Step 2: Methyl 3-[(acetyloxy)methyl]-4-bromobenzoate

To a solution of methyl 4-bromo-3-(bromomethyl)benzoate (6.5 g; 21 mmol; 1 eq.) in AcOH (32.5 mL) was added sodium acetate (3.46 g; 42 mmol; 2 eq.) and the reaction mixture was stirred at 100° C. for 12 hours. After concentration in vacuo, the residue was partitioned between Ethyl acetate and water. The organic layer was washed with 5% aq. NaHCO3 then brine, dried over MgSO4 and concentrated in vacuo. Purification by column chromatography (c-hexane/ethyl acetate, 5/1) afforded the title compound (4.78 g, 79%) as a white solid.

HPLC (Method A): Rt 4.37 min (purity 98.1%). $^1$H NMR (DMSO, 400 MHz) δ 8.03 (m, 1H), 7.85-7.84 (d, J=1.3 Hz, 1H), 5.18 (s, 2H), 3.87 (s, 3H), 2.11 (s, 3H).

Step 3: Methyl 2-[(acetyloxy)methyl]-2'-methylbiphenyl-4-carboxylate

A mixture of methyl 3-[(acetyloxy)methyl]-4-bromobenzoate (4.7 g; 16.4 mmol; 1 eq.), o-tolylboronic acid (2.45 g; 18 mmol; 1.1 eq.), potassium carbonate (11.3 g; 82 mmol; 5 eq.) and Pd(PPh3)4 (1.89 g; 1.64 mmol; 0.1 eq.) in toluene (23.5 mL) and water (23.5 mL) was refluxed for 2 hours. After cooling to room temperature, the reaction mixture was filtered through a pad of CELITE which was further washed with toluene (50 mL). The filtrate was concentrated in vacuo, the residue taken up in ethyl acetate (250 mL) and washed with sat. aq. NaHCO3 (100 mL), water (100 mL) and brine (100 mL), dried over magnesium sulphate and concentrated in vacuo to afford the title compound (4.9 g, 100%) as a brown oil.

HPLC (Method A): Rt 5.23 min (purity 62.3%).

Step 4: 2-(hydroxymethyl)-2'-methylbiphenyl-4-carboxylic acid

Sodium hydroxide (5M; 12.1 mL; 60.3 mmol; 3 eq.) was added to a solution of methyl 2-[(acetyloxy)methyl]-2'-methylbiphenyl-4-carboxylate (6 g; 20 mmol; 1 eq.) in EtOH (180 mL) and the reaction mixture was stirred at 60° C. for 2 hours. After concentration in vacuo, the residue was taken up in water (500 mL) and washed with Ethyl acetate (2×100 mL). The aqueous phase was acidified to pH 2 with conc. HCl and extracted with Ethyl acetate (2×100 mL). The combined organic layer was dried over MgSO4 and concentrated in vacuo to afford the title compound (3.46 g, 71%) as a yellow solid.

HPLC (Method A): Rt 3.77 min (purity 96.1%). LC/MS: 241.2 (M−H)−. $^1$H NMR (DMSO-d$_6$, 400 MHz) δ 12.97 (br s, 1H), 8.20-8.19 (m, 1H), 7.87-7.84 (dd, J=8.0 Hz, 1.86 Hz, 1H), 7.37-7.06 (m, 5H), 5.23-5.19 (m, 1H), 4.25-4.09 (m, 2H), 2.01 (s, 3H

Intermediate 42: 4-Piperidin-1-yl-3-(trifluoromethyl)benzoic acid

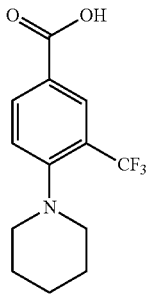

Step 1: 4-Piperidin-1-yl-3-(trifluoromethyl)benzonitrile

A mixture of 4-fluoro-3-trifluoro-methylbenzonitrile (5 g; 26.4 mmol; 1 eq.) and piperidine (5.2 mL; 52.8 mmol; 2 eq.) was stirred at 100° C. 20 hours. The reaction mixture was cooled, diluted with water (200 mL) and extracted with ethyl acetate (2×200 mL). The combined organic layer was washed with water (100 mL) and brine (100 mL), dried over sodium sulphate and concentrated in vacuo. The residue was purified by column chromatography (petroleum ether/ethyl acetate, 85/15) to afford the title compound of the title compound as an off-white solid.

HPLC (Method B): Rt 4.80 min (purity 99.1%).
LC/MS: 255.1 (M+H)$^+$. $^1$H NMR (DMSO-d$_6$, 400 MHz) δ 7.87 (s, 1H), 7.72-7.70 (m, 1H), 7.27-7.24 (m, 1H), 3.02-2.97 (m, 4H), 1.85-1.80 (m, 4H), 1.75-1.70 (m, 2H).

Step 2: Methyl 4-piperidin-1-yl-3-(trifluoromethyl)benzoate

A mixture of 4-piperidin-1-yl-3-(trifluoromethyl)benzonitrile (7.4 g, 27 mmol) and HCl in methanol (4M, 250 mL) was stirred at 60° C. for 12 hours, then concentrated to dryness. The residue was partitioned between ethyl acetate and 10% aq. NaHCO$_3$, and the organic layer washed with water then brine. Drying over magnesium sulphate and concentration in vacuo afforded the title compound (6.6 g, 85%) as a yellow oil.

$^1$H NMR (DMSO-d$_6$, 400 MHz) δ 8.38 (s, 1H), 8.25-8.21 (m, 1H), 7.47-7.45 (m, 1H), 3.94 (s, 3H), 3.04-2.99 (m, 4H), 1.81-1.78 (m, 4H), 1.75-1.70 (m, 2H).

Step 3: 4-Piperidin-1-yl-3-(trifluoromethyl)benzoic acid

Lithium hydroxide (2.83 g, 67.5 mmol, 2 eq.) was added to a solution of methyl 4-piperidin-1-yl-3-(trifluoromethyl)benzoate (9.7 g, 33.7 mmol, 1 eq.) in THF (50 mL) and water (5 mL) and the reaction mixture was stirred at room temperature for 12 hours. The solvent was removed in vacuo and the residue taken up in water. The aqueous layer was washed with DCM, acidified to pH 2 with conc. HCl and extracted with ethyl acetate. The organic phase was washed with brine, dried over sodium sulphate and concentrated in vacuo to afford the title compound (3.0 g, 95%) as a white solid.

HPLC (Method B): Rt 4.36 min (purity 91.7%). LC/MS: 272.9 (M+H)$^+$. $^1$H NMR (DMSO-d$_6$, 400 MHz) δ 13.30 (s, 1H), 8.12-8.10 (m, 2H), 7.49-7.47 (m, 1H), 2.92-2.90 (m, 4H), 1.65-1.60 (m, 4H), 1.57-1.53 (m, 2H).

Example 1

1-{4-[3-(2-methoxyphenyl)-1,2,4-oxadiazol-5-yl]-2-nitrophenyl}piperidine

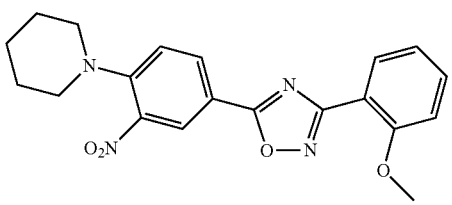 [SMILES: COc1ccccc1-c1noc(-c2ccc(N3CCCCC3)c([N+](=O)[O-])c2)n1]

Trichloroacetonitrile (0.08 mL; 0.75 mmol; 1.50 eq.), intermediate 4 (125 mg; 0.50 mmol; 1 eq.), polymer bound triphenylphosphine (499.49 mg; 1.50 mmol; 3 eq.), intermediate 1 (91.31 mg; 0.55 mmol; 1.10 eq.) and DIEA (0.17 mL; 1 mmol; 2 eq.) were reacted according to general procedure 1. Purification by column chromatography c-hexane/ethyl acetate, 80/20) followed by crystallization (Et$_2$O/n-hexane) afforded the title compound as an orange solid.

HPLC (Method A): Rt 5.32 min (purity 97.4%). LC/MS: 381.0 (M+H)$^+$.

Example 2

4-{4-[3-(2-methoxyphenyl)-1,2,4-oxadiazol-5-yl]-2-nitrophenyl}morpholine

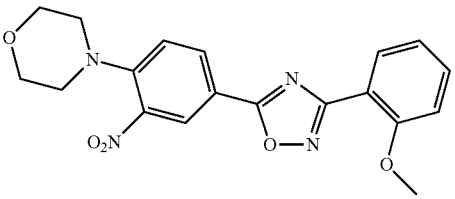 [SMILES: COc1ccccc1-c1noc(-c2ccc(N3CCOCC3)c([N+](=O)[O-])c2)n1]

Trichloroacetonitrile (0.08 mL; 0.75 mmol; 1.50 eq.), intermediate 5 (126 mg; 0.50 mmol; 1 eq.), polymer bound triphenylphosphine (499.55 mg; 1.50 mmol; 3 eq.), intermediate 1 (91.32 mg; 0.55 mmol; 1.10 eq.) and DIEA (0.17 mL; 1 mmol; 2 eq.) were reacted according to general procedure 1. Purification by column chromatography using DCM as eluent afforded an orange oil which crystallized on standing to afford the title compound as a yellow solid.

HPLC (Method A): Rt 4.35 min (purity 93.4%). LC/MS: 383.0 (M+H)+.

Example 3

1-(4-{3-[2-(trifluoromethoxy)phenyl]-1,2,4-oxadiazol-5-yl}phenyl)piperidine

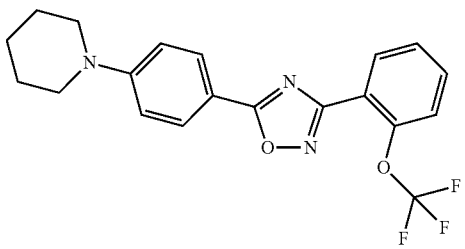 [SMILES: FC(F)(F)Oc1ccccc1-c1noc(-c2ccc(N3CCCCC3)cc2)n1]

Oxalyl chloride (166.96 mg; 1.32 mmol; 3 eq.), intermediate 6 (90 mg; 0.44 mmol; 1 eq.), intermediate 2 (96.53 mg; 0.44 mmol; 1 eq.) and DIEA (170.01 mg; 1.32 mmol; 3 eq.) were reacted according to general procedure 2. Purification by column chromatography c-hexane/ethyl acetate, 90/10) afforded the title compound as an off-white solid.

HPLC (Method A): Rt 5.39 min (purity 99.5%). LC/MS: 390.0 (M+H)+.

Example 4

1-{4-[3-(2-methoxyphenyl)-1,2,4-oxadiazol-5-yl]phenyl}piperidine

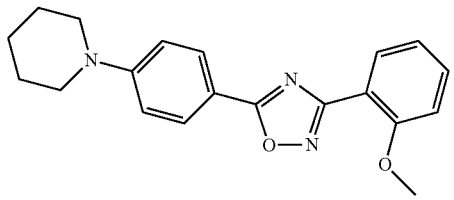 [SMILES: COc1ccccc1-c1noc(-c2ccc(N3CCCCC3)cc2)n1]

Oxalyl chloride (166.96 mg; 1.32 mmol; 3 eq.), intermediate 6 (90 mg; 0.44 mmol; 1 eq.), intermediate 1 (72.87 mg; 0.44 mmol; 1 eq.) and DIEA (170.01 mg; 1.32 mmol; 3 eq.) in THF (1 mL) were reacted according to general procedure 2. Purification by crystallization (Et2O/n-hexane) afforded the title compound as an off-white solid.

HPLC (Method A): Rt 4.10 min (purity 95.0%). LC/MS: 336.0 (M+H)+.

Example 5

N-cyclohexyl-N-methyl-2-nitro-4-{3-[2-(trifluoromethoxy)phenyl]-1,2,4-oxadiazol-5-yl}aniline

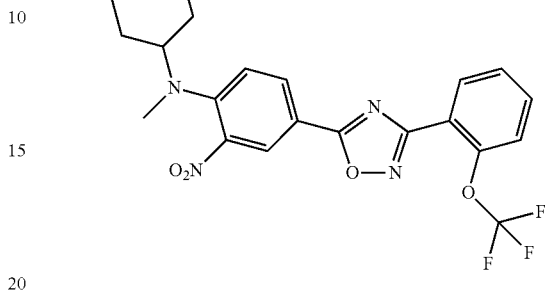

Oxalyl chloride (190.39 mg; 1.50 mmol; 3 eq.), intermediate 7 (139.15 mg; 0.50 mmol; 1 eq), intermediate 2 (110.08 mg; 0.50 mmol; 1 eq.) and DIEA (193.87 mg; 1.50 mmol; 3 eq.) were reacted according to general procedure 2. Purification by column chromatography (c-hexane/ethyl acetate, 90/10) followed by crystallization (n-hexane) afforded the title compound as a yellow solid.

HPLC (Method A): Rt 6.44 min (purity 98.6%). LC/MS: 463.2 (M+H)+.

Example 6

5-[3-(2-methoxyphenyl)-1,2,4-oxadiazol-5-yl]-2-morpholin-4-ylaniline

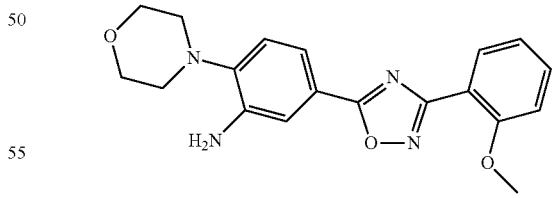

Stannous chloride dihydrate (147.53 mg; 0.65 mmol; 5 eq.) was added to a solution of example 2 (50 mg; 0.13 mmol; 1 eq.) in EtOH (10 mL), and the reaction mixture was stirred at 70° C. for 3 hours. After cooling, the solution was partitioned between ethyl acetate and aqueous NaHCO3. The organic layer was washed four times with brine, dried over magnesium sulfate and concentrated in vacuo to give a yellow solid. The latter was triturated in Et2O and filtrated to afford the title compound (38 mg, 82%) as a pale yellow solid.

HPLC (Method A): Rt 3.60 min (purity 96.7%). LC/MS: 353.1 (M+H)+.

Example 7

1-{4-[3-(2-ethoxyphenyl)-1,2,4-oxadiazol-5-yl]-2-nitrophenyl}piperidine

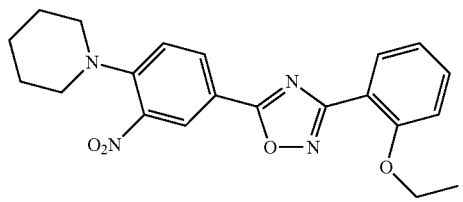 [SMILES: CCOc1ccccc1-c1noc(-c2ccc(N3CCCCC3)c([N+](=O)[O-])c2)n1]

Oxalyl chloride (190.39 mg; 1.50 mmol; 3 eq.), intermediate 4 (125.13 mg; 0.50 mmol; 1 eq.), intermediate 3 (90.10 mg; 0.50 mmol; 1 eq.) and DIEA (0.17 mL; 1 mmol; 2 eq.) were reacted according to general procedure 2. Purification by chromatography c-hexane/ethyl acetate, 95/5 then 90/10) afforded the title compound (139 mg, 70%) as an orange oil.

HPLC (Method A): Rt 5.73 min (purity 98.0%). LC/MS: 395.1 (M+H)+.

Example 8

2-methyl-1-(2-nitro-4-{3-[2-(trifluoromethoxy)phenyl]-1,2,4-oxadiazol-5-yl}phenyl)piperidine

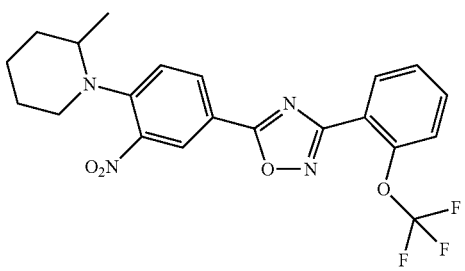 [SMILES: CC1CCCCN1c1ccc(-c2nc(-c3ccccc3OC(F)(F)F)no2)cc1[N+](=O)[O-]]

Oxalyl chloride (190.39 mg; 1.50 mmol; 3 eq.), intermediate 8 (132.14 mg; 0.50 mmol; 1 eq.), intermediate 2 (110.08 mg; 0.50 mmol; 1 eq.) and DIEA (193.87 mg; 1.50 mmol; 3 eq.) were reacted according to general procedure 2. Purification by column chromatography (c-Hexane/ethyl acetate, 90/10) followed by crystallization (Et2O/n-hexane) afforded the title compound as a yellow solid.

HPLC (Method A): Rt 6.26 min (purity 98.4%). LC/MS: 449.2 (M+H)+.

Example 9

1-{4-[3-(2-methoxyphenyl)-1,2,4-oxadiazol-5-yl]-2-nitrophenyl}-2-methylpiperidine

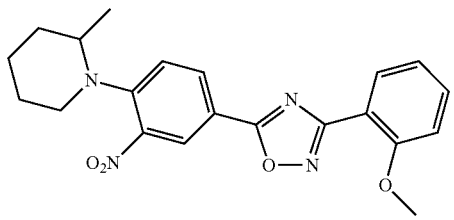 [SMILES: COc1ccccc1-c1noc(-c2ccc(N3CCCCC3C)c([N+](=O)[O-])c2)n1]

Oxalyl chloride (190.39 mg; 1.50 mmol; 3 eq.), intermediate 8 (132.14 mg; 0.50 mmol; 1 eq.), intermediate 1 (83.09 mg; 0.50 mmol; 1 eq.) and DIEA (193.87 mg; 1.50 mmol; 3 eq.) were reacted according to general procedure 2. Purification by column chromatography (c-hexane/ethyl acetate, 80/20) afforded the title compound (162 mg, 82%) as an orange oil.

HPLC (Method A): Rt 5.46 min (purity 98.0%). LC/MS: 395.1 (M+H)+.

Example 10

1-{4-[3-(2-ethoxyphenyl)-1,2,4-oxadiazol-5-yl]-2-nitrophenyl}-2-methylpiperidine

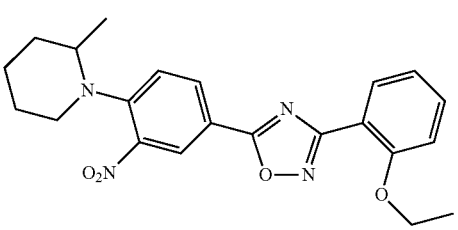 [SMILES: CCOc1ccccc1-c1noc(-c2ccc(N3CCCCC3C)c([N+](=O)[O-])c2)n1]

Oxalyl chloride (190.39 mg; 1.50 mmol; 3 eq.), intermediate 8 (132.14 mg; 0.50 mmol; 1 eq.), intermediate 3 (90.10 mg; 0.50 mmol; 1 eq.) and DIEA (193.87 mg; 1.50 mmol; 3 eq.) were reacted according to general procedure 2. Purification by column chromatography (c-hexane/ethyl acetate, 90/10) afforded the title compound as an orange oil.

HPLC (Method A): Rt 5.98 min (purity 97.6%). LC/MS: 409.2 (M+H)⁺.

Example 11

3,3-difluoro-1-(2-nitro-4-{3-[2-(trifluoromethoxy)phenyl]-1,2,4-oxadiazol-5-yl}phenyl)piperidine

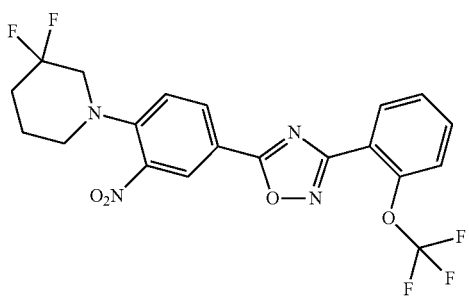 [SMILES: O=[N+]([O-])c1cc(-c2nc(-c3ccccc3OC(F)(F)F)no2)ccc1N1CCCC(F)(F)C1]

Oxalyl chloride (190.39 mg; 1.50 mmol; 3 eq.), intermediate 9 (143.12 mg; 0.50 mmol; 1 eq.), intermediate 2 (110.08 mg; 0.50 mmol; 1 eq.) and DIEA (193.87 mg; 1.50 mmol; 3 eq.) were reacted according to general procedure 2. Purification by crystallization (ethyl acetate/n-hexane) afforded the title compound (218 mg, 93%) as a yellow solid.

HPLC (Method A): Rt 5.64 min (purity 99.1%). LC/MS: 470.9 (M+H)⁺.

Example 12

3,3-difluoro-1-{4-[3-(2-methoxyphenyl)-1,2,4-oxadiazol-5-yl]-2-nitrophenyl}piperidine

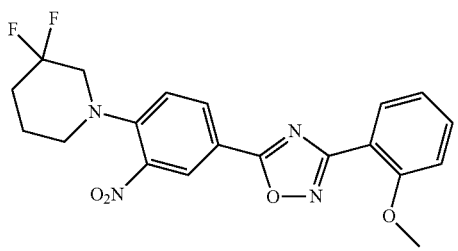 [SMILES: COc1ccccc1-c1noc(-c2ccc(N3CCCC(F)(F)C3)c([N+](=O)[O-])c2)n1]

Oxalyl chloride (190.39 mg; 1.50 mmol; 3 eq.), intermediate 9 (143.12 mg; 0.50 mmol; 1 eq.), intermediate 1 (83.09 mg; 0.50 mmol; 1 eq.) and DIEA (193.87 mg; 1.50 mmol; 3 eq.) were reacted according to general procedure 2. Purification by crystallization (ethyl acetate/n-hexane) afforded the title compound as a yellow solid.

HPLC (Method A): Rt 4.97 min (purity 99.4%). LC/MS: 417.0 (M+H)⁺.

Example 13

3-(2-methoxyphenyl)-5-(3-nitro-4-pyrrolidin-1-ylphenyl)-1,2,4-oxadiazole

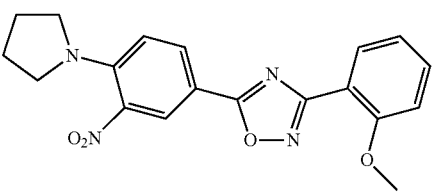 [SMILES: COc1ccccc1-c1noc(-c2ccc(N3CCCC3)c([N+](=O)[O-])c2)n1]

Oxalyl chloride (190.39 mg; 1.50 mmol; 3 eq.), intermediate 10 (118.11 mg; 0.50 mmol; 1 eq.), intermediate 1 (83.09 mg; 0.50 mmol; 1 eq.) and DIEA (193.87 mg; 1.50 mmol; 3 eq.) were reacted according to general procedure 2. Purification by column chromatography (c-hexane/ethyl acetate, 80/20) afforded the title compound as an orange solid.

HPLC (Method A): Rt 4.82 min (purity 96.7%). LC/MS: 366.9 (M+H)⁺.

Example 14

5-(3-nitro-4-pyrrolidin-1-ylphenyl)-3-[2-(trifluoromethoxy)phenyl]-1,2,4-oxadiazole

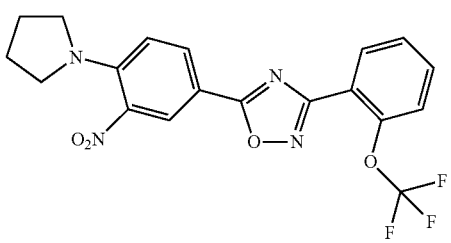 [SMILES: O=[N+]([O-])c1cc(-c2nc(-c3ccccc3OC(F)(F)F)no2)ccc1N1CCCC1]

Oxalyl chloride (190.39 mg; 1.50 mmol; 3 eq.), intermediate 10 (118.11 mg; 0.50 mmol; 1 eq.), intermediate 2 (110.08 mg; 0.50 mmol; 1 eq.) and DIEA (193.87 mg; 1.50 mmol; 3 eq.) were reacted according to general procedure 2. Purification by column chromatography (c-hexane/ethyl acetate, 80/20) afforded the title compound as an orange solid.

HPLC (Method A): Rt 5.64 min (purity 93.1%). LC/MS: 420.9 (M+H)+.

Example 15

1-(2-nitro-4-{3-[2-(trifluoromethoxy)phenyl]-1,2,4-oxadiazol-5-yl}phenyl)azepane

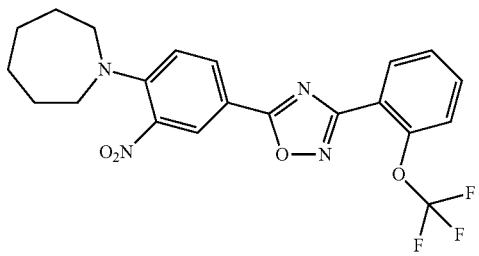 [SMILES: O=[N+]([O-])c1cc(-c2nc(-c3ccccc3OC(F)(F)F)no2)ccc1N1CCCCCC1]

Oxalyl chloride (190.39 mg; 1.50 mmol; 3 eq.), intermediate 11 (132.14 mg; 0.50 mmol; 1 eq.), intermediate 2 (110.08 mg; 0.50 mmol; 1 eq.) and DIEA (193.87 mg; 1.50 mmol; 3 eq.) were reacted according to general procedure 2. Purification by column chromatography (c-hexane/ethyl acetate, 80/20) afforded the title compound as a yellow solid.

HPLC (Method A): Rt 6.07 min (purity 87.8%). LC/MS: 448.9 (M+H)+.

Example 16

1-{4-[3-(2-methoxyphenyl)-1,2,4-oxadiazol-5-yl]-2-nitrophenyl}azepane

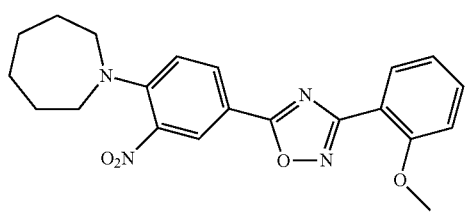 [SMILES: COc1ccccc1-c1noc(-c2ccc(N3CCCCCC3)c([N+](=O)[O-])c2)n1]

Oxalyl chloride (190.39 mg; 1.50 mmol; 3 eq.), intermediate 11 (132.14 mg; 0.50 mmol; 1 eq.), intermediate 1 (83.09 mg; 0.50 mmol; 1 eq.) and DIEA (193.87 mg; 1.50 mmol; 3 eq.) were reacted according to general procedure 2. Purification by column chromatography (c-hexane/ethyl acetate, 80/20) afforded the title compound as an orange solid.

HPLC (Method A): Rt 5.29 min (purity 88.5%). LC/MS: 395.0 (M+H)+.

Example 17

4-(2-nitro-4-{3-[2-(trifluoromethoxy)phenyl]-1,2,4-oxadiazol-5-yl}phenyl)morpholine

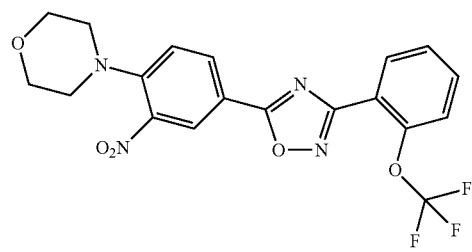 [SMILES: O=[N+]([O-])c1cc(-c2nc(-c3ccccc3OC(F)(F)F)no2)ccc1N1CCOCC1]

Oxalyl chloride (131 µl; 1.55 mmol; 3 eq.), intermediate 5 (130 mg; 0.52 mmol; 1 eq.), intermediate 2 (113.47 mg; 0.52 mmol; 1 eq.) and DIEA (114.20 µl; 1.55 mmol; 3 eq.) were reacted according to general procedure 2. Purification by column chromatography c-hexane/ethyl acetate, 80/20) afforded the title compound as a yellow solid.

HPLC (Method A): Rt 5.24 min (purity 96.7%). LC/MS: 436.9 (M+H)+.

Example 18

4-[4-[3-(2-methoxyphenyl)-1,2,4-oxadiazol-5-yl]-2-(trifluoromethyl)phenyl]morpholine

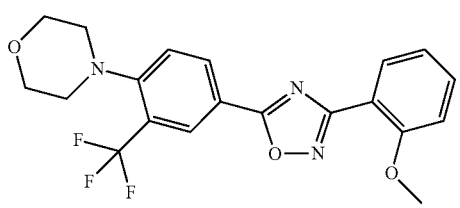 [SMILES: COc1ccccc1-c1noc(-c2ccc(N3CCOCC3)c(C(F)(F)F)c2)n1]

Oxalyl chloride (190.39 mg; 1.50 mmol; 3 eq.), intermediate 14 (137.61 mg; 0.50 mmol; 1 eq.), intermediate 1 (83.09 mg; 0.50 mmol; 1 eq.) and DIEA (193.87 mg; 1.50 mmol; 3 eq.) were reacted according to general procedure 2. Purification by crystallization (ethyl acetate/n-pentane) afforded the title compound (160 mg, 79%) as an off-white solid.

HPLC (Method A): Rt 4.98 min (purity 95.7%). LC/MS: 406.1 (M+H)+.

Example 19

4-[4-{3-[2-(trifluoromethoxy)phenyl]-1,2,4-oxadiazol-5-yl}-2-(trifluoromethyl)phenyl]morpholine

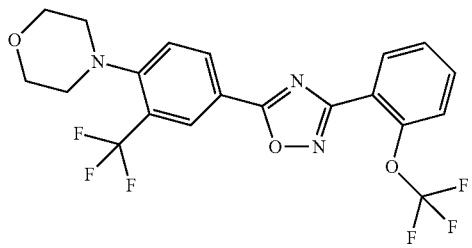 [SMILES: FC(F)(F)Oc1ccccc1-c1noc(-c2ccc(N3CCOCC3)c(C(F)(F)F)c2)n1]

Oxalyl chloride (190.39 mg; 1.50 mmol; 3 eq.), intermediate 14 (137.61 mg; 0.50 mmol; 1 eq.), intermediate 2 (110.08 mg; 0.50 mmol; 1 eq.) and DIEA (193.87 mg; 1.50 mmol; 3 eq.) were reacted according to general procedure 2. Purification by crystallization (n-pentane) afforded the title compound as an off-white solid.

HPLC (Method A): Rt 5.78 min (purity 98.9%). LC/MS: 459.9 (M+H)+.

Example 20

5-(2,2'-dimethylbiphenyl-4-yl)-3-(2-methoxyphenyl)-1,2,4-oxadiazole

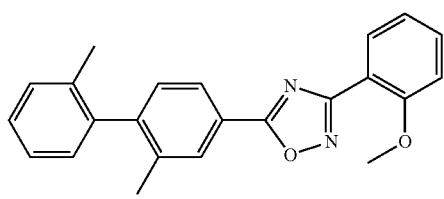 [SMILES: COc1ccccc1-c1noc(-c2ccc(-c3ccccc3C)c(C)c2)n1]

Trichloroacetonitrile (0.08 mL; 0.75 mmol; 1.50 eq.), intermediate 16 (113 mg; 0.50 mmol; 1 eq.), polymer bound triphenylphosphine (499.40 mg; 1.50 mmol; 3 eq.), intermediate 2 (91.29 mg; 0.55 mmol; 1.10 eq.) and DIEA (0.17 mL; 1 mmol; 2 eq.) in THF (2 mL) were reacted according to general procedure 1. Purification by column chromatography (c-hexane/ethyl acetate, 90/10) afforded the title compound as a brownish oil.

HPLC (Method A): Rt 5.87 min (purity 89.7%). LC/MS: 357.0 (M+H)+.

Example 21

5-(2,2'-dimethylbiphenyl-4-yl)-3-[2-(trifluoromethoxy)phenyl]-1,2,4-oxadiazole

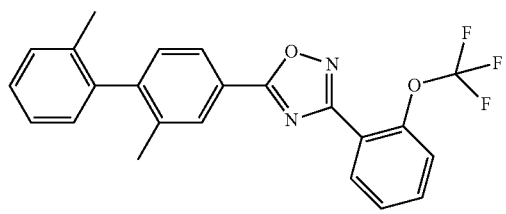 [SMILES: Cc1ccccc1-c1ccc(-c2nc(-c3ccccc3OC(F)(F)F)no2)cc1C]

Oxalyl chloride (190.39 mg; 1.50 mmol; 3 eq.), intermediate 16 (113.14 mg; 0.50 mmol; 1 eq), intermediate 2 (110.08 mg; 0.50 mmol; 1 eq.) and DIEA (193.87 mg; 1.50 mmol; 3 eq.) were reacted according to general procedure 2. Purification by column chromatography (c-hexane then c-hexane/ethyl acetate, 98/2) afforded the title compound as a colourless oil.

HPLC (Method A): Rt 6.62 min (purity 99.1%). LC/MS: 411.1 (M+H)+.

Example 22

5-(2,2'-dimethylbiphenyl-4-yl)-3-(2-ethoxyphenyl)-1,2,4-oxadiazole

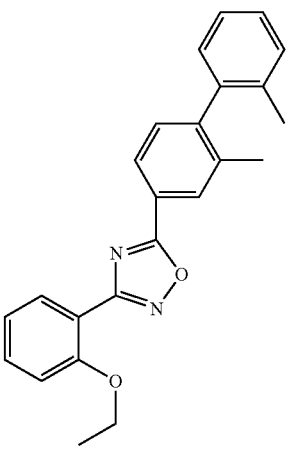 [SMILES: CCOc1ccccc1-c1noc(-c2ccc(-c3ccccc3C)c(C)c2)n1]

Oxalyl chloride (0.04 mL; 0.52 mmol; 1.05 eq.), intermediate 16 (113.14 mg; 0.50 mmol; 1 eq), intermediate 3 (90.10 mg; 0.50 mmol; 1 eq.) and DIEA (0.17 mL; 1 mmol; 2 eq.) were reacted according to general procedure 2. Purification by column chromatography (c-hexane/ethyl acetate, 97/3 to 95/5) followed by crystallization (ethanol/methanol) afforded the title compound as a white solid.

HPLC (Method A): Rt 6.29 min (purity 99.7%). LC/MS: 371.1 (M+H)⁺.

Example 23

5-[2-methyl-2'-(trifluoromethyl)biphenyl-4-yl]-3-[2-(trifluoromethoxy)phenyl]-1,2,4-oxadiazole

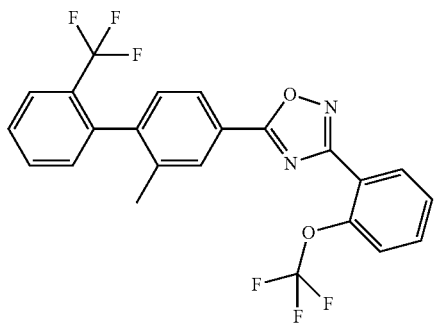 [SMILES: Cc1cc(-c2nc(-c3ccccc3OC(F)(F)F)no2)ccc1-c1ccccc1C(F)(F)F]

Oxalyl chloride (190.39 mg; 1.50 mmol; 3 eq.), intermediate 18 (140.12 mg; 0.50 mmol; 1 eq.), intermediate 2 (110.08 mg; 0.50 mmol; 1 eq.) and DIEA (193.87 mg; 1.50 mmol; 3 eq.) were reacted according to general procedure 2. Purification by crystallization (n-hexane) the title compound as a white solid.

HPLC (Method A): Rt 6.45 min (purity 99.6%). LC/MS: 465.0 (M+H)⁺.

Example 24

3-(2-methoxyphenyl)-5-[2-methyl-2'-(trifluoromethyl)biphenyl-4-yl]-1,2,4-oxadiazole

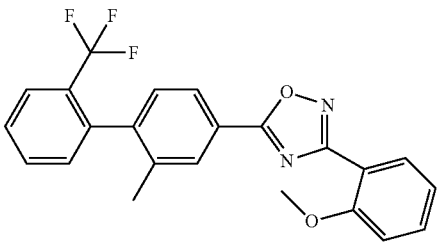 [SMILES: COc1ccccc1-c1noc(-c2ccc(-c3ccccc3C(F)(F)F)c(C)c2)n1]

Oxalyl chloride (190.39 mg; 1.50 mmol; 3 eq.), intermediate 18 (140.12 mg; 0.50 mmol; 1 eq.), intermediate 1 (83.09 mg; 0.50 mmol; 1 eq.) and DIEA (193.87 mg; 1.50 mmol; 3 eq.) were reacted according to general procedure 2. Purification by column chromatography (c-hexane/ethyl acetate, 90/10) afforded the title compound (152 mg, 74%) as an off-white solid.

HPLC (Method A): Rt 5.92 min (purity 95.2%). LC/MS: 411.4 (M+H)⁺.

Example 25

3-(2-methoxyphenyl)-5-[3-methyl-4-(4-methyl-3-thienyl)phenyl]-1,2,4-oxadiazole

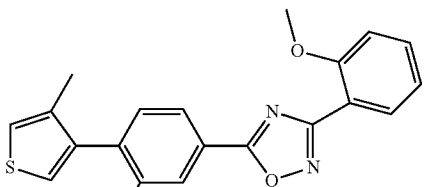

Oxalyl chloride (131.13 µA; 1.55 mmol; 3 eq.), intermediate 20 (120 mg; 0.52 mmol; 1 eq.), intermediate 1 (85.84 mg; 0.52 mmol; 1 eq.) and DIEA (267.05 µA; 1.55 mmol; 3 eq.) were reacted according to general procedure 2. Purification by column chromatography c-hexane/ethyl acetate, 90/10) followed by crystallization (n-pentane) afforded the title compound as a white solid.

HPLC (Method A): Rt 5.68 min (purity 99.9%). LC/MS: 362.9 (M+H)⁺.

Example 26

3-(2-methoxyphenyl)-5-(2'-methyl-2-nitrobiphenyl-4-yl)-1,2,4-oxadiazole

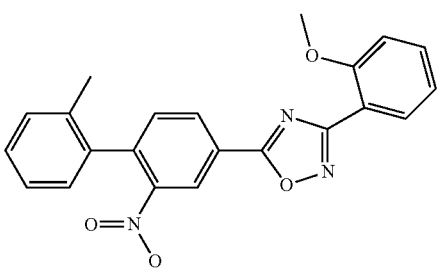

Oxalyl chloride (118.42 µl; 1.40 mmol; 3 eq.), intermediate 22 (120 mg; 0.47 mmol; 1 eq.), intermediate 1 (77.52 mg; 0.47 mmol; 1 eq.) and DIEA (103.36 µl; 1.40 mmol; 3 eq.) were reacted according to general procedure 2. Purification by crystallization (n-pentane) afforded the title compound as a white solid.

HPLC (Method A): Rt 5.37 min (purity 94.6%). LC/MS: 387.9 (M+H)+.

Example 27

5-(4-cyclohexylphenyl)-3-(2-methoxyphenyl)-1,2,4-oxadiazole

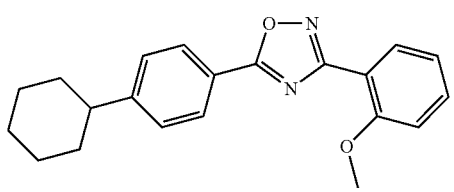 [SMILES: COc1ccccc1-c1noc(-c2ccc(C3CCCCC3)cc2)n1]

Trichloroacetonitrile (0.15 ml; 1.50 mmol; 1.50 eq.), 4-cyclohexylbenzoic acid (Lancaster 5086; 204.27 mg; 1.00 mmol; 1 eq.), polymer bound triphenylphosphine (1.87 g; 3.00 mmol; 3 eq.), intermediate 1 (182.80 mg; 1.10 mmol; 1.10 eq.) and DIEA (0.34 ml; 2.00 mmol; 2 eq.) were reacted according to general procedure 1. Purification by column chromatography (c-hexane/ethyl acetate, 98/2 to 95/5) followed by crystallization (methanol) afforded the title compound as a yellow solid.

HPLC (Method A): Rt 5.98 min (purity 99.9%). LC/MS: 335.1 (M+H)+.

Example 28

5-(4-isobutylphenyl)-3-(2-methoxyphenyl)-1,2,4-oxadiazole

Trichloroacetonitrile (0.15 mL; 1.50 mmol; 1.50 eq.), 4-isobutylbenzoic acid (Enamine EN300-11610; 204.27 mg; 1.00 mmol; 1 eq.), polymer bound triphenylphosphine (1.87 g; 3.00 mmol; 3 eq.), intermediate 1 (182.80 mg; 1.10 mmol; 1.10 eq.) and DIEA (0.34 mL; 2.00 mmol; 2 eq.) were reacted according to general procedure 1. Purification by crystallization (CH$_3$CN/water) afforded the title compound as a white solid.

HPLC (Method A): Rt 5.67 min (purity 100%). LC/MS: 309.0 (M+H)+.

Example 29

5-(4-cyclohexylphenyl)-3-[2-(trifluoromethoxy)phenyl]-1,2,4-oxadiazole

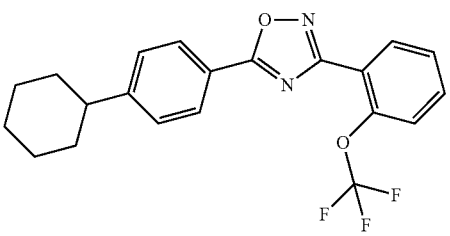 [SMILES: FC(F)(F)Oc1ccccc1-c1noc(-c2ccc(C3CCCCC3)cc2)n1]

Oxalyl chloride (0.04 mL; 0.52 mmol; 1.05 eq.), 4-cyclohexylbenzoic acid (Lancaster 5086; 89.11 mg; 0.50 mmol; 1.00 eq.), intermediate 2 (110.08 mg; 0.50 mmol; 1 eq.) and DIEA (0.17 mL; 1.40 mmol; 3 eq.) were reacted according to general procedure 2. Purification by column chromatography (c-hexane/ethyl acetate, 80/20) afforded the title compound as a white solid.

HPLC (Method A): Rt 6.66 min (purity 96.8%). LC/MS: 389.1 (M+H)+.

Example 30

5-(4-isobutylphenyl)-3-[2-(trifluoromethoxy)phenyl]-1,2,4-oxadiazole

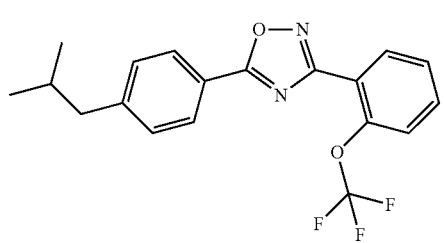 [SMILES: CC(C)Cc1ccc(-c2nc(-c3ccccc3OC(F)(F)F)no2)cc1]

Oxalyl chloride (0.04 mL; 0.52 mmol; 1.05 eq.), 4-isobutylbenzoic acid (Enamine EN300-11610; 102.13 mg; 0.50 mmol; 1.00 eq.), intermediate 2 (110.08 mg; 0.50 mmol; 1 eq.) and DIEA (0.17 mL; 1.40 mmol; 3 eq.) were reacted according to general procedure 2. Purification by column chromatography (c-hexane/ethyl acetate, 99/1) afforded the title compound as a colorless oil.

HPLC (Method A): Rt 6.39 min (purity 99.1%). LC/MS: 363.0 (M+H)⁺.

Example 31

1-(2-nitro-4-{3-[2-(trifluoromethoxy)phenyl]-1,2,4-oxadiazol-5-yl}phenyl)piperidine

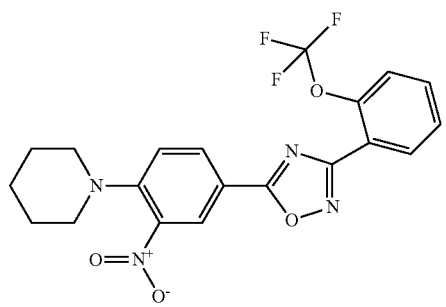 [SMILES: O=[N+]([O-])c1cc(-c2nc(-c3ccccc3OC(F)(F)F)no2)ccc1N1CCCCC1]

Oxalyl chloride (71 μL; 0.84 mmol; 3 eq.), Intermediate 4 (70 mg; 0.28 mmol; 1 eq.), Intermediate 2 (62 mg; 0.28 mmol, 1 eq.) and DIEA (145 μL; 0.84 mmol; 3 eq.) were reacted according to general procedure 2. Purification by column chromatography (c-hexane/ethyl acetate, 80/20) followed by precipitation in n-pentane afforded the title compound as a yellow solid.

HPLC (Method A): Rt 6.11 min (purity 100%). LC/MS: 434.9 (M+H)⁺.

Example 32

1-{4-[3-(5-fluoro-2-methoxyphenyl)-1,2,4-oxadiazol-5-yl]-2-nitrophenyl}-2-methylpiperidine

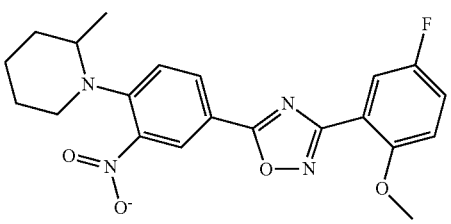

Oxalyl chloride (190 mg; 1.5 mmol; 3 eq.), Intermediate 8 (132 mg; 0.5 mmol; 1 eq.), Intermediate 23 (92 mg; 0.5 mmol, 1 eq.) and DIEA (194 mg; 1.5 mmol; 3 eq.) were reacted according to general procedure 2. Purification by column chromatography (c-hexane/ethyl acetate, 80/20) followed by crystallisation from ethyl acetate/n-pentane afforded the title compound as a yellow solid.

HPLC (Method A): Rt 5.64 min (purity 99.2%). LC/MS: 412.9 (M+H)⁺.

Example 33

5-(2,2'-dimethylbiphenyl-4-yl)-3-(5-fluoro-2-methoxyphenyl)-1,2,4-oxadiazole

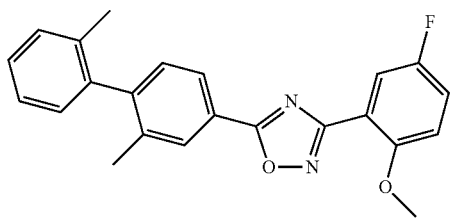 [SMILES: COc1ccc(F)cc1-c1noc(-c2ccc(-c3ccccc3C)c(C)c2)n1]

Oxalyl chloride (190 mg; 1.5 mmol; 3 eq.), Intermediate 16 (113 mg; 0.5 mmol; 1 eq.), Intermediate 23 (92 mg; 0.5 mmol, 1 eq.) and DIEA (194 mg; 1.5 mmol; 3 eq.) were reacted according to general procedure 2. Purification by column chromatography c-hexane/ethyl acetate, 90/10) afforded the title compound as a yellow solid.

HPLC (Method A): Rt 5.96 min (purity 100%). LC/MS: 453.9 (M+H)⁺.

Example 34

2-methyl-1-[4-{3-[2-(trifluoromethoxy)phenyl]-1,2,4-oxadiazol-5-yl}-2-(trifluoromethyl)phenyl]piperidine

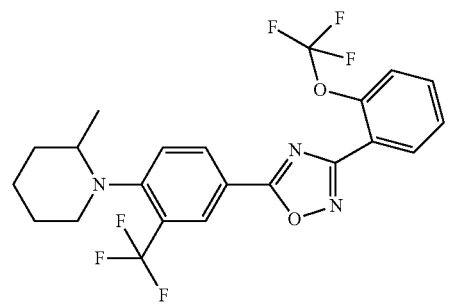 [SMILES: CC1CCCCN1c1ccc(-c2nc(-c3ccccc3OC(F)(F)F)no2)cc1C(F)(F)F]

Oxalyl chloride (106 μL; 1.25 mmol; 3 eq.), Intermediate 24 (120 mg; 0.42 mmol; 1 eq.), Intermediate 2 (92 mg; 0.42 mmol, 1 eq.) and DIEA (93 μL; 1.25 mmol; 3 eq.) were reacted according to general procedure 2. Purification by column chromatography c-hexane/ethyl acetate, 80/20) followed by precipitation from n-pentane afforded the title compound as a yellow solid.

HPLC (Method A): Rt 7.09 min (purity 93.5%). LC/MS: 471.8 (M+H)⁺.

Example 35

1-[4-[3-(2-methoxyphenyl)-1,2,4-oxadiazol-5-yl]-2-(trifluoromethyl)phenyl]-2-methylpiperidine

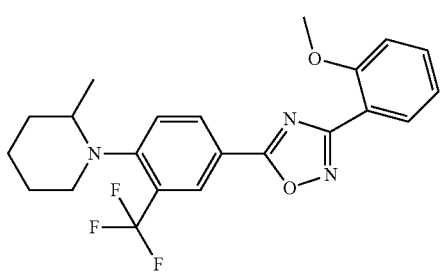 [SMILES: COc1ccccc1-c1noc(-c2ccc(N3CCCCC3C)c(C(F)(F)F)c2)n1]

Oxalyl chloride (106 μL; 1.25 mmol; 3 eq.), Intermediate 24 (120 mg; 0.42 mmol; 1 eq.), Intermediate 1 (69 mg; 0.42 mmol, 1 eq.) and DIEA (93 μL; 1.25 mmol; 3 eq.) were reacted according to general procedure 2. Purification by column chromatography c-hexane/ethyl acetate, 80/20) followed by precipitation from n-pentane afforded the title compound as a white solid.

HPLC (Method A): Rt 6.47 min (purity 99.2%). LC/MS: 417.6 (M+H)⁺.

Example 36

5-(2'-methyl-2-nitrobiphenyl-4-yl)-3-[2-(trifluoromethoxy)phenyl]-1,2,4-oxadiazole

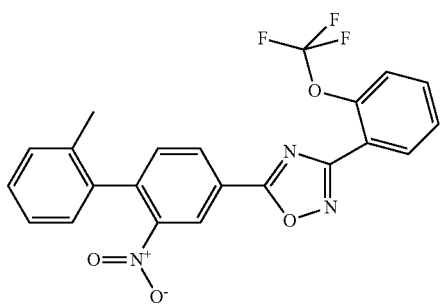 [SMILES: Cc1ccccc1-c1ccc(-c2nc(-c3ccccc3OC(F)(F)F)no2)cc1[N+](=O)[O-]]

Oxalyl chloride (118 μL; 1.40 mmol; 3 eq.), Intermediate 22 (120 mg; 0.47 mmol; 1 eq.), Intermediate 2 (103 mg; 0.47 mmol, 1 eq.) and DIEA (103 μL; 1.40 mmol; 3 eq.) were reacted according to general procedure 2. Purification by column chromatography c-hexane/ethyl acetate, 90/10) afforded the title compound as a yellow oil.

HPLC (Method A): Rt 6.13 min (purity 98.3%). LC/MS: 441.9 (M+H)⁺.

Example 37

N-dimethanesulfonyl-2-(3,3-difluoropiperidin-1-yl)-5-{3-[2-(methoxy)phenyl]-1,2,4-oxadiazol-5-yl}aniline

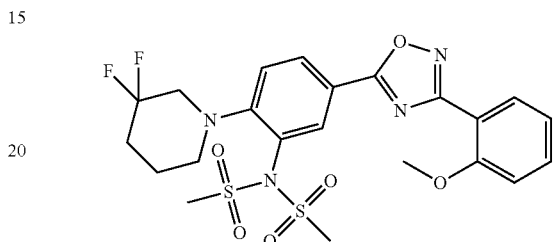

Step 1: 2-(3,3-difluoropiperidin-1-yl)-5-{3-[2-(methoxy)phenyl]-1,2,4-oxadiazol-5-yl}aniline Stannous chloride dihydrate (285 mg; 1.26 mmol; 5 eq.) was added to a solution of Example 12 (105 mg; 0.25 mmol; 1 eq.) in EtOH (20 mL) and the resulting mixture was stirred at 70° C. for 3 hours, then at room temperature for 16 hours. The solution was diluted with sat. aq. NaHCO₃ and extracted with ethyl acetate. The combined organic layer was washed with brine, dried over magnesium sulfate and concentrated in vacuo to afford the title compound (97 mg, 100%) as a yellow solid.

HPLC (Method A): Rt 4.61 min (purity 93.3%). LC/MS: 387.2 (M+H)⁺.

Step 2: N-dimethanesulfonyl-2-(3,3-difluoropiperidin-1-yl)-5-{3-[2-(methoxy)phenyl]-1,2,4-oxadiazol-5-yl}aniline Methanesulfonyl chloride (32 mg; 0.28 mmol; 1.2 eq.) was added dropwise to a suspension of 2-(3,3-difluoropiperidin-1-yl)-5-{3-[2-(trifluoromethoxy)phenyl]-1,2,4-oxadiazol-5-yl}aniline (90 mg; 0.23 mmol; 1 eq.) and DIEA (60 mg; 0.47 mmol; 2 eq.) in DCM (5 mL) and the resulting mixture was stirred at room temperature for 3 days. After evaporation of the solvent, the residue was purified by flash chromatography (c-hexane/ethyl acetate, 70/30) followed crystallization from Et₂O to afford the title compound as an off-white solid.

HPLC (Method A): Rt 4.73 min (purity 100%). LC/MS: 542.9 (M+H)⁺.

Example 38

5-[4-(2,5-dimethylpyrrolidin-1-yl)-3-nitrophenyl]-3-[2-(trifluoromethoxy)phenyl]-1,2,4-oxadiazole

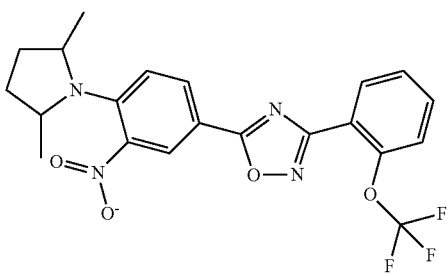

Oxalyl chloride (152 μL; 1.2 mmol; 3 eq.), Intermediate 25 (106 mg; 0.4 mmol; 1 eq.), Intermediate 2 (88 mg; 0.4 mmol, 1 eq.) and DIEA (155 μL; 1.2 mmol; 3 eq.) were reacted according to general procedure 2. Purification by crystallisation from ethyl acetate/n-pentane afforded the title compound as a yellow solid.

HPLC (Method A): Rt 6.15 min (purity 100%). LC/MS: 449.1 (M+H)⁺.

Example 39

5-[4-(2,5-dimethylpyrrolidin-1-yl)-3-nitrophenyl]-3-(5-fluoro-2-methoxyphenyl)-1,2,4-oxadiazole

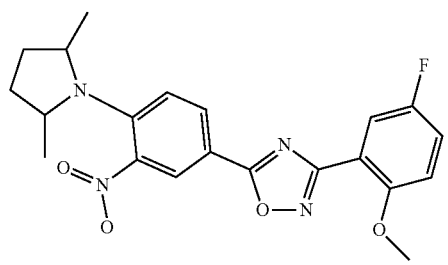

Oxalyl chloride (152 μL; 1.2 mmol; 3 eq.), Intermediate 25 (106 mg; 0.4 mmol; 1 eq.), Intermediate 23 (74 mg; 0.4 mmol, 1 eq.) and DIEA (155 μL; 1.2 mmol; 3 eq.) were reacted according to general procedure 2. Purification by crystallisation from ethyl acetate/n-pentane afforded the title compound as a yellow solid.

HPLC (Method A): Rt 5.54 min (purity 99.3%). LC/MS: 413.1 (M+H)⁺.

Example 40

5-(2'-methoxy-2-methylbiphenyl-4-yl)-3-(2-methoxyphenyl)-1,2,4-oxadiazole

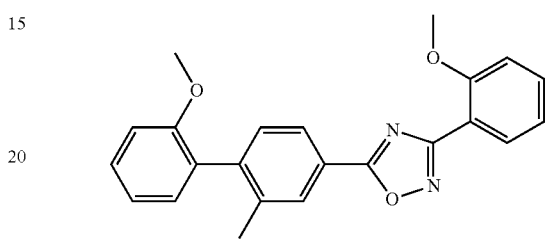

Oxalyl chloride (126 μL; 1.5 mmol; 3 eq.), Intermediate 26 (120 mg; 0.5 mmol; 1 eq.), Intermediate 1 (82 mg; 0.5 mmol, 1 eq.) and DIEA (256 μL; 1.5 mmol; 3 eq.) were reacted according to general procedure 2. Purification by column chromatography c-hexane/ethyl acetate, 90/10) followed by precipitation from n-pentane afforded the title compound as a white solid.

HPLC (Method A): Rt 5.51 min (purity 97.7%). LC/MS: 373.0 (M+H)⁺.

Example 41

2-(3,3-difluoropiperidin-1-yl)-5-{3-[2-(trifluoromethoxy)phenyl]-1,2,4-oxadiazol-5-yl}aniline

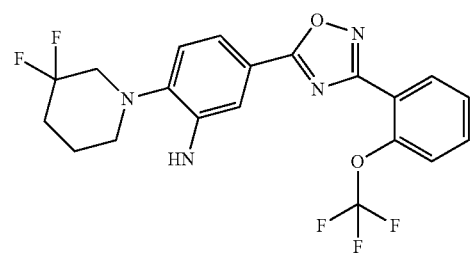 [SMILES: Nc1cc(-c2nc(-c3ccccc3OC(F)(F)F)no2)ccc1N1CCCC(F)(F)C1]

Stannous chloride dihydrate (478 mg; 2.13 mmol; 5 eq.) was added to a solution of Example 11 (200 mg; 0.43 mmol; 1 eq.) in EtOH (20 mL) and the resulting mixture was stirred at 70° C. for 3 hours, then at room temperature for 16 hours. The solution was diluted with sat. aq. NaHCO₃ and extracted with ethyl acetate. The combined organic layer was washed with brine, dried over magnesium sulfate and concentrated in vacuo. Purification by column chromatography (c-hexane/ethyl acetate, 70/30) followed by crystallization from n-pentane afforded the title compound as an off-white solid.

HPLC (Method A): Rt 5.54 min (purity 99.5%). LC/MS: 440.9 (M+H)⁺.

Example 42

5-[4-(2,5-dimethylpyrrolidin-1-yl)-3-nitrophenyl]-3-(2-methoxyphenyl)-1,2,4-oxadiazole

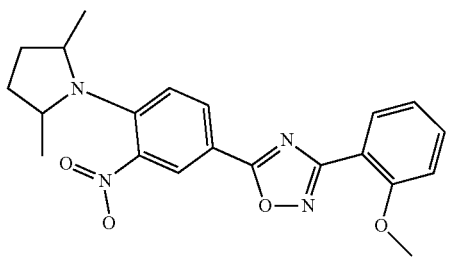

Oxalyl chloride (152 mg; 1.2 mmol; 3 eq.), Intermediate 25 (106 mg; 0.4 mmol; 1 eq.), Intermediate 1 (66 mg; 0.4 mmol, 1 eq.) and DIEA (155 mg; 1.2 mmol; 3 eq.) were reacted according to general procedure 2. Purification by precipitation from Et$_2$O/n-pentane afforded the title compound as a yellow solid.

HPLC (Method A): Rt 5.38 min (purity 99.1%). LC/MS: 394.9 (M+H)⁺.

Example 43

N-(2-(3,3-difluoropiperidin-1-yl)-5-{3-[2-(trifluoromethoxy)phenyl]-1,2,4-oxadiazol-5-yl}phenyl)methanesulfonamide

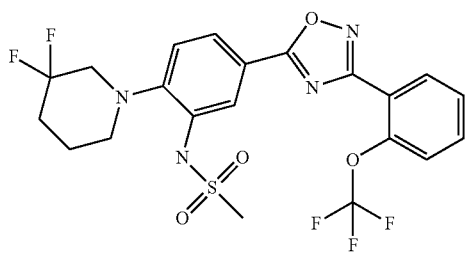 [SMILES: CS(=O)(=O)Nc1cc(-c2nc(-c3ccccc3OC(F)(F)F)no2)ccc1N1CCCC(F)(F)C1]

Methanesulfonylchloride (29.23 mg; 0.26 mmol; 0.6 eq.) was added to a solution of Example 41 (75 mg; 0.43 mmol; 1 eq.) in pyridine (1 mL) and the resulting solution was stirred at room temperature for 36 hours then concentrated in vacuo. The residue was purified by column chromatography (c-hexane/ethyl acetate, 70/30) followed by crystallization from ethyl acetate/n-pentane to afford the title compound as an off-white solid.

HPLC (Method A): Rt 5.31 min (purity 100%). LC/MS: 518.6 (M+H)⁺.

Example 44

5-[3-methyl-4-(4-methyl-3-thienyl)phenyl]-3-[2-(trifluoromethoxy)phenyl]-1,2,4-oxadiazole

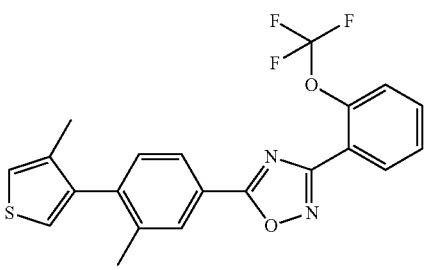 [SMILES: Cc1cc(-c2nc(-c3ccccc3OC(F)(F)F)no2)ccc1-c1cscc1C]

Oxalyl chloride (131 μL; 1.55 mmol; 3 eq.), Intermediate 20 (120 mg; 0.52 mmol; 1 eq.), Intermediate 2 (114 mg; 0.52 mmol, 1 eq.) and DIEA (267 μL; 1.55 mmol; 3 eq.) were reacted according to general procedure 2. Purification by column chromatography c-hexane/ethyl acetate, 95/5) afforded the title compound as a white solid.

HPLC (Method A): Rt 6.57 min (purity 91.5%). LC/MS: 417.0 (M+H)⁺.

Example 45

5-(2'-methoxy-2-methylbiphenyl-4-yl)-3-[2-(trifluoromethoxy)phenyl]-1,2,4-oxadiazole

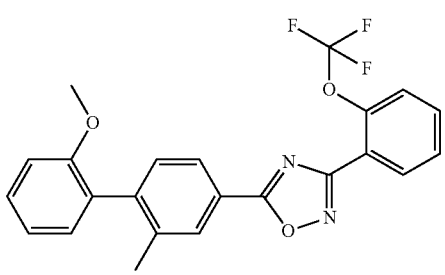 [SMILES: COc1ccccc1-c1ccc(-c2nc(-c3ccccc3OC(F)(F)F)no2)cc1C]

Oxalyl chloride (126 μL; 1.49 mmol; 3 eq.), Intermediate 26 (120 mg; 0.5 mmol; 1 eq.), Intermediate 2 (109 mg; 0.5 mmol, 1 eq.) and DIEA (256 μL; 1.49 mmol; 3 eq.) were reacted according to general procedure 2. Purification by column chromatography c-hexane/ethyl acetate, 95/5) afforded the title compound as a yellow oil.

HPLC (Method A): Rt 6.16 min (purity 90.6%). LC/MS: 427.0 (M+H)⁺.

HPLC (Method A): Rt 5.53 min (purity 98.1%). LC/MS: 403.1 (M+H)⁺.

Example 46

5-(2-methoxy-2'-methylbiphenyl-4-yl)-3-(2-methoxyphenyl)-1,2,4-oxadiazole

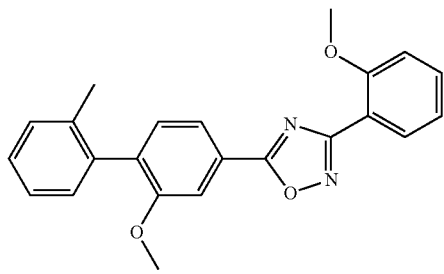 [SMILES: COc1ccccc1-c1noc(-c2ccc(-c3ccccc3C)c(OC)c2)n1]

Oxalyl chloride (126 µL; 1.49 mmol; 3 eq.), Intermediate 27 (120 mg; 0.5 mmol; 1 eq.), Intermediate 1 (82 mg; 0.5 mmol; 1 eq.) and DIEA (256 µL; 1.49 mmol; 3 eq.) were reacted according to general procedure 2. Purification by precipitation from DCM/n-pentane afforded the title compound as a brown solid.

HPLC (Method A): Rt 5.46 min (purity 95.9%). LC/MS: 372.9 (M+H)⁺.

Example 48

5-[3-methoxy-4-(4-methyl-3-thienyl)phenyl]-3-(2-methoxyphenyl)-1,2,4-oxadiazole

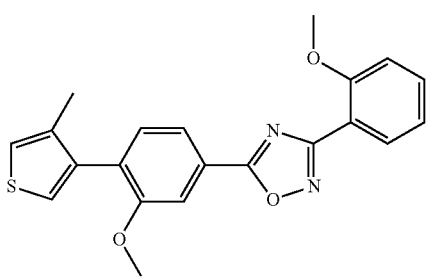

Oxalyl chloride (120 µL; 1.45 mmol; 3 eq.), Intermediate 29 (120 mg; 0.48 mmol; 1 eq.), Intermediate 1 (80 mg; 0.48 mmol; 1 eq.) and DIEA (250 µL; 1.45 mmol; 3 eq.) were reacted according to general procedure 2. Purification by precipitation from DCM/n-pentane afforded the title compound as a white solid.

HPLC (Method A): Rt 5.49 min (purity 96.4%). LC/MS: 378.9 (M+H)⁺.

Example 47

5-(2',4'-dimethoxy-2-methylbiphenyl-4-yl)-3-(2-methoxyphenyl)-1,2,4-oxadiazole

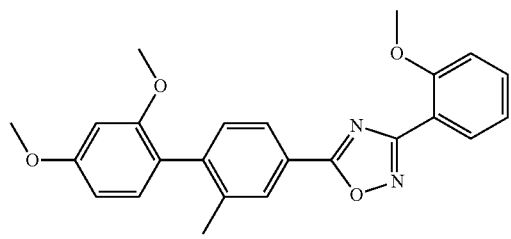 [SMILES: COc1ccc(-c2ccc(-c3nc(-c4ccccc4OC)no3)cc2C)c(OC)c1]

Oxalyl chloride (112 µL; 1.32 mmol; 3 eq.), Intermediate 28 (120 mg; 0.44 mmol; 1 eq.), Intermediate 1 (73 mg; 0.44 mmol; 1 eq.) and DIEA (228 µL; 1.32 mmol; 3 eq.) were reacted according to general procedure 2. Purification by precipitation from DCM/n-pentane afforded the title compound as a yellow solid.

Example 49

5-[4-(3,5-dimethylisoxazol-4-yl)-3-methylphenyl]-3-[2-(trifluoromethoxy)phenyl]-1,2,4-oxadiazole

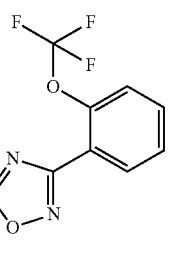

Oxalyl chloride (132 µL; 1.56 mmol; 3 eq.), Intermediate 30 (120 mg; 0.52 mmol; 1 eq.), Intermediate 2 (114 mg; 0.52 mmol; 1 eq.) and DIEA (268 µL; 1.56 mmol; 3 eq.) were reacted according to general procedure 2. Purification by column chromatography c-hexane/ethyl acetate, 80/20) afforded the title compound as a yellow oil.

HPLC (Method A): Rt 5.71 min (purity 96.7%). LC/MS: 415.9 (M+H)+.

HPLC (Method A): Rt 4.72 min (purity 96.6%). LC/MS: 447.1 (M+H)+.

Example 50

5-[4-(3,5-dimethylisoxazol-4-yl)-3-methylphenyl]-3-(2-methoxyphenyl)-1,2,4-oxadiazole

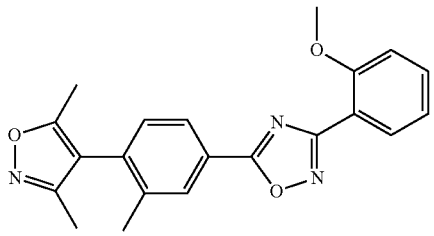 [SMILES: COc1ccccc1-c1noc(-c2ccc(-c3c(C)noc3C)c(C)c2)n1]

Oxalyl chloride (132 µL; 1.56 mmol; 3 eq.), Intermediate 30 (120 mg; 0.52 mmol; 1 eq.), Intermediate 1 (86 mg; 0.52 mmol, 1 eq.) and DIEA (268 µL; 1.56 mmol; 3 eq.) were reacted according to general procedure 2. Purification by column chromatography c-hexane/ethyl acetate, 80/20) afforded the title compound as an orange foam.

HPLC (Method A): Rt 4.85 min (purity 93.8%). LC/MS: 361.9 (M+H)+.

Example 52

N,N-bis(2-methoxyethyl)-4-[3-(2-methoxyphenyl)-1,2,4-oxadiazol-5-yl]-2-nitroaniline

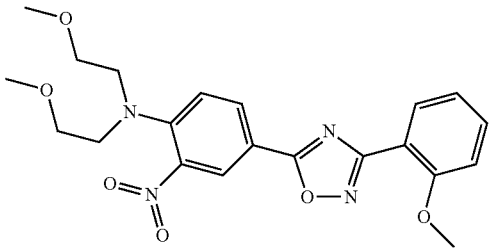

Oxalyl chloride (190 mg; 1.5 mmol; 3 eq.), Intermediate 31 (149 mg; 0.5 mmol; 1 eq.), Intermediate 1 (83 mg; 0.5 mmol, 1 eq.) and DIEA (194 mg; 1.5 mmol; 3 eq.) were reacted according to general procedure 2. Purification by column chromatography c-hexane/ethyl acetate, 50/50) followed by crystallisation from Et2O/n-pentane afforded the title compound as a yellow solid.

HPLC (Method A): Rt 4.55 min (purity 98.0%). LC/MS: 429.1 (M+H)+.

Example 51

4-[3-(5-fluoro-2-methoxyphenyl)-1,2,4-oxadiazol-5-yl]-N,N-bis(2-methoxyethyl)-2-nitroaniline

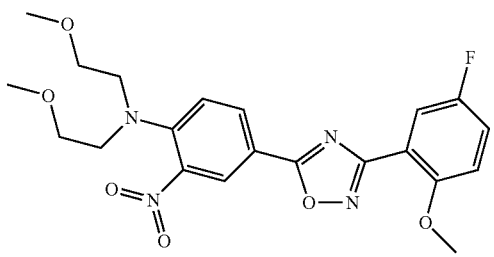 [SMILES: COCCN(CCOC)c1ccc(-c2nc(-c3cc(F)ccc3OC)no2)cc1[N+](=O)[O-]]

Oxalyl chloride (190 mg; 1.5 mmol; 3 eq.), Intermediate 31 (149 mg; 0.5 mmol; 1 eq.), Intermediate 23 (92 mg; 0.5 mmol, 1 eq.) and DIEA (194 mg; 1.5 mmol; 3 eq.) were reacted according to general procedure 2. Purification by column chromatography c-hexane/ethyl acetate, 50/50) followed by crystallisation from Et2O/n-pentane afforded the title compound as a yellow solid.

Example 53

5-(2-methoxy-2'-methylbiphenyl-4-yl)-3-[2-(trifluoromethoxy)phenyl]-1,2,4-oxadiazole

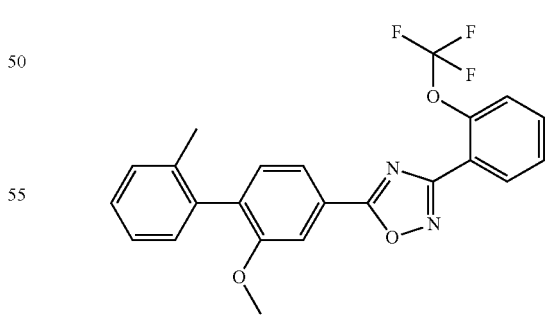

Oxalyl chloride (126 µL; 1.49 mmol; 3 eq.), Intermediate 27 (120 mg; 0.5 mmol; 1 eq.), Intermediate 2 (109 mg; 0.5 mmol, 1 eq.) and DIEA (256 µL; 1.5 mmol; 3 eq.) were reacted according to general procedure 2. Purification by column chromatography c-hexane/ethyl acetate, 95/5) afforded the title compound as a white solid.

HPLC (Method A): Rt 6.39 min (purity 98.0%). LC/MS: 427.0 (M+H)+.

Example 54

5-[3-methoxy-4-(4-methyl-3-thienyl)phenyl]-3-[2-(trifluoromethoxy)phenyl]-1,2,4-oxadiazole

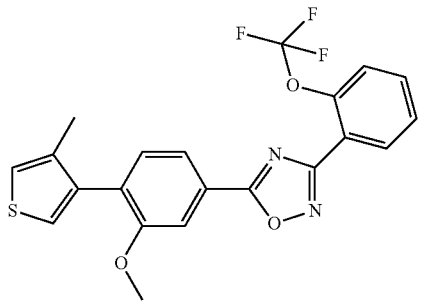 [SMILES: COc1cc(-c2nc(-c3ccccc3OC(F)(F)F)no2)ccc1-c1cscc1C]

Oxalyl chloride (123 µL; 1.45 mmol; 3 eq.), Intermediate 29 (120 mg; 0.48 mmol; 1 eq.), Intermediate 2 (106 mg; 0.48 mmol, 1 eq.) and DIEA (250 µL; 1.45 mmol; 3 eq.) were reacted according to general procedure 2. Purification by column chromatography c-hexane/ethyl acetate, 95/5) afforded the title compound as a yellow oil.

HPLC (Method A): Rt 6.15 min (purity 98.1%). LC/MS: 432.8 (M+H)+.

Example 55

5-[2'-methyl-2-(trifluoromethyl)biphenyl-4-yl]-3-[2-(trifluoromethoxy)phenyl]-1,2,4-oxadiazole

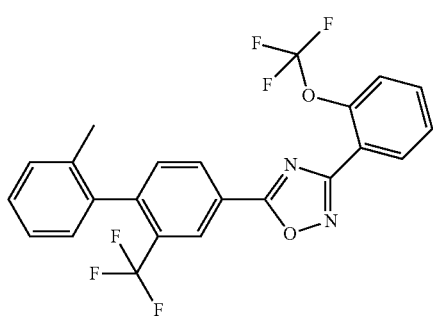 [SMILES: Cc1ccccc1-c1ccc(-c2nc(-c3ccccc3OC(F)(F)F)no2)cc1C(F)(F)F]

Oxalyl chloride (109 µL; 1.28 mmol; 3 eq.), Intermediate 34 (120 mg; 0.43 mmol; 1 eq.), Intermediate 2 (94 mg; 0.43 mmol, 1 eq.) and DIEA (221 µL; 1.28 mmol; 3 eq.) were reacted according to general procedure 2. Purification by column chromatography c-hexane/ethyl acetate, 95/5) afforded the title compound as a white solid.

HPLC (Method A): Rt 6.62 min (purity 97.8%). LC/MS: 464.7 (M+H)+.

Example 56

5-(2',4'-dimethoxy-2-methylbiphenyl-4-yl)-3-[2-(trifluoromethoxy)phenyl]-1,2,4-oxadiazole

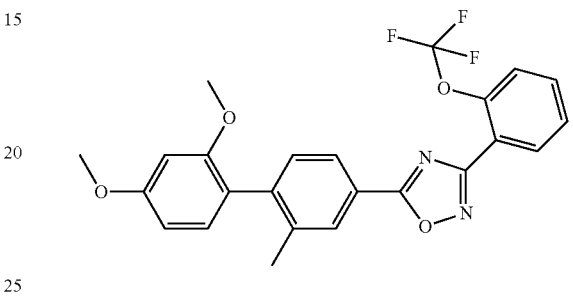

Oxalyl chloride (112 µL; 1.32 mmol; 3 eq.), Intermediate 28 (120 mg; 0.44 mmol; 1 eq.), Intermediate 2 (97 mg; 0.44 mmol, 1 eq.) and DIEA (228 µL; 1.32 mmol; 3 eq.) were reacted according to general procedure 2. Purification by column chromatography c-hexane/ethyl acetate, 95/5) afforded the title compound as a white solid.

HPLC (Method A): Rt 6.11 min (purity 96.3%). LC/MS: 457.0 (M+H)+.

Example 57

3-(2-methoxyphenyl)-5-[4-(4-methyl-3-thienyl)-3-(trifluoromethyl)phenyl]-1,2,4-oxadiazole

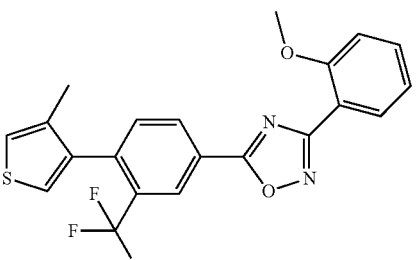

Oxalyl chloride (106 µL; 1.26 mmol; 3 eq.), Intermediate 32 (120 mg; 0.42 mmol; 1 eq.), Intermediate 1 (70 mg; 0.42 mmol, 1 eq.) and DIEA (217 µL; 1.26 mmol; 3 eq.) were reacted according to general procedure 2. Purification by column chromatography c-hexane/ethyl acetate, 95/5) followed by crystallization from n-pentane afforded the title compound as a yellow solid.

HPLC (Method A): Rt 5.77 min (purity 95.1%). LC/MS: 416.8 (M+H)⁺.

Example 58

1-(2-methyl-4-{3-[2-(trifluoromethoxy)phenyl]-1,2,4-oxadiazol-5-yl}phenyl)piperidine

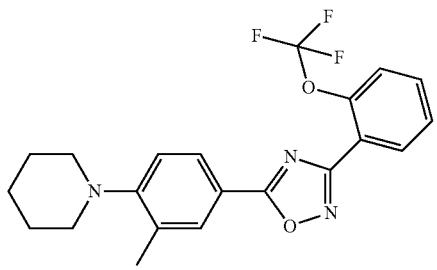 [SMILES: Cc1cc(-c2nc(-c3ccccc3OC(F)(F)F)no2)ccc1N1CCCCC1]

Oxalyl chloride (139 μL; 1.64 mmol; 3 eq.), Intermediate 33 (120 mg; 0.55 mmol; 1 eq.), Intermediate 2 (120 mg; 0.55 mmol, 1 eq.) and DIEA (283 μL; 1.64 mmol; 3 eq.) were reacted according to general procedure 2. Purification by column chromatography c-hexane/ethyl acetate, 95/5) afforded the title compound as a yellow oil.

HPLC (Method A): Rt 5.62 min (purity 93.2%). LC/MS: 404.0 (M+H)⁺.

Example 59

1-[4-[3-(2-methoxyphenyl)-1,2,4-oxadiazol-5-yl]-2-(trifluoromethyl)phenyl]piperidine

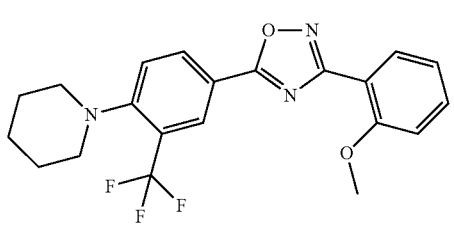 [SMILES: COc1ccccc1-c1noc(-c2ccc(N3CCCCC3)c(C(F)(F)F)c2)n1]

Oxalyl chloride (190 mg; 1.5 mmol; 3 eq.), Intermediate 42 (137 mg; 0.5 mmol; 1 eq.), Intermediate 1 (83 mg; 0.5 mmol, 1 eq.) and DIEA (194 mg; 1.5 mmol; 3 eq.) were reacted according to general procedure 2. Purification by crystallisation from n-pentane afforded the title compound as a white solid.

HPLC (Method A): Rt 6.05 min (purity 99.0%). LC/MS: 404.0 (M+H)⁺.

Example 60

1-[4-[3-(5-fluoro-2-methoxyphenyl)-1,2,4-oxadiazol-5-yl]-2-(trifluoromethyl)phenyl]piperidine

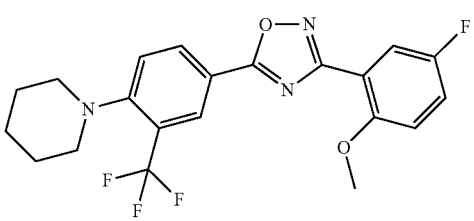 [SMILES: COc1ccc(F)cc1-c1noc(-c2ccc(N3CCCCC3)c(C(F)(F)F)c2)n1]

Oxalyl chloride (190 mg; 1.5 mmol; 3 eq.), Intermediate 42 (137 mg; 0.5 mmol; 1 eq.), Intermediate 23 (92 mg; 0.5 mmol, 1 eq.) and DIEA (194 mg; 1.5 mmol; 3 eq.) were reacted according to general procedure 2. Purification by crystallisation from n-pentane afforded the title compound as a white solid.

HPLC (Method A): Rt 6.20 min (purity 100%). LC/MS: 422.2 (M+H)⁺.

Example 61

1-[4-{3-[2-(trifluoromethoxy)phenyl]-1,2,4-oxadiazol-5-yl}-2-(trifluoromethyl)phenyl]piperidine

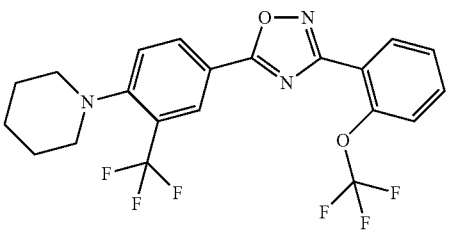 [SMILES: FC(F)(F)Oc1ccccc1-c1noc(-c2ccc(N3CCCCC3)c(C(F)(F)F)c2)n1]

Oxalyl chloride (190 mg; 1.5 mmol; 3 eq.), Intermediate 42 (137 mg; 0.5 mmol; 1 eq.), Intermediate 2 (92 mg; 0.5 mmol, 1 eq.) and DIEA (194 mg; 1.5 mmol; 3 eq.) were reacted according to general procedure 2. Purification by crystallisation from MeOH/water afforded the title compound as a white solid.

HPLC (Method A): Rt 6.74 min (purity 100%). LC/MS: 458.2 (M+H)+.

HPLC (Method A): Rt 6.77 min (purity 96.1%). LC/MS: 436.0 (M+H)+.

Example 62

3-(2-methoxyphenyl)-5-[2'-methyl-2-(trifluoromethyl)biphenyl-4-yl]-1,2,4-oxadiazole

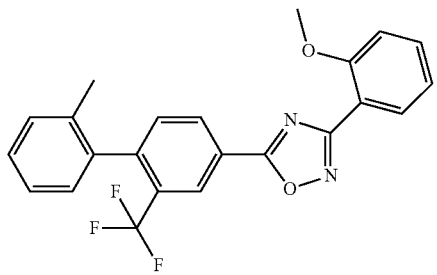 [SMILES: COc1ccccc1-c1noc(-c2ccc(-c3ccccc3C)c(C(F)(F)F)c2)n1]

Oxalyl chloride (109 μL; 1.28 mmol; 3 eq.), Intermediate 34 (120 mg; 0.43 mmol; 1 eq.), Intermediate 1 (71 mg; 0.43 mmol, 1 eq.) and DIEA (95 μL; 1.28 mmol; 3 eq.) were reacted according to general procedure 2. Purification by column chromatography c-hexane/ethyl acetate, 95/5) afforded the title compound as a white solid.

HPLC (Method A): Rt 5.86 min (purity 92.8%). LC/MS: 411.2 (M+H)+.

Example 64

4-{4-[3-(2-methoxyphenyl)-1,2,4-oxadiazol-5-yl]-2-methylphenyl}morpholine

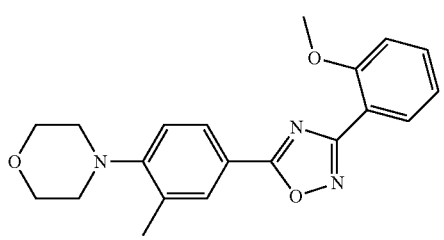

Oxalyl chloride (138 μL; 1.63 mmol; 3 eq.), Intermediate 35 (120 mg; 0.54 mmol; 1 eq.), Intermediate 1 (90 mg; 0.54 mmol, 1 eq.) and DIEA (280 μL; 1.63 mmol; 3 eq.) were reacted according to general procedure 2. Purification by column chromatography c-hexane/ethyl acetate, 95/5) afforded the title compound as a yellow solid.

HPLC (Method A): Rt 4.58 min (purity 99.4%). LC/MS: 352.2 (M+H)+.

Example 63

1-[4-[3-(5-fluoro-2-methoxyphenyl)-1,2,4-oxadiazol-5-yl]-2-(trifluoromethyl)phenyl]-2-methylpiperidine

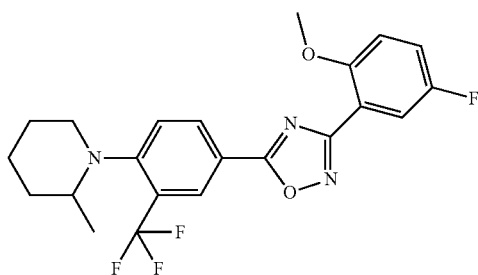 [SMILES: COc1ccc(F)cc1-c1noc(-c2ccc(N3CCCCC3C)c(C(F)(F)F)c2)n1]

Oxalyl chloride (106 μL; 1.25 mmol; 3 eq.), Intermediate 24 (120 mg; 0.42 mmol; 1 eq.), Intermediate 23 (77 mg; 0.42 mmol, 1 eq.) and DIEA (216 μL; 1.25 mmol; 3 eq.) were reacted according to general procedure 2. Purification by preparative HPLC (increasing amount of 0.1% TFA in CH3CN, in 0.1% TFA in water) afforded the title compound as a yellow solid.

Example 65

4-(2-methyl-4-{3-[2-(trifluoromethoxy)phenyl]-1,2,4-oxadiazol-5-yl}phenyl)morpholine

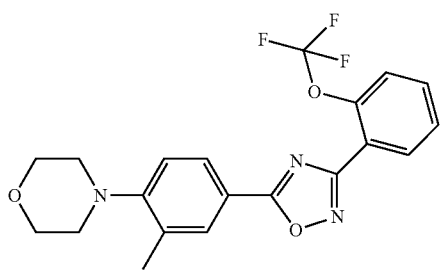 [SMILES: Cc1cc(-c2nc(-c3ccccc3OC(F)(F)F)no2)ccc1N1CCOCC1]

Oxalyl chloride (138 μL; 1.63 mmol; 3 eq.), Intermediate 35 (120 mg; 0.54 mmol; 1 eq.), Intermediate 2 (119 mg; 0.54 mmol, 1 eq.) and DIEA (280 μL; 1.63 mmol; 3 eq.) were reacted according to general procedure 2. Purification by column chromatography c-hexane/ethyl acetate, 90/10) afforded the title compound as a white solid.

HPLC (Method A): Rt 5.53 min (purity 93.4%). LC/MS: 406.2 (M+H)+.

Example 66

4-{4-[3-(5-fluoro-2-methoxyphenyl)-1,2,4-oxadiazol-5-yl]-2-methylphenyl}morpholine

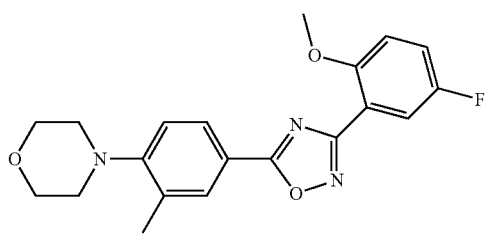 [SMILES: COc1ccc(F)cc1-c1noc(-c2ccc(N3CCOCC3)c(C)c2)n1]

Oxalyl chloride (138 µL; 1.63 mmol; 3 eq.), Intermediate 35 (120 mg; 0.54 mmol; 1 eq.), Intermediate 23 (100 mg; 0.54 mmol, 1 eq.) and DIEA (280 µL; 1.63 mmol; 3 eq.) were reacted according to general procedure 2. Purification by precipitation from DCM/c-hexane afforded the title compound as a yellow solid.

HPLC (Method A): Rt 4.78 min (purity 99.2%). LC/MS: 370.2 (M+H)+.

Example 67

1-{4-[3-(2-methoxyphenyl)-1,2,4-oxadiazol-5-yl]-2-methylphenyl}piperidine

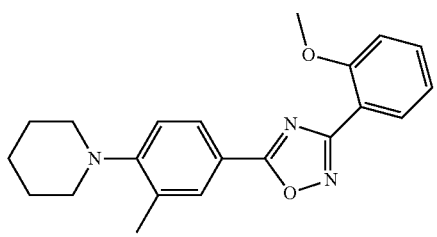 [SMILES: COc1ccccc1-c1noc(-c2ccc(N3CCCCC3)c(C)c2)n1]

Oxalyl chloride (139 µL; 1.64 mmol; 3 eq.), Intermediate 33 (120 mg; 0.55 mmol; 1 eq.), Intermediate 1 (91 mg; 0.55 mmol, 1 eq.) and DIEA (283 µL; 1.64 mmol; 3 eq.) were reacted according to general procedure 2. Purification by preparative HPLC (increasing amount of 0.1% TFA in CH₃CN, in 0.1% TFA in water) afforded the title compound as an orange solid.

HPLC (Method A): Rt 4.29 min (purity 100%). LC/MS: 350.2 (M+H)+.

Example 68

1-{4-[3-(5-fluoro-2-methoxyphenyl)-1,2,4-oxadiazol-5-yl]-2-methylphenyl}piperidine

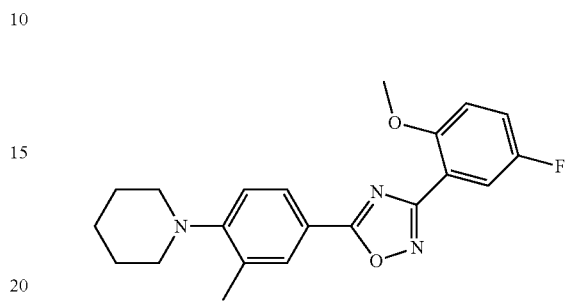

Oxalyl chloride (139 µL; 1.64 mmol; 3 eq.), Intermediate 33 (120 mg; 0.55 mmol; 1 eq.), Intermediate 23 (101 mg; 0.55 mmol, 1 eq.) and DIEA (283 µL; 1.64 mmol; 3 eq.) were reacted according to general procedure 2. Purification by preparative HPLC (increasing amount of 0.1% TFA in CH₃CN, in 0.1% TFA in water) afforded the title compound as a white solid.

HPLC (Method A): Rt 4.64 min (purity 100%). LC/MS: 368.2 (M+H)+.

Example 69

5-[3-(5-fluoro-2-methoxyphenyl)-1,2,4-oxadiazol-5-yl]-2-(2-methylpiperidin-1-yl)aniline

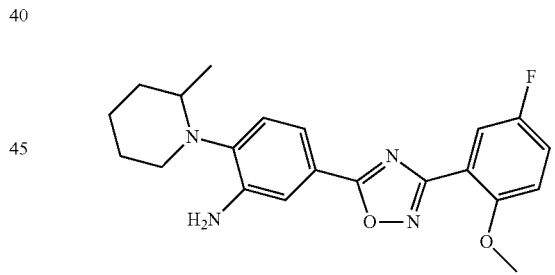

Oxalyl chloride (190 mg; 1.5 mmol; 3 eq.), Intermediate 8 (132 mg; 0.5 mmol; 1 eq.), Intermediate 23 (92 mg; 0.5 mmol; 1 eq.) and DIEA (194 mg; 1.5 mmol; 3 eq.) were reacted according to general procedure 2. After purification by column chromatography c-hexane/ethyl acetate, 80/20), the residue was taken up in EtOH (20 mL) and stannous chloride dihydrate (564 mg; 2.5 mmol; 5 eq.) was added. The resulting mixture was stirred at reflux for 3 hours then concentrated in vacuo. The residue was partitioned between NaOH 0.05M and ethyl acetate. The phases were separated and the organic layer was washed with brine, dried over magnesium and concentrated in vacuo. Purification by column chromatography (c-hexane/ethyl acetate, 75/25) afforded the title compound as an off-white solid.

HPLC (Method A): Rt 3.50 min (purity 97.7%). LC/MS: 383.3 (M+H)+.

Example 70

5-[4-(4-methyl-3-thienyl)-3-(trifluoromethyl)phenyl]-3-[2-(trifluoromethoxy)phenyl]-1,2,4-oxadiazole

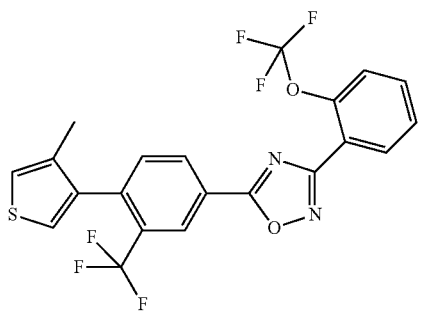 [SMILES: Cc1cscc1-c1ccc(-c2nc(-c3ccccc3OC(F)(F)F)no2)cc1C(F)(F)F]

Oxalyl chloride (106 μL; 1.26 mmol; 3 eq.), Intermediate 32 (120 mg; 0.42 mmol; 1 eq.), Intermediate 2 (92 mg; 0.42 mmol, 1 eq.) and DIEA (217 μL; 1.26 mmol; 3 eq.) were reacted according to general procedure 2. Purification by crystallisation from MeOH afforded the title compound as a white solid.

HPLC (Method A): Rt 6.57 min (purity 98.3%). LC/MS: 470.4 (M+H)+.

Example 71

5-[3-(5-fluoro-2-methoxyphenyl)-1,2,4-oxadiazol-5-yl]-2-(2-methylpiperidin-1-yl)benzonitrile

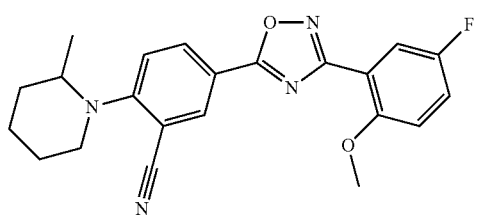 [SMILES: COc1ccc(F)cc1-c1noc(-c2ccc(N3CCCCC3C)c(C#N)c2)n1]

Oxalyl chloride (190 mg; 1.5 mmol; 3 eq.), Intermediate 36 (122 mg; 0.5 mmol; 1 eq.), Intermediate 23 (92 mg; 0.5 mmol, 1 eq.) and DIEA (194 mg; 1.5 mmol; 3 eq.) were reacted according to general procedure 2. Purification by column chromatography c-hexane/ethyl acetate, 70/30) afforded the title compound as a white solid.

HPLC (Method A): Rt 5.47 min (purity 96.7%). LC/MS: 393.2 (M+H)+.

Example 72

N-[5-[3-(5-fluoro-2-methoxyphenyl)-1,2,4-oxadiazol-5-yl]-2-(2-methylpiperidin-1-yl)phenyl]methanesulfonamide

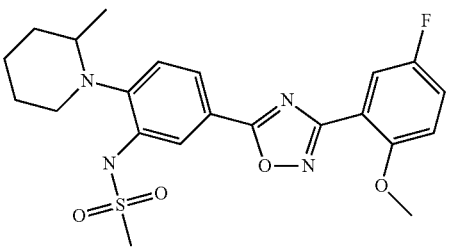 [SMILES: COc1ccc(F)cc1-c1noc(-c2ccc(N3CCCCC3C)c(NS(C)(=O)=O)c2)n1]

Methanesulfonyl chloride (20 μL; 0.26 mmol; 1.2 eq.) was added to a solution of Example 69 (83 mg; 0.22 mmol; 1 eq.) in pyridine (1 mL) and the resulting solution was stirred at room temperature for 16 hours. The solution was then partitioned between water and ethyl acetate. The two phases were separated and the aqueous layer was extracted with ethyl acetate. The combined organic phase was washed (3×) with 0.1M HCl, dried over magnesium sulfate and concentrated in vacuo. Purification by column chromatography c-hexane/ethyl acetate, 60/40) afforded the title compound as a white solid.

HPLC (Method A): Rt 4.93 min (purity 100%). LC/MS: 461.2 (M+H)+.

Example 73

3-{4-[3-(5-fluoro-2-methoxyphenyl)-1,2,4-oxadiazol-5-yl]-2-methylphenyl}-2-methylpyridine

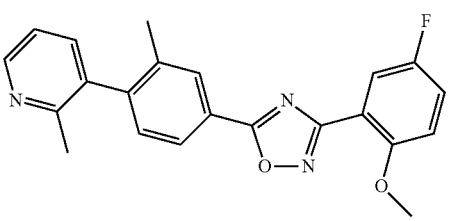 [SMILES: COc1ccc(F)cc1-c1noc(-c2ccc(-c3cccnc3C)c(C)c2)n1]

Oxalyl chloride (84 mg; 0.66 mmol; 3 eq.), Intermediate 37 (50 mg; 0.22 mmol; 1 eq.), Intermediate 23 (41 mg; 0.22 mmol, 1 eq.) and DIEA (85 mg; 0.66 mmol; 3 eq.) were reacted according to general procedure 2. Purification by column chromatography c-hexane/ethyl acetate, 90/10 then 85/15) afforded the title compound as a white solid.

HPLC (Method A): Rt 3.19 min (purity 94.2%). LC/MS: 376.3 (M+H)+.

Example 74

5-[3-(5-fluoro-2-methoxyphenyl)-1,2,4-oxadiazol-5-yl]-3-methyl-2-(2-methylpiperidin-1-yl)pyridine

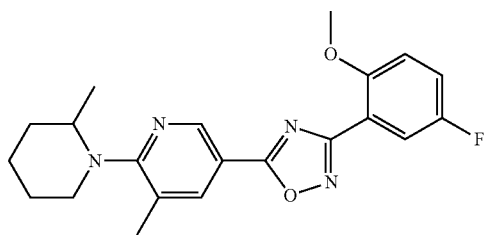 [SMILES: COc1ccc(F)cc1-c1noc(-c2cnc(N3CCCCC3C)c(C)c2)n1]

Oxalyl chloride (130 µL; 1.54 mmol; 3 eq.), Intermediate 38 (120 mg; 0.51 mmol; 1 eq.), Intermediate 23 (94 mg; 0.51 mmol, 1 eq.) and DIEA (260 µL; 1.54 mmol; 3 eq.) were reacted according to general procedure 2. Purification by column chromatography c-hexane/ethyl acetate, 50/50) afforded the title compound as a white solid.

HPLC (Method A): Rt 4.38 min (purity 88.7%). LC/MS: 383.3 (M+H)+.

Example 75

5-[3-(5-fluoro-2-methoxyphenyl)-1,2,4-oxadiazol-5-yl]-2-(2-methylpiperidin-1-yl)pyridine

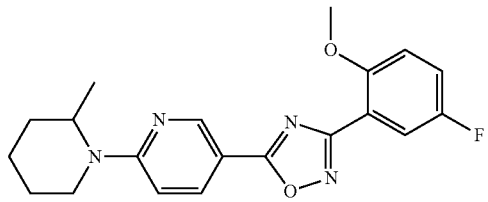 [SMILES: COc1ccc(F)cc1-c1noc(-c2ccc(N3CCCCC3C)nc2)n1]

Oxalyl chloride (138 µL; 1.63 mmol; 3 eq.), Intermediate 39 (120 mg; 0.54 mmol; 1 eq.), Intermediate 23 (100 mg; 0.54 mmol, 1 eq.) and DIEA (282 µL; 1.54 mmol; 3 eq.) were reacted according to general procedure 2. Purification by column chromatography c-hexane/ethyl acetate, 50/50) afforded the title compound as a yellow oil.

HPLC (Method A): Rt 3.92 min (purity 84.3%). LC/MS: 369.3 (M+H)+.

Example 76

5-[3-(5-fluoro-2-methoxyphenyl)-1,2,4-oxadiazol-5-yl]-2-[2-(methoxymethyl)pyrrolidin-1-yl]-3-methylpyridine

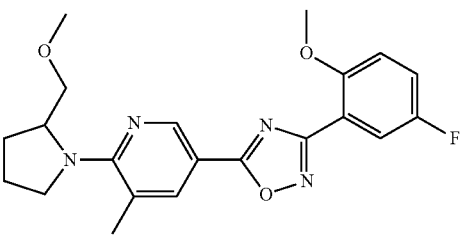 [SMILES: COCC1CCCN1c1ncc(-c2nc(-c3cc(F)ccc3OC)no2)cc1C]

Oxalyl chloride (122 µL; 1.44 mmol; 3 eq.), Intermediate 40 (120 mg; 0.48 mmol; 1 eq.), Intermediate 23 (88 mg; 0.48 mmol, 1 eq.) and DIEA (245 µL; 1.44 mmol; 3 eq.) were reacted according to general procedure 2. Purification by column chromatography c-hexane/ethyl acetate, 50/50) afforded the title compound as a yellow oil.

HPLC (Method A): Rt 3.49 min (purity 95.8%). LC/MS: 399.3 (M+H)+.

Example 77

{4-[3-(5-fluoro-2-methoxyphenyl)-1,2,4-oxadiazol-5-yl]-2'-methylbiphenyl-2-yl}methanol

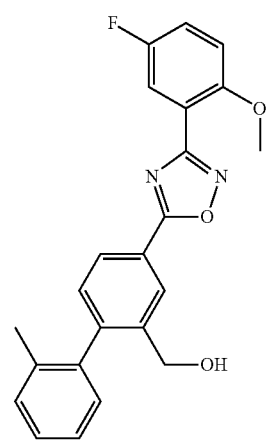 [SMILES: COc1ccc(F)cc1-c1noc(-c2ccc(-c3ccccc3C)c(CO)c2)n1]

Intermediate 23 (276 mg; 1.5 mmol; 1 eq.), Intermediate 41 (436 mg; 1.8 mmol; 1.2 eq.) and 1-ethyl-3-(3-dimethylaminopropyl)carbodiimide hydrochloride (345 mg; 1.8 mmol; 1.2 eq.) were dissolved in THF (6 mL) and acetonitrile (6 mL) and the reaction mixture was stirred at room temperature for 2 hours. DIEA (0.61 mL; 3.6 mmol; 2.4 eq.) was added and the mixture was heated in the microwave at 150° C. for 30 min. The reaction mixture was then filtered through a SPE-NH2 column (2 g) and through a SPE-SCX column (2 g) and rinsed with ACN. The filtrate was evaporated and the residue washed with ACN to afford the title compound as a white solid.

HPLC (Method A), Rt: 5.00 min (purity: 98.8%). LC/MS: 391.1 (M+H)+. $^1$H NMR (CDCl$_3$, 300 MHz) δ 8.45 (d, J=1.3 Hz, 1H), 8.18 (dd, J=7.9, 1.8 Hz, 1H), 7.91 (dd, J=9.0, 3.2 Hz, 1H), 7.35-7.13 (m, 6H), 7.03 (dd, J=9.2, 4.3 Hz, 1H), 4.51 (s, 2H), 4.00 (s, 3H), 2.08 (s, 3H), 1.61 (br s, 1H).

Example 78

1-{4-[3-(5-fluoro-2-methoxyphenyl)-1,2,4-oxadiazol-5-yl]-2'-methylbiphenyl-2-yl}-N,N-dimethylmethanamine

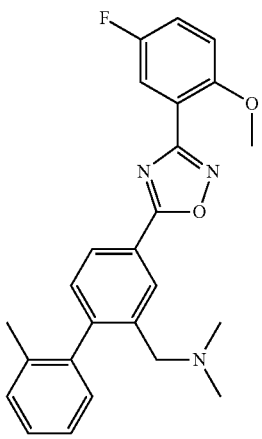 [SMILES: COc1ccc(F)cc1-c1noc(-c2ccc(-c3ccccc3C)c(CN(C)C)c2)n1]

To a solution of Example 77 (115 mg; 0.29 mmol; 1 eq.) in DCM (6 mL) is added at 0° C. N-ethyldiisopropylamine (250 µL; 1.47 mmol; 5 eq.) and methanesulfonyl chloride (27 µL; 0.35 mmol; 1.2 eq.). After 15 min, dimethylamine (2M; 440 µL; 0.88 mmol; 3 eq.) was added and the reaction mixture stirred at room temperature for 2 hours. Water (5 mL) was added and the organic layer washed with water. The organic phase was dried over magnesium sulfate and concentrated in vacuo. The residue was purified by mass triggered preparative HPLC (increasing amount of ACN in water) to afford the title compound as a brown oil.

HPLC (Method A), Rt: 3.81 min (purity: 98.9%). LC/MS: 418.2 (M+H)+. $^1$H NMR (DMSO-d$_6$, 300 Hz) δ 8.37 (s, 1H), 8.01 (d, J=8.0 Hz, 1H), 7.77 (d, J=7.8 Hz, 1H), 7.50-7.45 (m, 1H), 7.39-7.29 (m, 5H), 7.11 (d, J=6.8 Hz, 1H), 3.91 (s, 3H), 3.18 (s, 2H), 2.07 (s, 6H), 2.01 (s, 3H).

Example 79

4-[3-(5-fluoro-2-methoxyphenyl)-1,2,4-oxadiazol-5-yl]-2'-methylbiphenyl-2-carboxylic acid

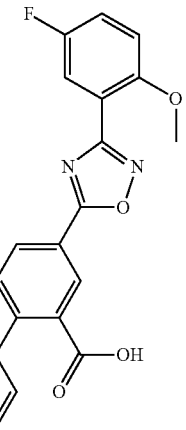

Step 1: 4-[3-(5-fluoro-2-methoxyphenyl)-1,2,4-oxadiazol-5-yl]-2'-methylbiphenyl-2-carbaldehyde Manganese(IV) oxide (111 mg; 1.28 mmol; 10 eq.) was added to a solution of Example 77 (50 mg; 0.13 mmol; 1 eq.) in DCM (5 mL) and the reaction mixture was stirred at room temperature for 4 hours. The suspension was filtered through a pad of CELITE and the solution concentrated in vacuo to afford title compound (46 mg; 93%) as a white solid.

HPLC (Method A), Rt: 5.48 min (purity: 98.7%). LC/MS: 389.2 (M+H)+.

Step 2: 4-[3-(5-fluoro-2-methoxyphenyl)-1,2,4-oxadiazol-5-yl]-2'-methylbiphenyl-2-carboxylic acid A solution of sodium chlorite (59 mg; 0.65 mmol; 5.5 eq.) and sodium dihydrogenphosphate (51 mg; 0.43 mmol; 3.6 eq.) in water (1 mL) was added to a mixture of 2-methyl-2-butene (0.13 mL) and 4-[3-(5-fluoro-2-methoxyphenyl)-1,2,4-oxadiazol-5-yl]-2'-methylbiphenyl-2-carbaldehyde (46.2 mg; 0.12 mmol; 1 eq.) in dioxane (1 mL) and the reaction was stirred at room temperature for 16 hours. The suspension was partitioned between water and ethyl acetate. The aqueous phase was acidified to pH 3-4 with acetic acid and extracted with ethyl acetate. The combined organic phase was washed with brine, dried over magnesium sulfate and concentrated in vacuo to afford the title compound (43 mg; 89%) as a white solid.

HPLC (Method A), Rt: 5.19 min (purity: 99.7%). LC/MS: 405.2 (M+H)+. $^1$H NMR (DMSO-d$_6$, 300 MHz) δ 13.09 (br s, 1H), 8.59 (d, J=1.8 Hz, 1H), 8.34 (dd, J=8.0, 1.9 Hz, 1H), 7.80 (dd, J=9.0, 3.2 Hz, 1H), 7.53 (d, J=8.0 Hz, 1H), 7.50-7.44 (m, 1H), 7.33-7.21 (m, 4H), 7.10 (d, J=7.0 Hz, 1H), 3.92 (s, 3H), 2.07 (s, 3H).

Example 80

In Vitro Assays

Receptor binding assay: Membranes were prepared from CHO cells expressing S1P$_1$ or S1P$_3$ for use in ligand and 355-GTPγS binding studies. Cells were suspended in 50 mM TRIS, pH 7.4, 2 mM EDTA, 250 mM Sucrose (buffer A) and 1× Complete protease inhibitor cocktail (Roche), and disrupted at 4° C. by nitrogen decompression using a cell disruption bomb (Parr Instrument). Following centrifugation at 1000 RPM for 10 min at 4° C., the supernatant was suspended in buffer A and centrifuged again at 19000 RPM for 60 min at 4° C. The pellet was then suspended in 10 mM HEPES, pH 7.4, 1 mM EDTA, 250 mM Sucrose (Buffer B), and 1× Complete EDTA-free protease inhibitor cocktail and homogenized using a potter. Membranes were flash frozen in liquid nitrogen and stored at −80° C. [33P]sphingosine 1-phosphate (3000 Ci/mmol; American Radiolabeled Chemicals, Inc.) was added to test compounds in DMSO. Membranes and WGA SPA beads (GE Healthcare) were added to give a final volume of 100 µl in 96-well plates with assay concentrations of 25 pM or 10 pM [33P]sphingosine 1-phosphate (respectively for S1P1 or S1P3), 50 mM HEPES, pH 7.5, 5 mM MgCl2, 100 mM NaCl, 0.4% fatty acid-free BSA, 1-5 µg/well of proteins and 100 µg/well of WGA SPA beads. Binding was performed for 60 min at room temperature on a shaker and bound radioactivity was measured on a PerkinElmer 1450 MicroBeta counter. Specific binding was calculated by subtracting remaining radioactivity in the presence of 1000-fold excess of unlabeled S1P. Binding data were analyzed using the GraphPad Prism program.

Measurements of $^{35}$S-GTPγS Binding: Membranes (1 to 10 µg protein) prepared as described above, were incubated in 96-well Scintiplates (PerkinElmer) with test compounds diluted in DMSO, in 180 µl of 20 mM HEPES, pH 7.4, 10 mM $MgCl_2$, 2 µg/well Saponin, 0.2% fatty acid free BSA (Assay buffer), 140 mM NaCl and 1.7 µM GDP. The assay was initiated with the addition of 20 µl of 1.5 nM [35S]-GTPγS (1100 Ci/mmol; GE Healthcare) in assay buffer. After 60 min incubation at 30° C. on a shaker, plates were centrifuged for 10 min at 2000 RPM. Supernatant was discarded and membrane bound radioactivity was measured on a PerkinElmer 1450 MicroBeta counter. Triplicate samples were averaged and expressed as % response relative to S1P activation in absence of compound (n=2).

The compound of formula (I) have utility as immunoregulatory agents as demonstrated by their activity as potent and selective agonists of the $S1P_1$ receptor over the $S1P_3$ receptor as measured in the assays described above. In particular, the examples disclosed herein possess a selectivity for the S1P1 receptor over the S1P3 receptor as measured by the ratio of EC50 for the S1P1 receptor to the EC50 for the $S1P_3$ receptor as evaluated in the $^{35}$S-GTPγS binding assay described above. The following results have been obtained:

| Compound | $S1P_1$ Binding Ki (µM) | $S1P_1$ GTPgS EC50 (µM) | $S1P_3$ GTPgs EC50 (µM) |
|---|---|---|---|
| I1 | 0.011 | 0.027 | >20 |
| I2 | 0.018 | 0.051 | >30 |
| I3 | 0.652 | 1.785 | — |
| I4 | 1.074 | 3.605 | — |

-continued
| Compound | | S1P$_1$ Binding Ki (μM) | S1P$_1$ GTPgS EC50 (μM) | S1P$_3$ GTPgs EC50 (μM) |
|---|---|---|---|---|
| I5 | 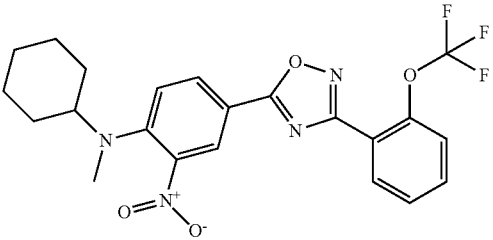 [SMILES: CN(c1ccc(-c2nc(-c3ccccc3OC(F)(F)F)no2)cc1[N+](=O)[O-])C1CCCCC1] | — | 0.589 | — |
| I6 | 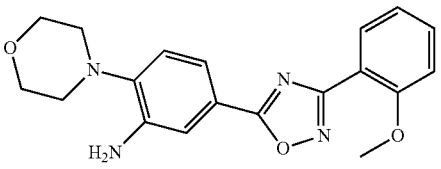 [SMILES: COc1ccccc1-c1noc(-c2ccc(N3CCOCC3)c(N)c2)n1] | — | 0.712 | — |
| I7 | 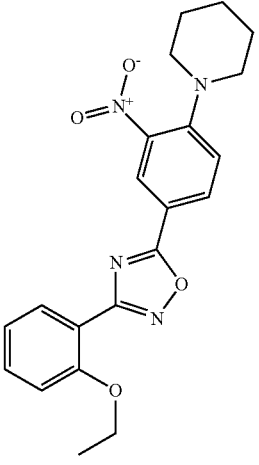 [SMILES: CCOc1ccccc1-c1noc(-c2ccc(N3CCCCC3)c([N+](=O)[O-])c2)n1] | — | 0.254 | — |
| I8 | 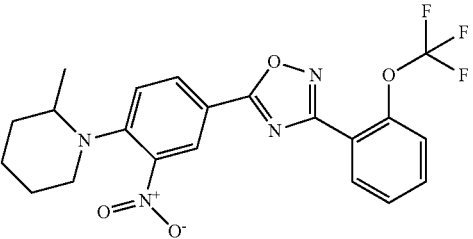 [SMILES: CC1CCCCN1c1ccc(-c2nc(-c3ccccc3OC(F)(F)F)no2)cc1[N+](=O)[O-]] | — | 0.018 | >30 |
| I9 | 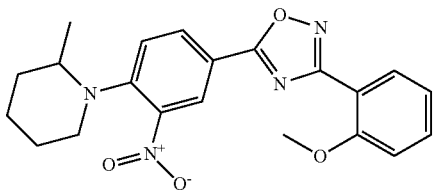 [SMILES: COc1ccccc1-c1noc(-c2ccc(N3CCCCC3C)c([N+](=O)[O-])c2)n1] | — | 0.007 | 5.410 |

-continued

| Compound | | S1P₁ Binding Ki (μM) | S1P₁ GTPgS EC50 (μM) | S1P₃ GTPgs EC50 (μM) |
|---|---|---|---|---|
| I10 | | — | 0.024 | >30 |
| I11 | | — | 0.080 | — |
| I12 | | — | 0.036 | >30 |
| I13 | | — | 0.132 | — |
| I14 | | — | 0.428 | — |
| I15 | | — | 1.130 | — |

-continued
| Compound | | S1P$_1$ Binding Ki (μM) | S1P$_1$ GTPgS EC50 (μM) | S1P$_3$ GTPgs EC50 (μM) |
|---|---|---|---|---|
| I16 | 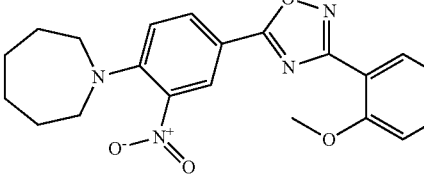 | — | 0.228 | — |
| I17 | 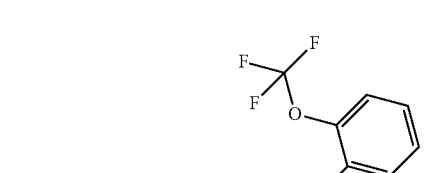 | — | 0.135 | — |
| I18 | 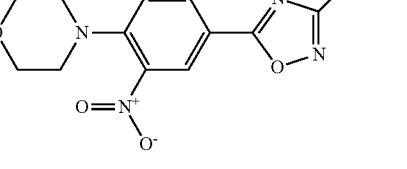 | 0.007 | 0.006 | >30 |
| I19 | 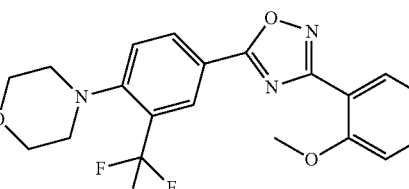 | — | 0.018 | >30 |
| I20 | 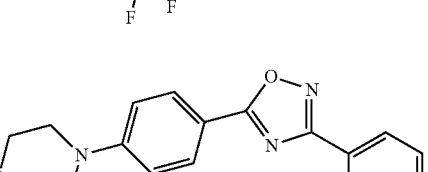 | 0.016 | 0.044 | 3.210 |
| I21 | 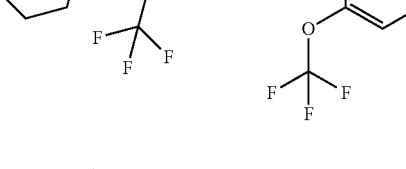 | 0.008 | 0.004 | >30 |

-continued

| Compound | | S1P₁ Binding Ki (μM) | S1P₁ GTPgS EC50 (μM) | S1P₃ GTPgs EC50 (μM) |
|---|---|---|---|---|
| I22 | | — | 0.051 | >30 |
| I23 | | 0.016 | 0.010 | >30 |
| I24 | | — | 0.057 | — |
| I25 | | 0.003 | 0.009 | 5.485 |
| I26 | | 0.002 | 0.009 | 5.050 |

-continued
| Compound | | S1P$_1$ Binding Ki (μM) | S1P$_1$ GTPgS EC50 (μM) | S1P$_3$ GTPgs EC50 (μM) |
|---|---|---|---|---|
| I27 | 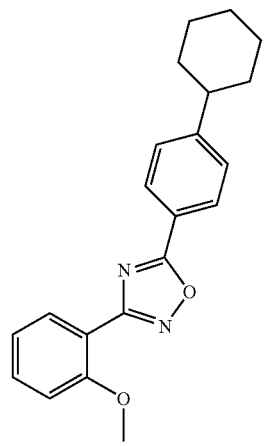 | 0.020 | 0.066 | >30 |
| I28 | 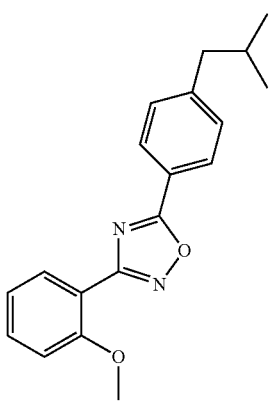 | 0.091 | 0.162 | >30 |
| I29 | 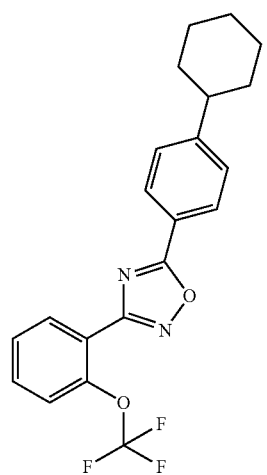 | 0.025 | 0.059 | — |

-continued
| Compound | | S1P₁ Binding Ki (μM) | S1P₁ GTPgS EC50 (μM) | S1P₃ GTPgs EC50 (μM) |
|---|---|---|---|---|
| I30 | 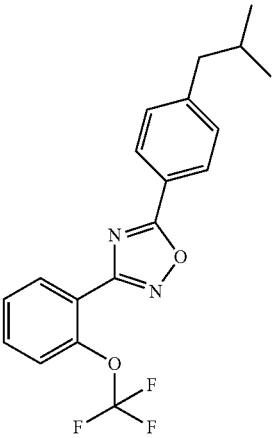 | — | 0.064 | — |
| I31 | 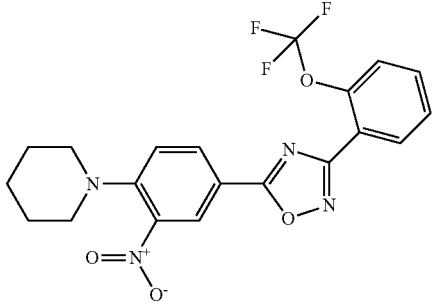 | — | 0.058 | — |
| I32 | 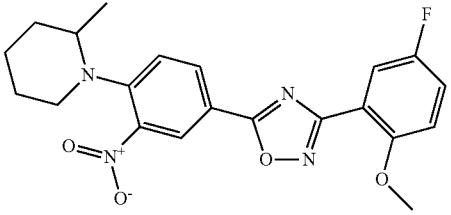 | 0.001 | 0.002 | 1.705 |
| I33 | 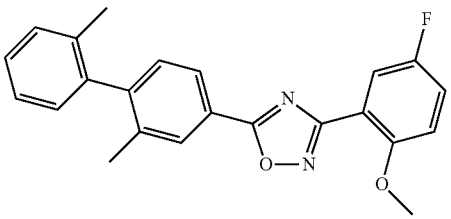 | 0.043 | 0.006 | — |
| I34 | 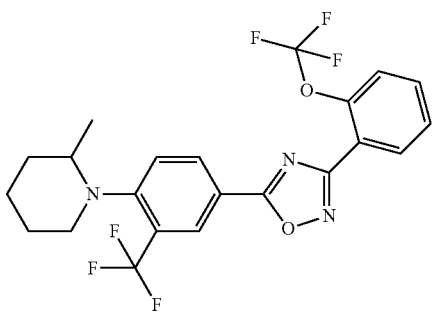 | 0.005 | 0.006 | >20 |

-continued

| Compound | S1P₁ Binding Ki (μM) | S1P₁ GTPgS EC50 (μM) | S1P₃ GTPgs EC50 (μM) |
|---|---|---|---|
| I35 | 0.003 | 0.002 | 0.650 |
| I36 | — | 0.010 | 2.100 |
| I37 | — | 0.921 | — |
| I38 | — | 4.470 | — |
| I39 | — | 0.267 | — |

-continued
| Compound | | S1P₁ Binding Ki (μM) | S1P₁ GTPgS EC50 (μM) | S1P₃ GTPgs EC50 (μM) |
|---|---|---|---|---|
| I40 | 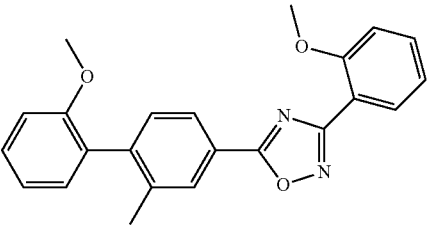 | — | 0.027 | — |
| I41 | 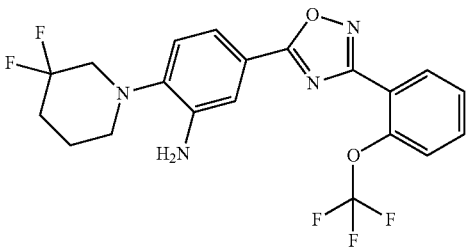 | — | 0.116 | — |
| I42 | 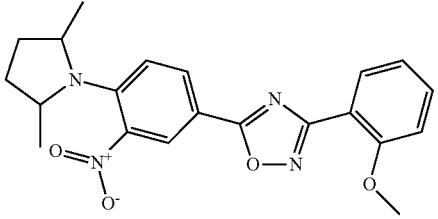 | — | 1.251 | — |
| I43 | 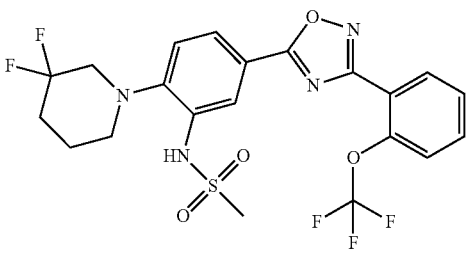 | — | 0.039 | — |
| I44 | 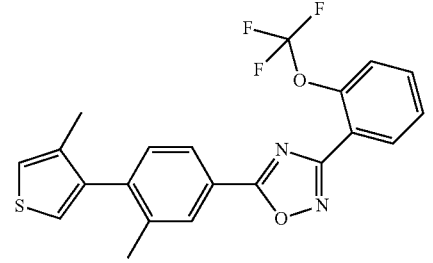 | 0.005 | 0.003 | >20 |
| I45 | 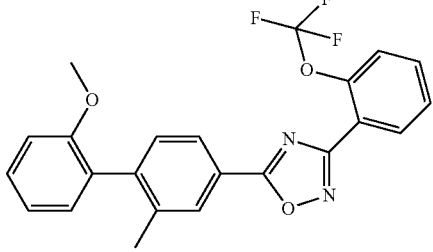 | — | 0.010 | >20 |

-continued
| Compound | S1P₁ Binding Ki (μM) | S1P₁ GTPgS EC50 (μM) | S1P₃ GTPgs EC50 (μM) |
|---|---|---|---|
| I46 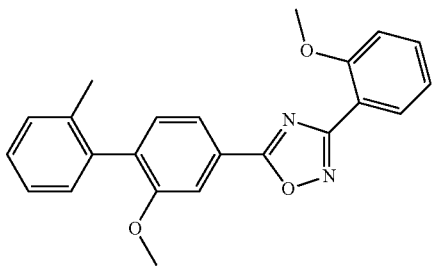 | — | 0.033 | — |
| I47 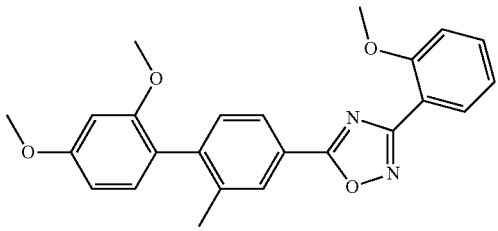 | — | 1.200 | — |
| I48 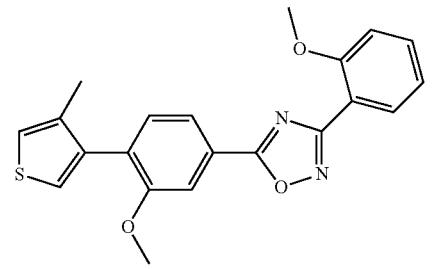 | 0.004 | 0.005 | 2.180 |
| I49 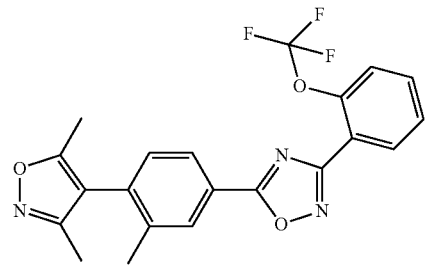 | — | 0.191 | — |
| I50 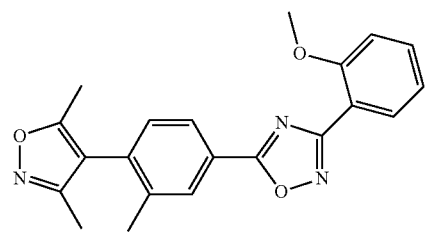 | — | 0.172 | — |

-continued
| Compound | | S1P₁ Binding Ki (μM) | S1P₁ GTPgS EC50 (μM) | S1P₃ GTPgs EC50 (μM) |
|---|---|---|---|---|
| I51 | 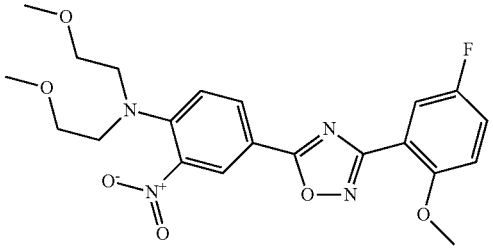 | — | 0.085 | — |
| I52 | 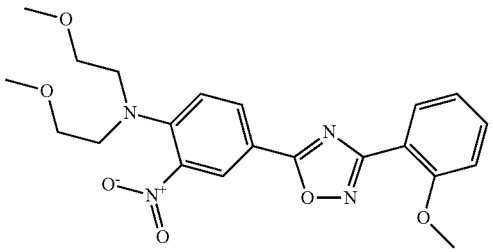 | — | 0.295 | — |
| I53 | 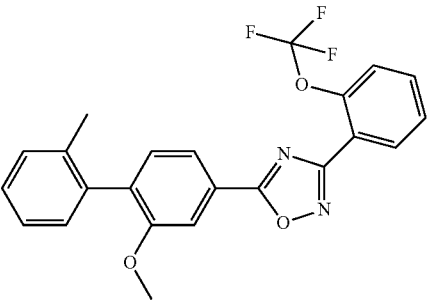 | — | 0.014 | >20 |
| I54 | 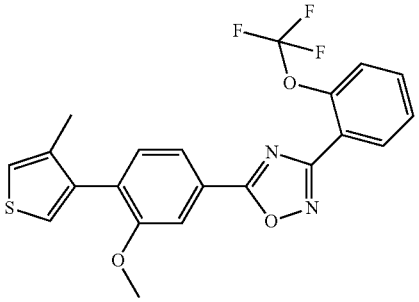 | — | 0.013 | >30 |
| I55 | 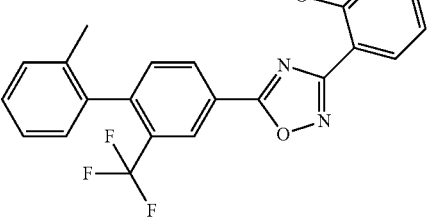 | 0.008 | 0.002 | >30 |

-continued
| Compound | | S1P$_1$ Binding Ki (μM) | S1P$_1$ GTPgS EC50 (μM) | S1P$_3$ GTPgs EC50 (μM) |
| --- | --- | --- | --- | --- |
| I56 | 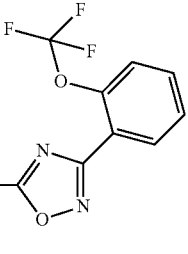 | — | 0.302 | — |
| I57 | 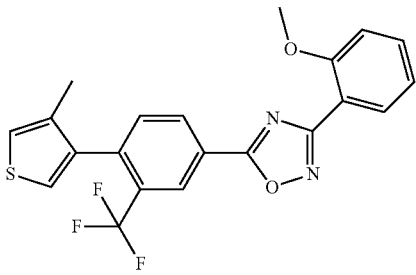 | 0.002 | 0.001 | >20 |
| I58 | 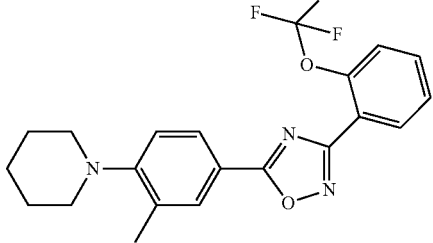 | — | 0.039 | — |
| I59 | 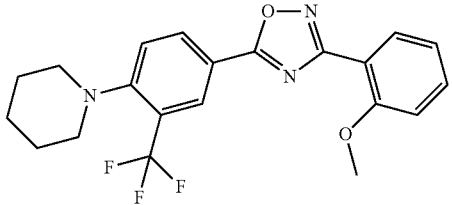 | — | 0.021 | — |
| I60 | 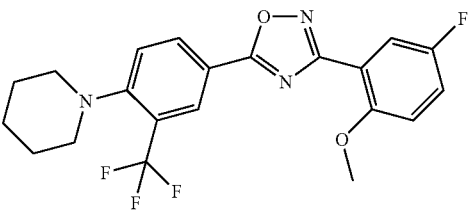 | 0.001 | 0.002 | 0.617 |
| I61 | 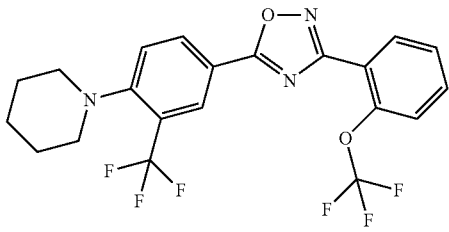 | 0.054 | 0.004 | — |

-continued

| Compound | | S1P$_1$ Binding Ki (μM) | S1P$_1$ GTPgS EC50 (μM) | S1P$_3$ GTPgs EC50 (μM) |
|---|---|---|---|---|
| I62 | | 0.008 | 0.004 | — |
| I63 | | 0.003 | 0.001 | 0.125 |
| I64 | | — | 0.098 | — |
| I65 | | — | 0.130 | — |
| I66 | | — | 0.028 | — |
| I67 | | — | 0.024 | — |

-continued

| Compound | | S1P₁ Binding Ki (μM) | S1P₁ GTPgS EC50 (μM) | S1P₃ GTPgs EC50 (μM) |
|---|---|---|---|---|
| I68 | (structure) | — | 0.010 | — |
| I69 | (structure) | — | 0.024 | 0.270 |
| I70 | (structure) | 0.004 | 0.002 | — |
| I71 | (structure) | 0.004 | 0.001 | 0.074 |
| I72 | (structure) | 0.046 | 0.008 | >20 |
| I73 | (structure) | — | 0.341 | — |

-continued

| Compound | | S1P₁ Binding Ki (μM) | S1P₁ GTPgS EC50 (μM) | S1P₃ GTPgs EC50 (μM) |
|---|---|---|---|---|
| I74 | [structure] | 0.006 | 0.005 | — |
| I75 | [structure] | — | 1.185 | — |
| I76 | [structure] | — | 0.522 | — |
| I77 | [structure] | 0.053 | 0.065 | 5.61 |
| I78 | [structure] | 0.004 | 0.002 | 0.092 |
| I79 | [structure] | — | 0.657 | — |

Example 32

Animal Models Evaluating the In Vivo Efficacy of S1P Agonists

Model of S1P Agonists-Induced Lymphopenia in Mice

Female C57BL/6 mice (Elevage Janvier) (8 week old) receive S1P agonists by oral route. Blood is sampled in heparinized (100 IU/kg, ip) mice by intracardiac or retroorbital puncture under isoflurane anesthesia 2 to 120 hrs after drug treatment. The white blood cells (lymphocytes and neutrophils) are counted using a Beckman/Coulter counter. The quality of blood sampling is assessed by counting erythrocytes and platelets.

Model of MOG-Induced Experimental Autoimmune Encephalomyelytis (EAE) in Mice

EAE was induced in 9 weeks old female mice (C57BL/6, Elevage Janvier) by an immunization against MOG. The mice received Pertussis toxin (Alexis, 300 ng/mouse in 200 µl of PBS) by ip route and 100 µl of an emulsion containing MOG35-55 peptide (NeoMPS, 200 µg/mouse), *Mycobacterium Tuberculosis* (0.25 mg/mouse) in Complete Freund's Adjuvant (DIFCO) by subcutaneous injection into the back. Two days later an additional injection of Pertussis toxin (Alexis, 300 ng/mouse in 200 µl of PBS) was done by ip route. After EAE induction, mice were weighed daily and the neurological impairment was quantified using a 15-points clinical scale assessing the paralysis (tail, hind limbs and fore limbs), the incontinency and the death.

Clinical Score

1—Tail

Score=0 A normal mouse holds its tail erect when moving.

Score=1 If the extremity of the tail is flaccid with a tendency to fall.

Score=2 If the tail is completely flaccid and drags on the table.

2—Hind Limbs

Score=0 A normal mouse has an energetic walk and doesn't drag his paws.

Score=1 Either one of the following tests is positive:

a—Flip test: while holding the tail between thumb and index finger, flip the animal on his back and observe the time it takes to right itself. A healthy mouse will turn itself immediately. A delay suggests hind-limb weakness.

b—Place the mouse on the wire cage top and observe as it crosses from one side to the other. If one or both limbs frequently slip between the bars we consider that there is a partial paralysis.

Score=2 Both previous tests are positive.

Score=3 One or both hind limbs show signs of paralysis but some movements are preserved; for example: the animal can grasp and hold on to the underside of the wire cage top for a short moment before letting go Score=4 When both hind legs are paralyzed and the mouse drags them when moving.

3—Fore Limbs:

Score=0 A normal mouse uses his front paws actively for grasping and walking and holds his head erect.

Score=1 Walking is possible but difficult due to a weakness in one or both of the paws, for example, the front paws are considered weak when the mouse has difficulty grasping the underside of the wire top cage. Another sign of weakness is head drooping.

Score=2 When one forelimb is paralyzed (impossibility to grasp and the mouse turns around the paralyzed limb). At this time the head has also lost much of its muscle tone.

Score=3 Mouse cannot move, and food and water are unattainable.

4—Bladder:

Score=0 A normal mouse has full control of his bladder.

Score=1 A mouse is considered incontinent when his lower body is soaked with urine.

5—Death:

Score=15

The final score for each animal is determined by the addition of all the above-mentioned categories. The maximum score for live animals is 10.

At day 12 (first signs of paralysis) the mice were stratified in experimental groups (n=10) according to the clinical score and the body weight loss. The semi-curative treatment started at day 14.

Example A

Injection Vials

A solution of 100 g of an active ingredient of the formula I and 5 g of disodium hydrogenphosphate in 3 L of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C

Solution

A solution is prepared from 1 g of an active ingredient of the formula (I), 9.38 g of $NaH_2PO_4.2H_2O$, 28.48 g of $Na_2HPO_4.12H_2O$ and 0.1 g of benzalkonium chloride in 940 mL of bidistilled water. The pH is adjusted to 6.8, and the solution is made up to 1 L and sterilised by irradiation. This solution can be used in the form of eye drops.

Example D

Ointment 500 mg of an active ingredient of the formula (I) are mixed with 99.5 g of Vaseline under aseptic conditions.

Example E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

Example F

Coated Tablets

Tablets are pressed analogously to Example E and subsequently coated in a conventional manner with a coating of sucrose, potato starch, talc, tragacanth and dye.

Example G

Capsules 2 kg of active ingredient of the formula I are introduced into hard gelatine capsules in a conventional manner in such a way that each capsule contains 20 mg of the active ingredient.

Example H

Ampoules

A solution of 1 kg of active ingredient of the formula I in 60 L of bidistilled water is sterile filtered, transferred into ampoules, lyophilised under sterile conditions and sealed under sterile conditions. Each ampoule contains 10 mg of active ingredient.

We claim:
1. A kit comprising separate packs of an effective amount of a compound of Formula I

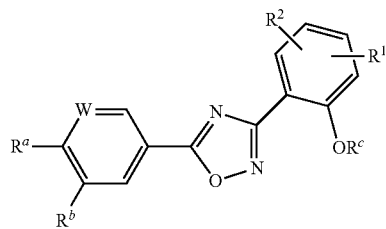

I and an effective amount of an additional active ingredient,
$R^1$, $R^2$ denote H, Hal, $CF_3$, $OCF_3$, CN, or $NO_2$,
W denotes CH or N,
$R^a$ is Ar, Het, cycloalkyl having 3-7 atoms, A or $NA_2$,
$R^b$ is H, A, Hal, $CF_3$, $OCF_3$, $OR^3$, CN, $NO_2$, $(CH_2)_nN(R^3)_2$, OA, $(CH_2)_nSO_2N(R^3)_2$, $(CH_2)_nNR^3SO_2A$, $(CH_2)_nN(SO_2A)_2$, $NR^3CON(R^3)_2$, $NR^3COA$ or $(CH_2)_nSO_2R^3$,
$R^c$ denotes A, COA, CSA, COOA, CSOA, $CON(R^3)_2$ or $CSN(R^3)_2$,
A is branched or linear alkyl having 1 to 12 C-atoms, wherein one or more, H-atoms may be replaced by Hal, or 1 to 7H-atoms may be replaced by $OR^3$, CN or $N(R^3)_2$ and wherein one or more, preferably 1 to 7 non-adjacent $CH_2$-groups may be replaced by O, $NR^3$ or S and/or by —CH=CH— or —C≡C— groups, or denotes cycloalkyl or cycloalkylalkylene having 3-7 ring C atoms,
Hal is F, Cl, Br or I,
Ar denotes a monocyclic or bicyclic, unsaturated or aromatic carbocyclic ring having 6 to 14 carbon atoms which may be unsubstituted or monosubstituted, disubstituted or trisubstituted by Hal, A, $CH_2OA$, $CH_2N(R^3)_2$, $OR^3$, $N(R^3)_2$, $NO_2$, $N(SO_2Me)_2$, CN, $COOR^3$, $CF_3$, $OCF_3$, $CON(R^3)_2$, $NR^3COA$, $NR^3CON(R^3)_2$, $NR^3SO_2A$, $COR^3$, $SO_2N(R^3)_2$, SOA or $SO_2A$, phenyl, pyridyl-$[C(R^3)_2]_n$—$COOR^3$ and/or —O$[C(R^3)_2]_n$—$CON(R^3)_2$, Het denotes a monocyclic or bicyclic, saturated, unsaturated or aromatic heterocyclic ring having 1 N and/or 1 to 3 O and/or S atoms which may be unsubstituted or monosubstituted, disubstituted or trisubstituted by Hal, A, —$[C(R^3)_2]_n$—Ar, —$[C(R^3)_2]_n$-cycloalkyl, $CH_2OA$, $CH_2N(R^3)_2$, $OR^3$, $CF_3$, $OCF_3$, $N(R^3)_2$, $N(SO_2Me)_2$, $NR^3CON(R^3)_2$, $NO_2$, CN, —$[C(R^3)_2]_n$—$COOR^3$, —$[C(R^3)_2]_n$—$CON(R^3)_2$, $NR^3COA$, $NR^3SO_2A$, $COR^3$, $SO_2N(R^3)_2$, SOA, phenyl, pyridyl and/or $SO_2A$, $R^3$ is H or A, and n is 0, 1, 2, 3, 4, 5, 6, 7 or 8, and pharmaceutically acceptable solvates, tautomers, salts and stereoisomers thereof, including mixtures thereof in all ratios.

2. The kit according to claim 1, wherein $R^a$ denotes Ar or Het.

3. The kit according to claim 1, wherein Ar denotes one of the following groups:

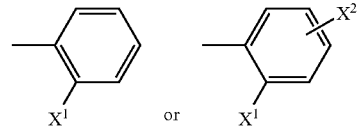

wherein $X^1$, and $X^2$ independently of one another F, $OCH_3$, $CH_3$, $CF_3$, $OCF_3$, OH, $NO_2$, CN, and/or phenyl.

4. The kit according to claim 3, wherein Het denotes one of the following groups:

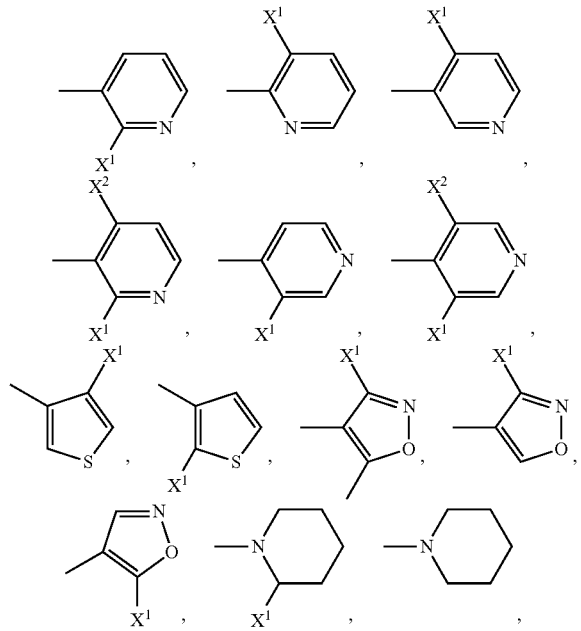

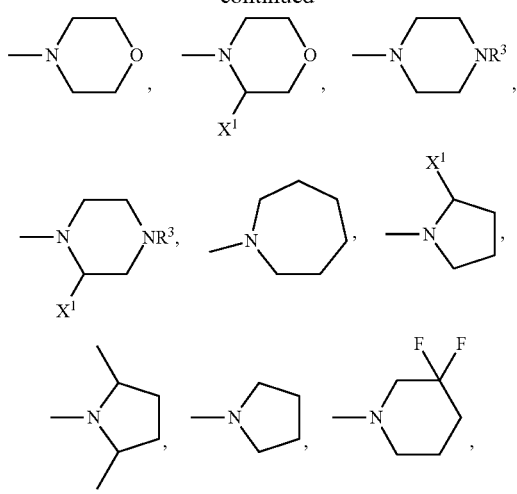
wherein $X^1$, and $X^2$ denote independently of one another F, $OCH_3$, $CH_3$, $CF_3$, $OCF_3$, OH, $NO_2$, CN, and/or phenyl and $R^3$ has the meaning given in claim 1.
5. The kit according to claim 2, wherein Ar or Het is substituted by methyl, trifluoromethyl or methoxy.
6. The kit according to claim 1, said compound being selected from:
I1
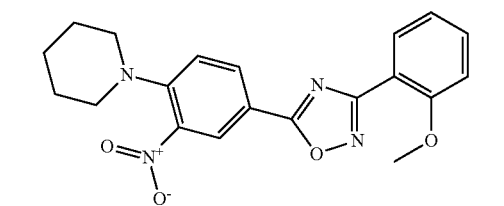
I2
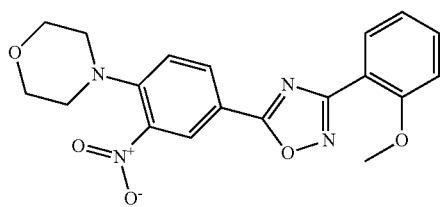
I3
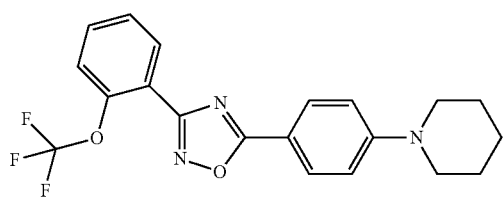
I4
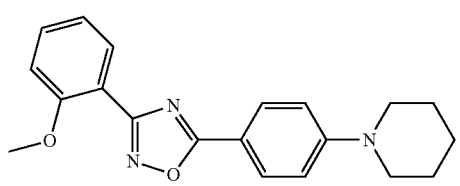
I5
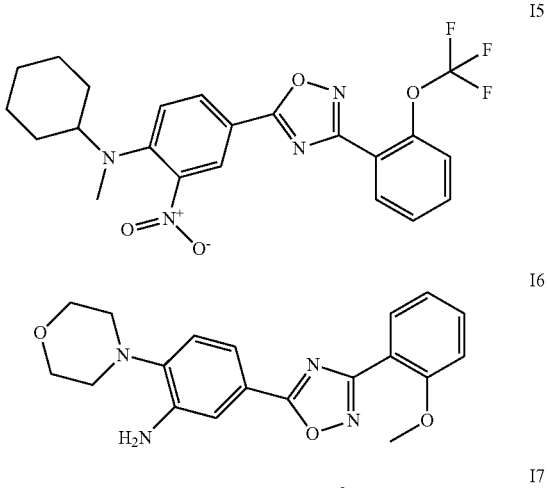
I6
I7
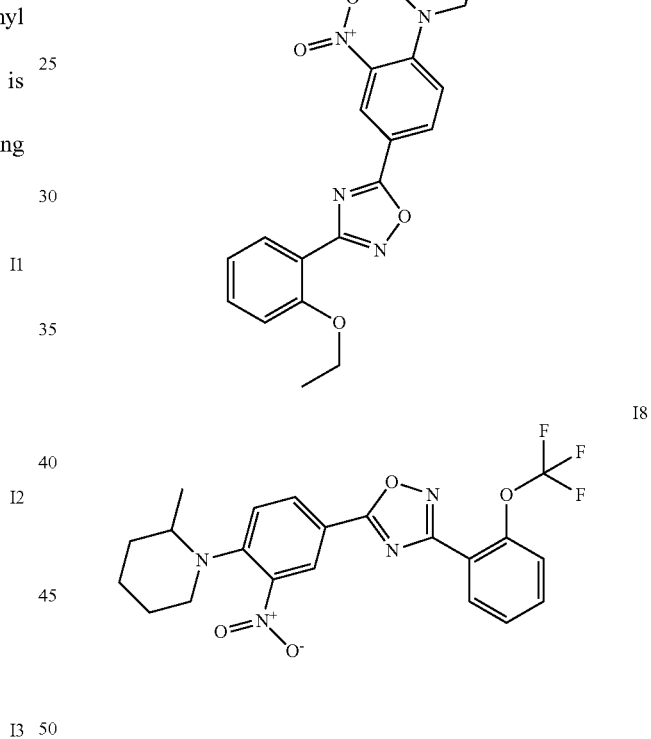
I8
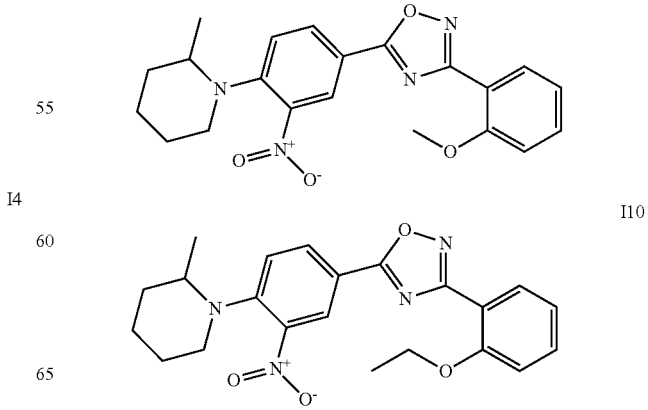
I9
I10

I11 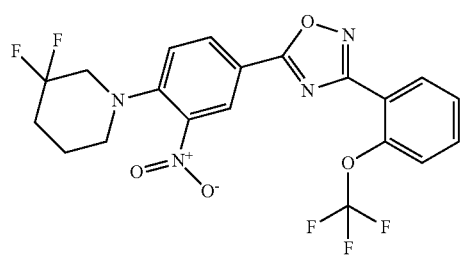
I12 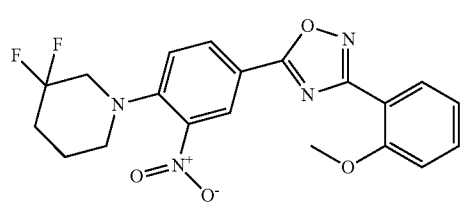
I13 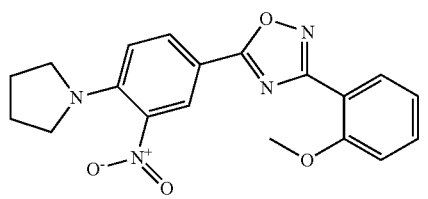 [SMILES: COc1ccccc1-c1noc(-c2ccc(N3CCCC3)c([N+](=O)[O-])c2)n1]
I14 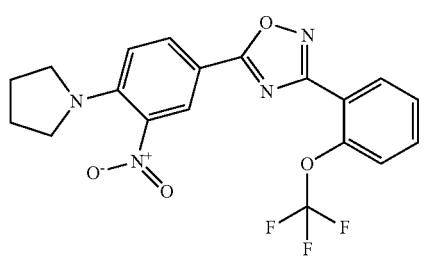 [SMILES: O=[N+]([O-])c1cc(-c2nc(-c3ccccc3OC(F)(F)F)no2)ccc1N1CCCC1]
I15 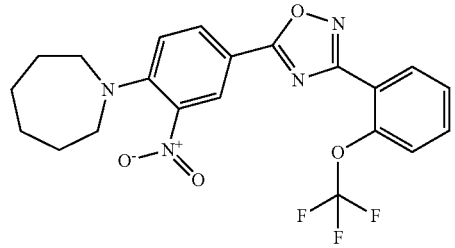
I16 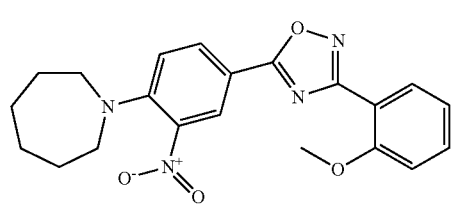
I17 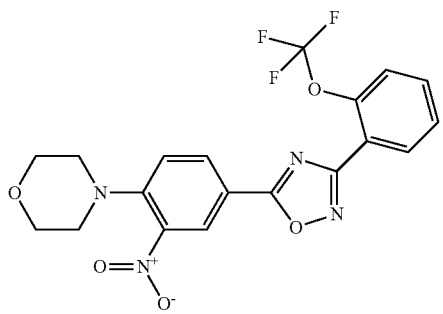 [SMILES: O=[N+]([O-])c1cc(-c2nc(-c3ccccc3OC(F)(F)F)no2)ccc1N1CCOCC1]
I18 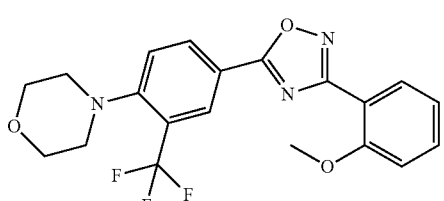
I19 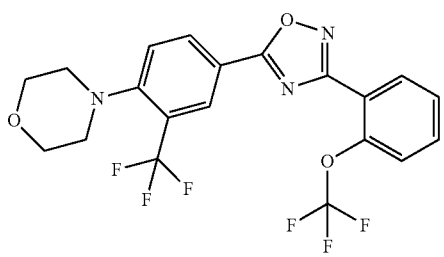 [SMILES: FC(F)(F)Oc1ccccc1-c1noc(-c2ccc(N3CCOCC3)c(C(F)(F)F)c2)n1]
I20 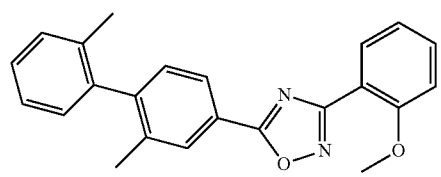 [SMILES: COc1ccccc1-c1noc(-c2ccc(-c3ccccc3C)c(C)c2)n1]
I21 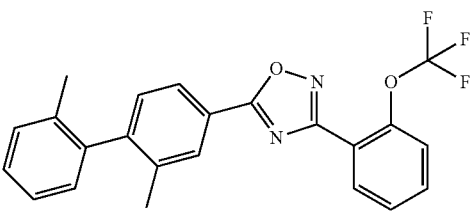 [SMILES: Cc1ccccc1-c1ccc(-c2nc(-c3ccccc3OC(F)(F)F)no2)cc1C]
I22 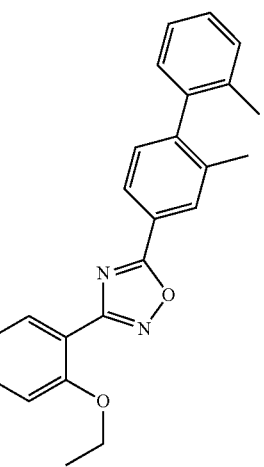

| | |
|---|---|
| 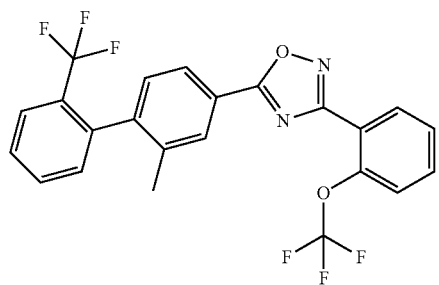 [SMILES: Cc1cc(-c2nc(-c3ccccc3OC(F)(F)F)no2)ccc1-c1ccccc1C(F)(F)F] | I23 |
| 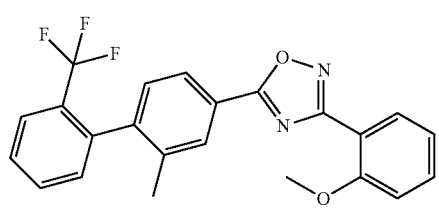 [SMILES: COc1ccccc1-c1noc(-c2ccc(-c3ccccc3C(F)(F)F)c(C)c2)n1] | I24 |
| 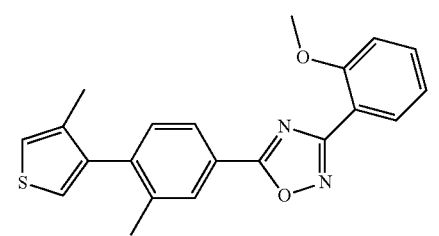 [SMILES: COc1ccccc1-c1noc(-c2ccc(-c3cscc3C)c(C)c2)n1] | I25 |
| 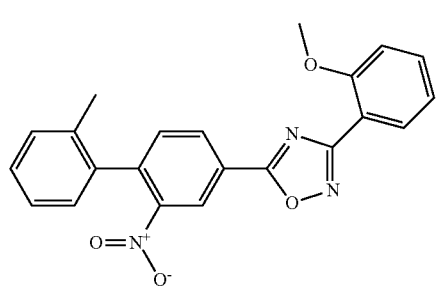 [SMILES: COc1ccccc1-c1noc(-c2ccc(-c3ccccc3C)c([N+](=O)[O-])c2)n1] | I26 |
| 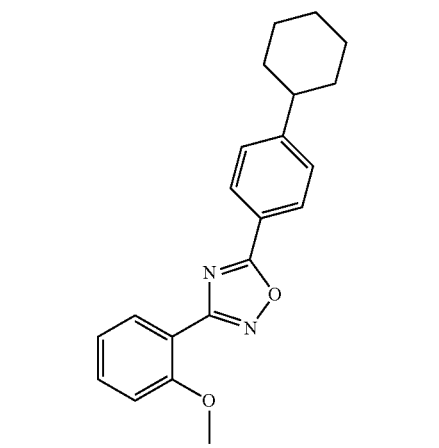 [SMILES: COc1ccccc1-c1noc(-c2ccc(C3CCCCC3)cc2)n1] | I27 |
| 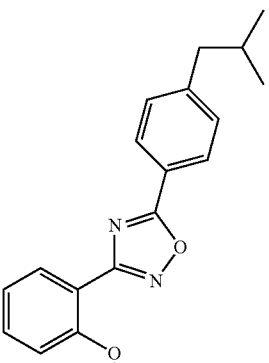 | I28 |
| 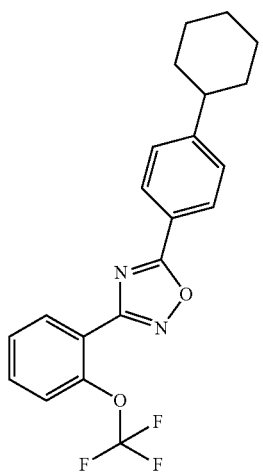 [SMILES: FC(F)(F)Oc1ccccc1-c1noc(-c2ccc(C3CCCCC3)cc2)n1] | I29 |
| 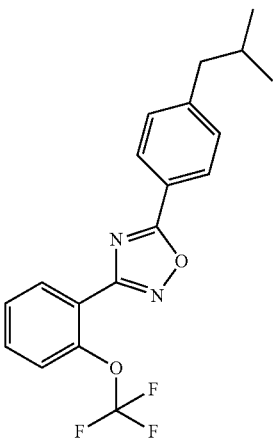 [SMILES: CC(C)Cc1ccc(-c2nc(-c3ccccc3OC(F)(F)F)no2)cc1] | I30 |
| 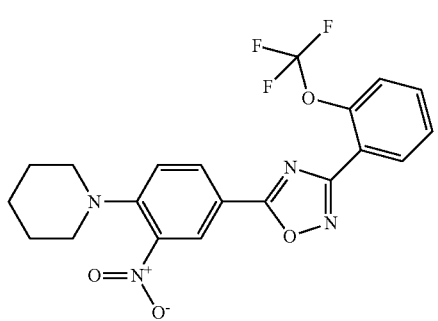 [SMILES: O=[N+]([O-])c1cc(-c2nc(-c3ccccc3OC(F)(F)F)no2)ccc1N1CCCCC1] | I31 |

-continued
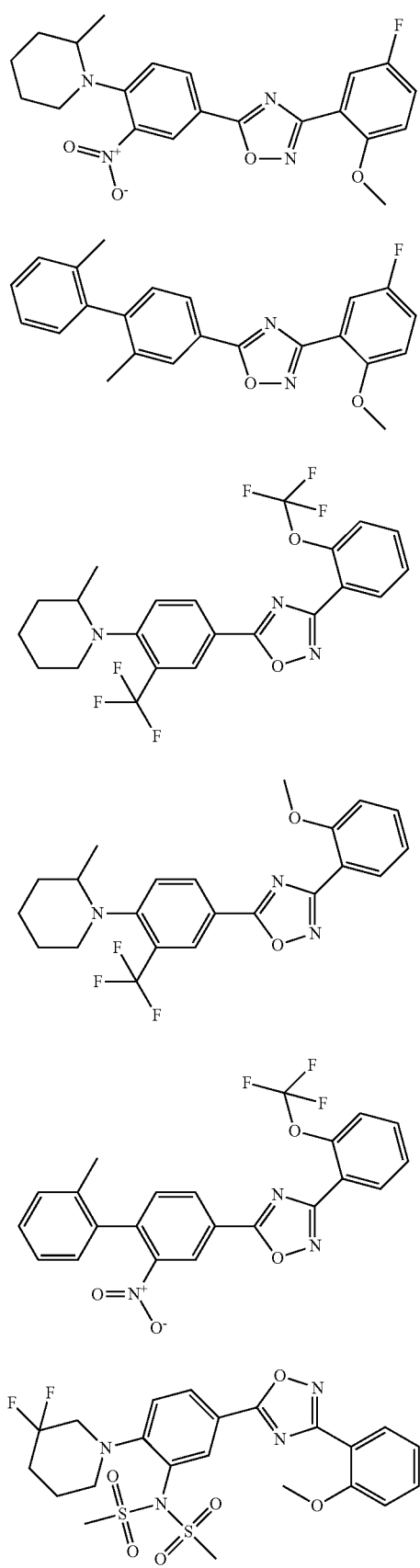
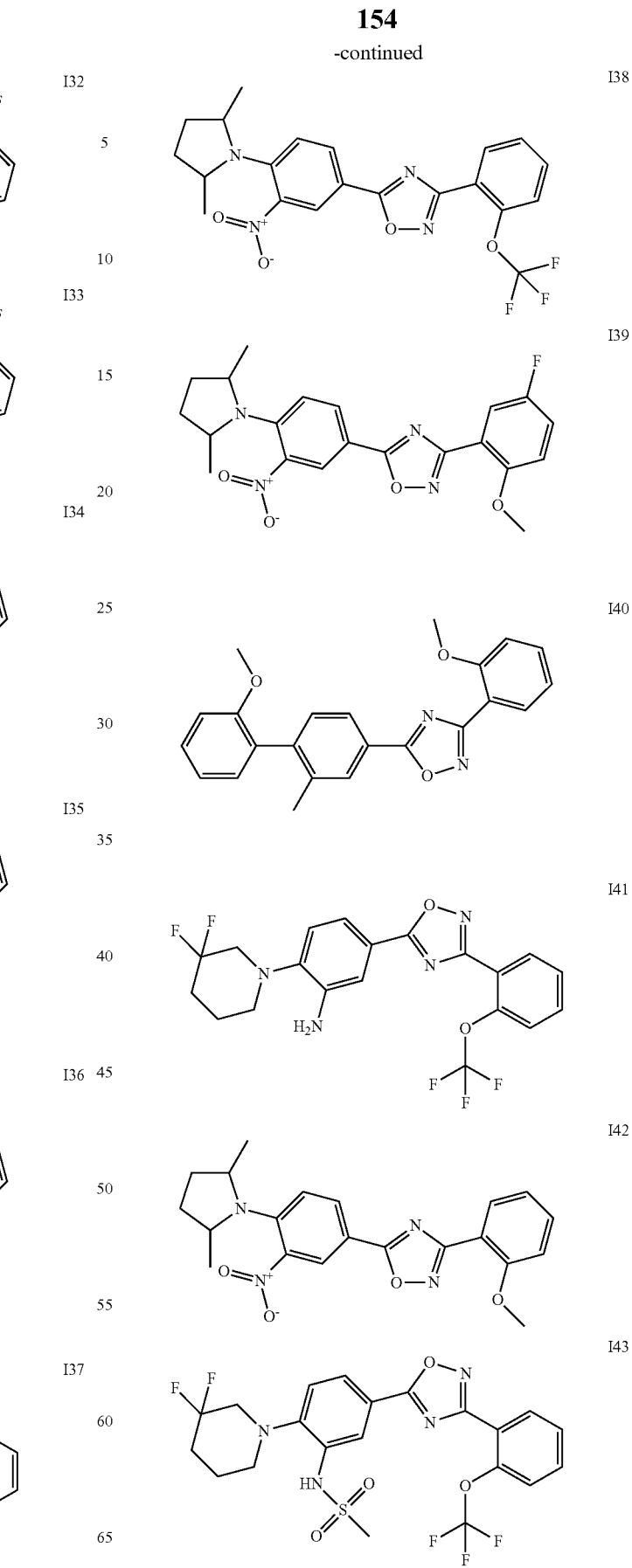

I44 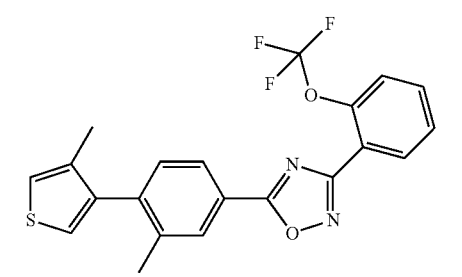 [SMILES: Cc1cc(-c2nc(-c3ccccc3OC(F)(F)F)no2)ccc1-c1cscc1C]
I45 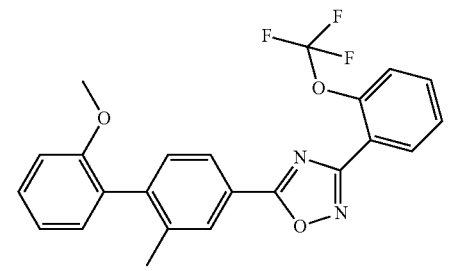 [SMILES: COc1ccccc1-c1ccc(-c2nc(-c3ccccc3OC(F)(F)F)no2)cc1C]
I46 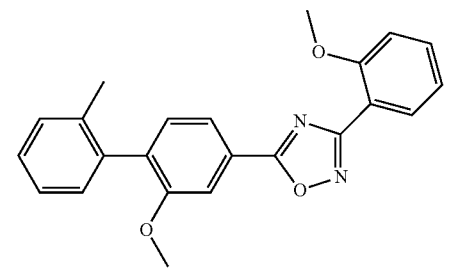 [SMILES: COc1ccccc1-c1noc(-c2ccc(-c3ccccc3C)c(OC)c2)n1]
I47 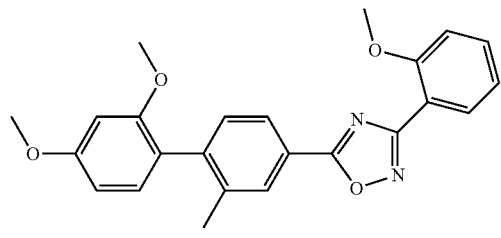 [SMILES: COc1ccc(-c2ccc(-c3nc(-c4ccccc4OC)no3)cc2C)c(OC)c1]
I48 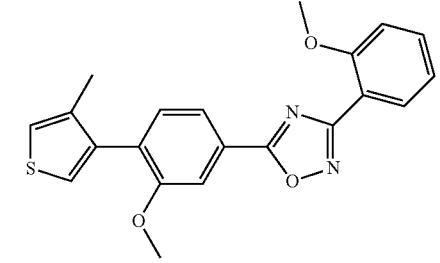 [SMILES: COc1ccccc1-c1noc(-c2ccc(-c3cscc3C)c(OC)c2)n1]
I49 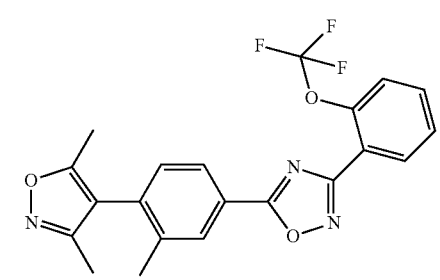 [SMILES: Cc1cc(-c2nc(-c3ccccc3OC(F)(F)F)no2)ccc1-c1c(C)noc1C]
I50 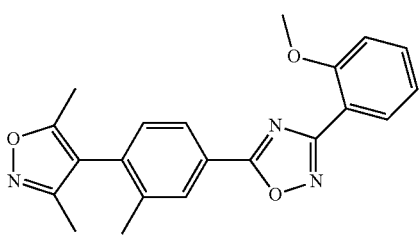 [SMILES: COc1ccccc1-c1noc(-c2ccc(-c3c(C)noc3C)c(C)c2)n1]
I51 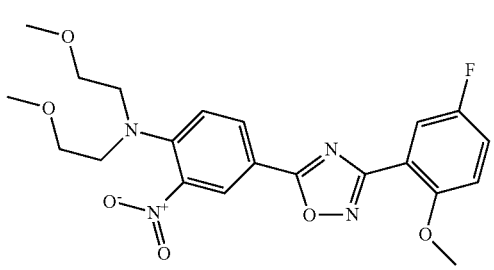 [SMILES: COCCN(CCOC)c1ccc(-c2nc(-c3cc(F)ccc3OC)no2)cc1[N+](=O)[O-]]
I52 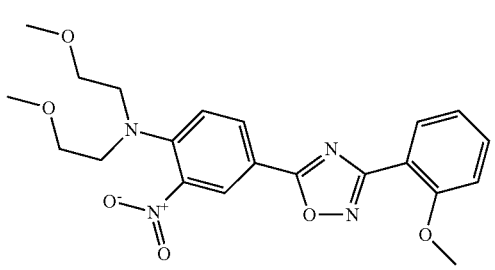 [SMILES: COCCN(CCOC)c1ccc(-c2nc(-c3ccccc3OC)no2)cc1[N+](=O)[O-]]
I53 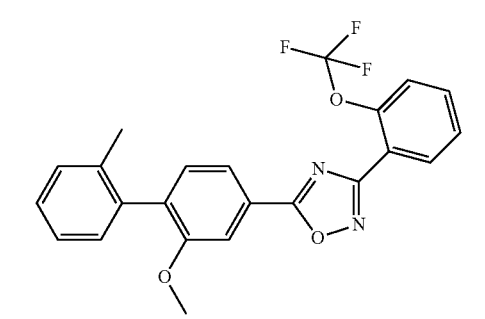 [SMILES: COc1cc(-c2nc(-c3ccccc3OC(F)(F)F)no2)ccc1-c1ccccc1C]
I54 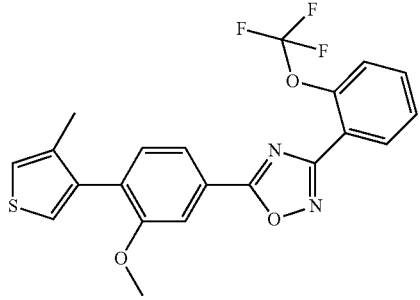 [SMILES: COc1cc(-c2nc(-c3ccccc3OC(F)(F)F)no2)ccc1-c1cscc1C]

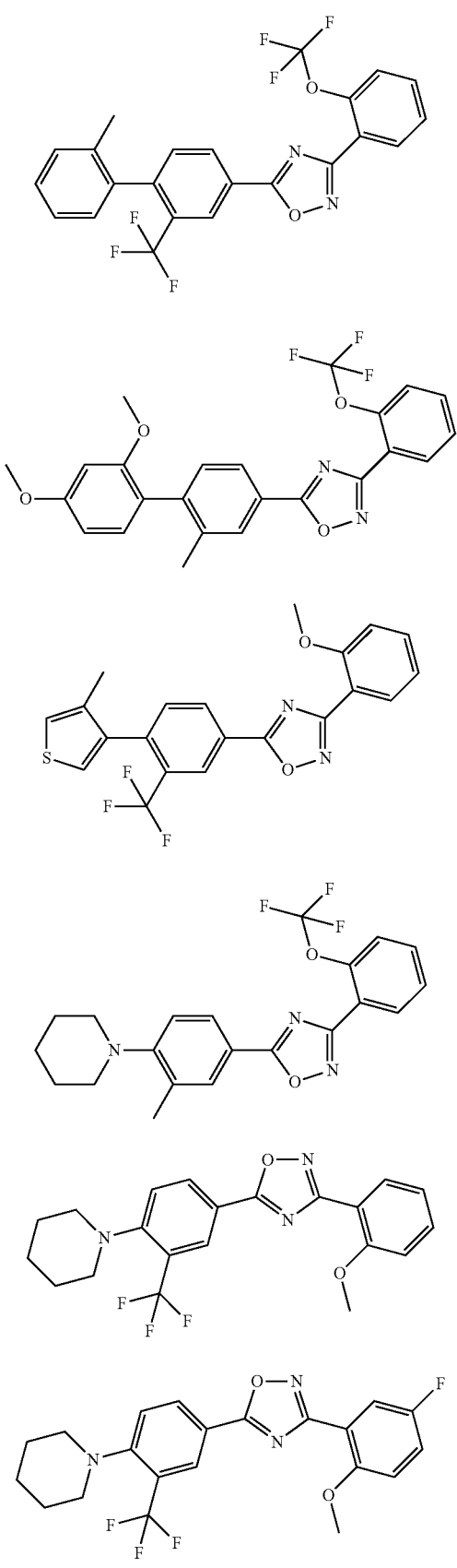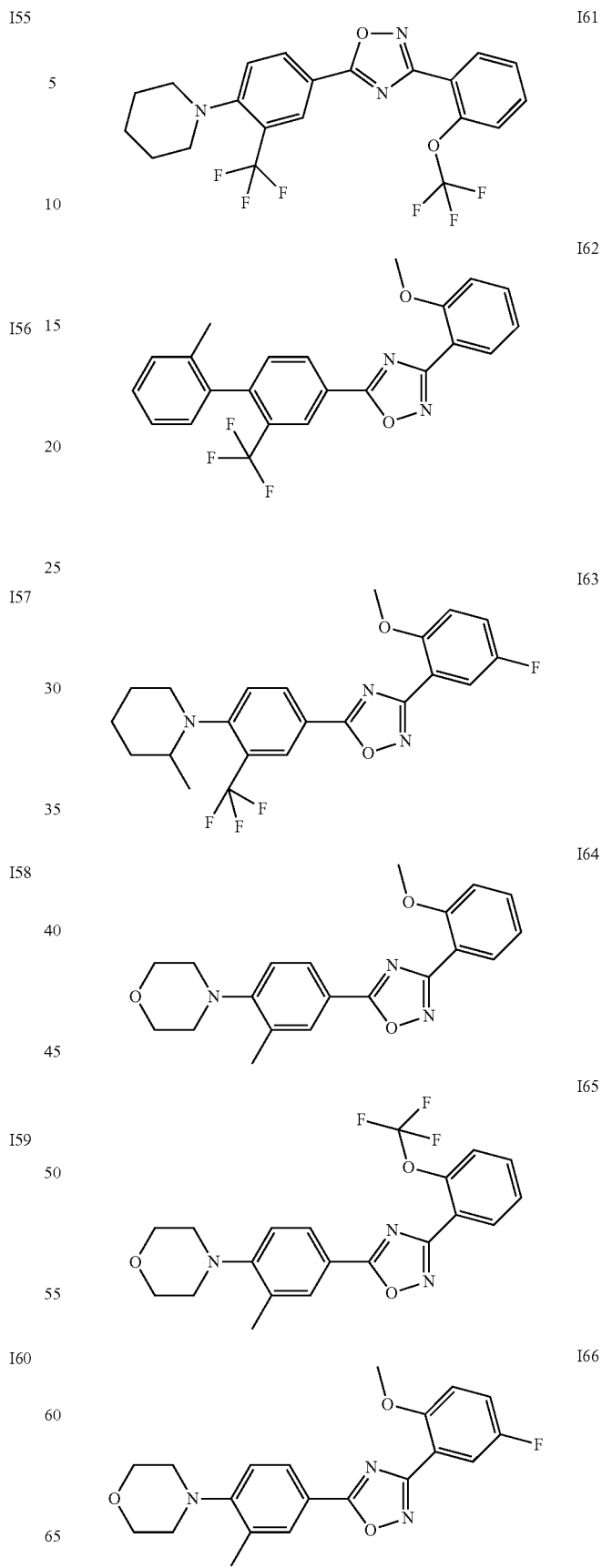

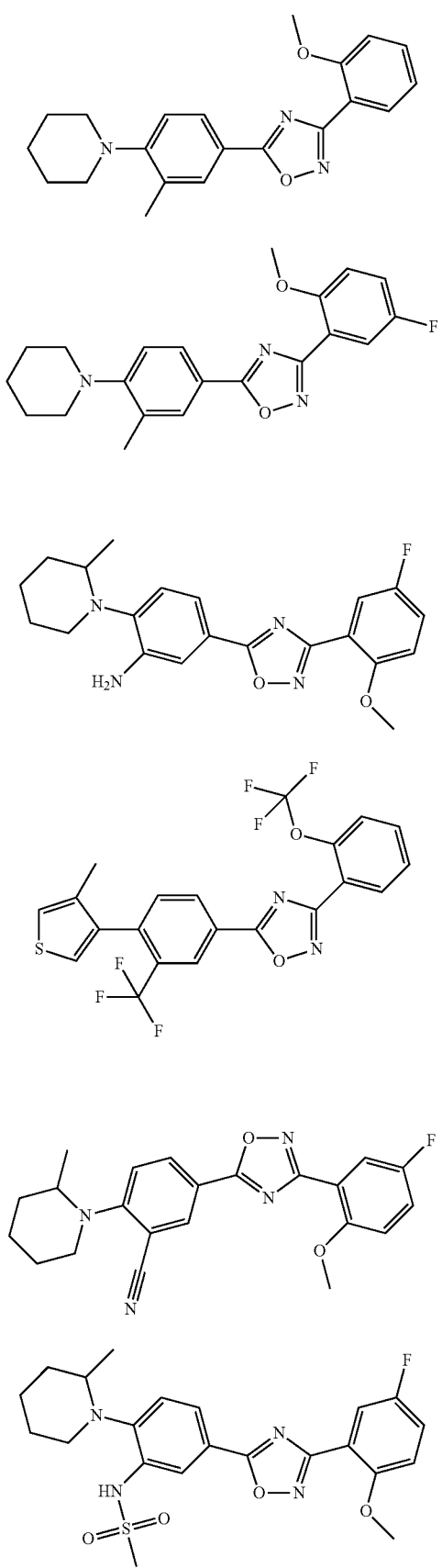
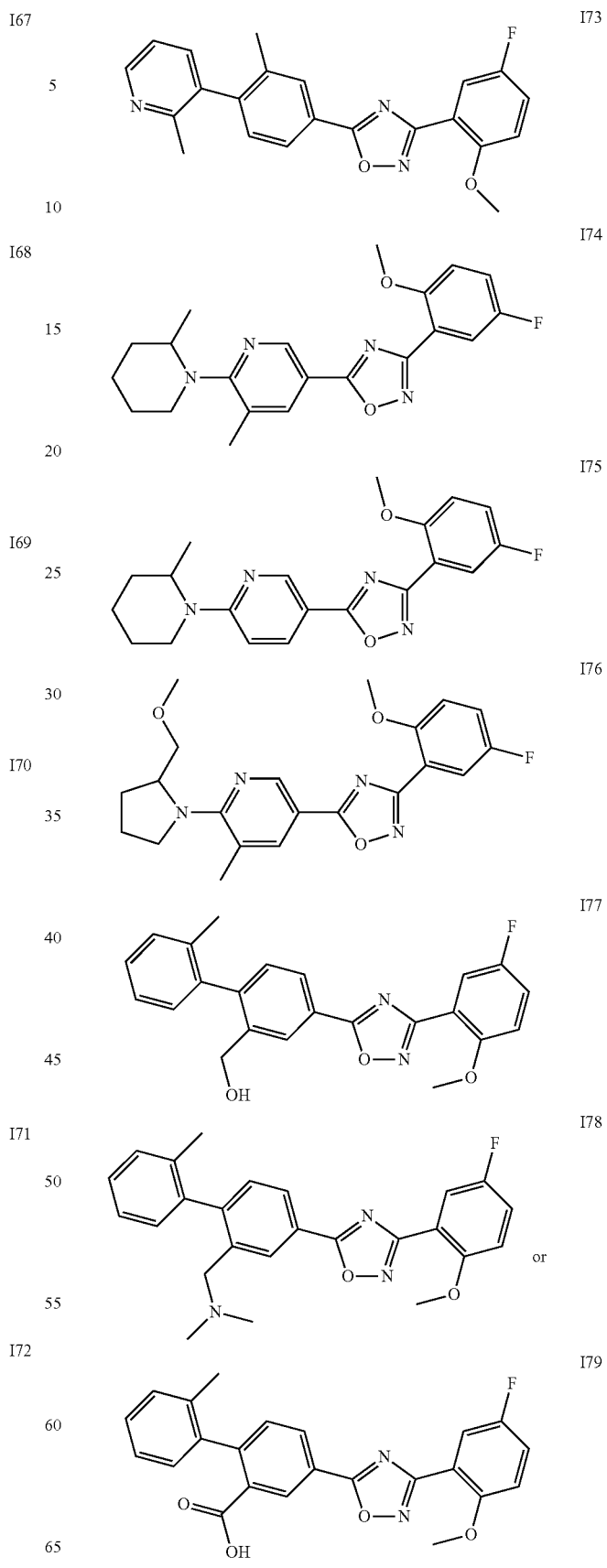

and pharmaceutically acceptable solvates, tautomers, salts and stereoisomers thereof, including mixtures thereof in all ratios.

7. A method for the treatment of multiple sclerosis comprising the administration of a compound of Formula I,

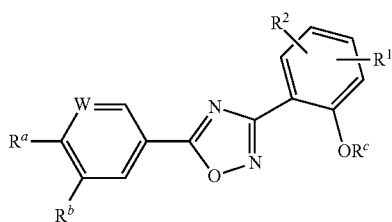

I or a composition thereof, to an individual having multiple sclerosis, wherein:

$R^1$, $R^2$ denote H, Hal, $CF_3$, $OCF_3$, CN, or $NO_2$

W denotes CH or N, $R^a$ is Ar, Het, cycloalkyl having 3-7 atoms, A or $NA_2$, $R^b$ is H, A, Hal, $CF_3$, $OCF_3$, $OR^3$, CN, $NO_2$, $(CH_2)_2N(R^3)_2$, OA, $(CH_2)_nSO_2N(R^3)_2$, $(CH_2)_nNR^3SO_2A$, $(CH_2)_nN(SO_2A)_2$, $NR^3CON(R^3)_2$, $NR^3COA$ or $(CH_2)_nSO_2R^3$, $R^c$ denotes A, COA, CSA, COOA, CSOA, $CON(R^3)_2$ or $CSN(R^3)_2$, A is branched or linear alkyl having 1 to 12 C-atoms, wherein one or more, H-atoms may be replaced by Hal, or 1 to 7H-atoms may be replaced by $OR^3$, CN or $N(R^3)_2$ and wherein one or more, preferably 1 to 7 non-adjacent $CH_2$-groups may be replaced by O, $NR^3$ or S and/or by —CH=CH— or —C≡O— groups, or denotes cycloalkyl or cycloalkylalkylene having 3-7 ring C atoms, Hal is F, Cl, Br or I, Ar denotes a monocyclic or bicyclic, unsaturated or aromatic carbocyclic ring having 6 to 14 carbon atoms which may be unsubstituted or monosubstituted, disubstituted or trisubstituted by Hal, A, $CH_2OA$, $CH_2N(R^3)_2$, $OR^3$, $N(R^3)_2$, $NO_2$, $N(SO_2Me)_2$, CN, $COOR^3$, $CF_3$, $OCF_3$, $CON(R^3)_2$, $NR^3COA$, $NR^3CON(R^3)_2$, $NR^3SO_2A$, $COR^3$, $SO_2N(R^3)_2$, SOA or $SO_2A$, phenyl, pyridyl-$[C(R^3)_2]_n$—$COOR^3$ and/or —$O[C(R^3)_2]_n$—$CON(R^3)_2$, Het denotes a monocyclic or bicyclic, saturated, unsaturated or aromatic heterocyclic ring having 1 N and/or 1 to 3 O and/or S atoms which may be unsubstituted or monosubstituted, disubstituted or trisubstituted by Hal, A, —$[C(R^3)_2]_n$—Ar, —$[C(R^3)_2]_n$-cycloalkyl, $CH_2OA$, $CH_2N(R^3)_2$, $OR^3$, $CF_3$, $OCF_3$, $N(R^3)_2$, $N(SO_2Me)_2$, $NR^3CON(R^3)_2$, $NO_2$, CN, —$[C(R^3)_2]_n$—$COOR^3$, —$[C(R^3)_2]_n$—$CON(R^3)_2$, $NR^3COA$, $NR^3SO_2A$, $COR^3$, $SO_2N(R^3)_2$, SOA, phenyl, pyridyl and/or $SO_2A$, $R^3$ is H or A, and n is 0, 1, 2, 3, 4, 5, 6, 7 or 8, and pharmaceutically acceptable solvates, tautomers, salts and stereoisomers thereof, including mixtures thereof in all ratios.

8. The method according to claim 7, wherein $R^a$ denotes Ar or Het.

9. The method according to claim 7, wherein Ar denotes one of the following groups:

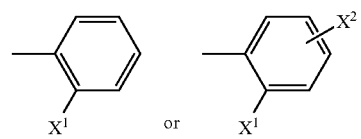

wherein $X^1$, and $X^2$ independently of one another F, $OCH_3$, $CH_3$, $CF_3$, $OCF_3$, OH, $NO_2$, CN, and/or phenyl.

10. The method according to claim 8, wherein Het denotes one of the following groups:

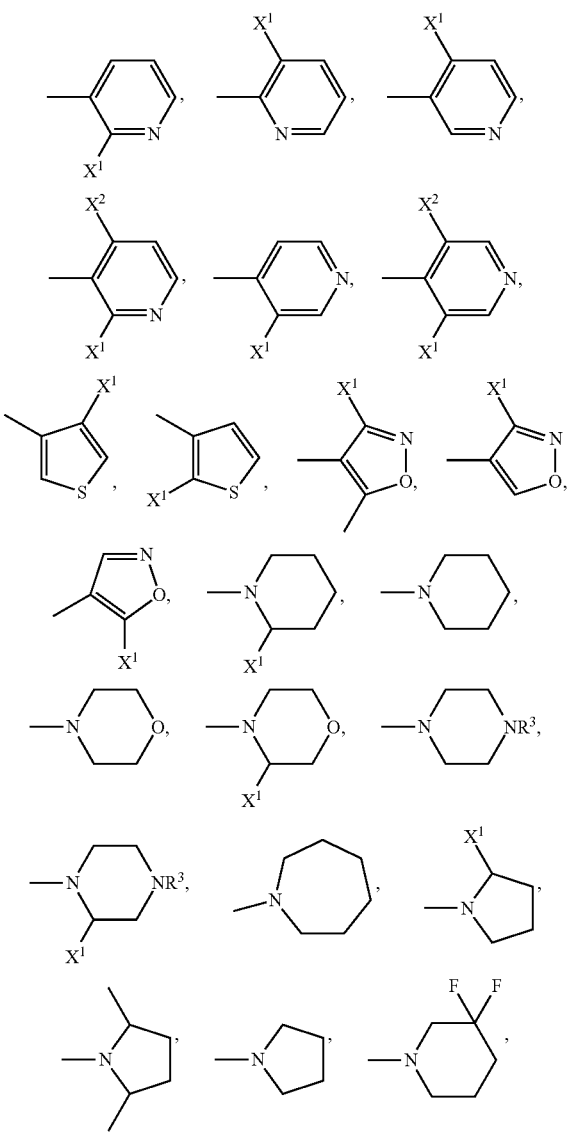

wherein $X^1$, and $X^2$ denote independently of one another F, $OCH_3$, $CH_3$, $CF_3$, $OCF_3$, OH, $NO_2$, CN, and/or phenyl and $R^3$ has the meaning given in claim 1.

11. The method according to claim 8, wherein Ar or Het is substituted by methyl, trifluoromethyl or methoxy.

12. The method according to claim 7, said compound being selected from:

I1
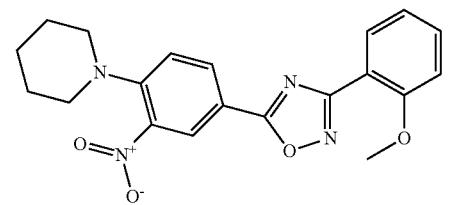
I2
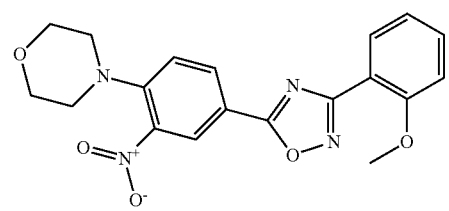
I3
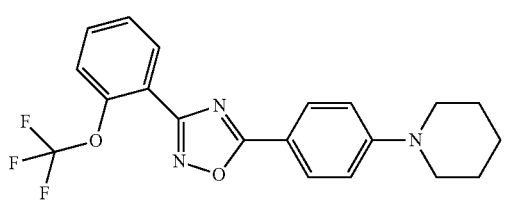
I4
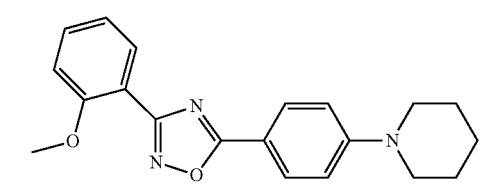
I5
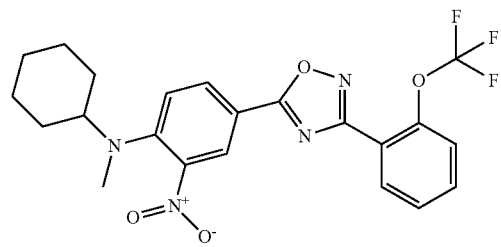
I6
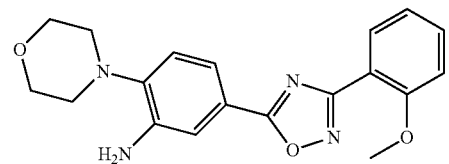
-continued
I7
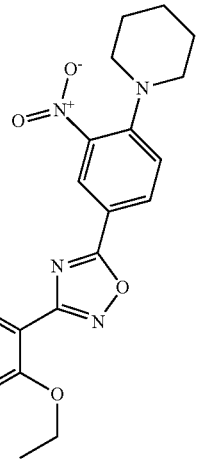
I8
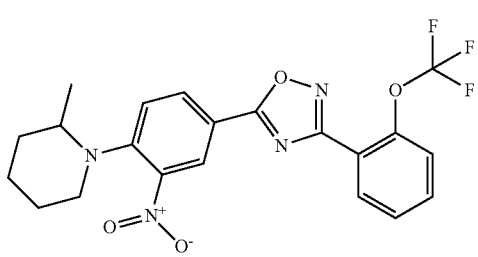
I9
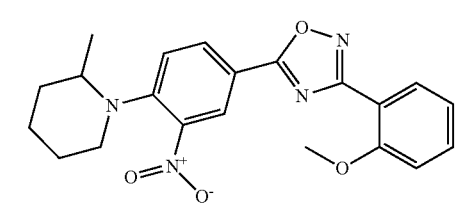
I10
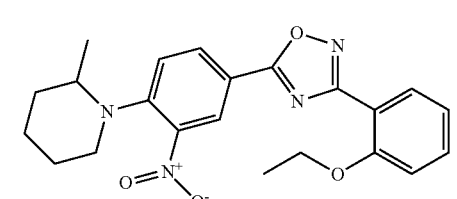
I11
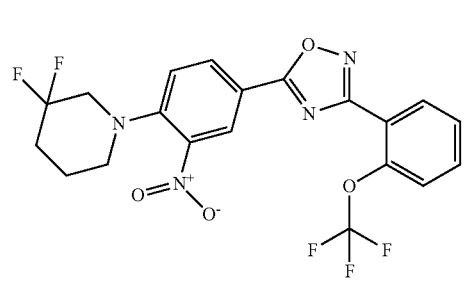
I12
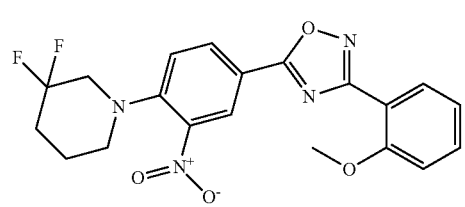

I13 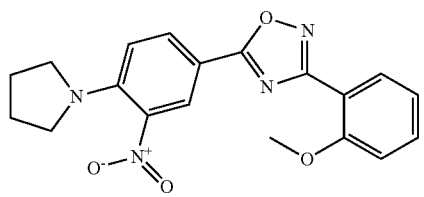
I14 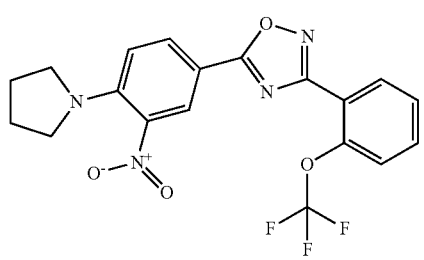
I15 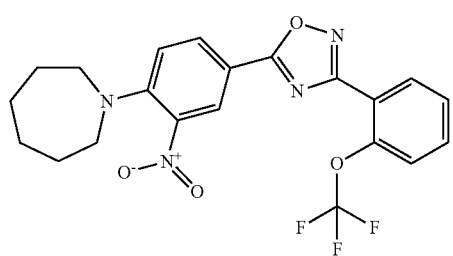
I16 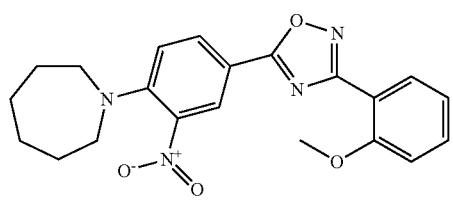
I17 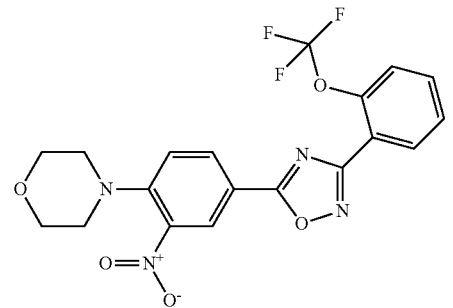
I18 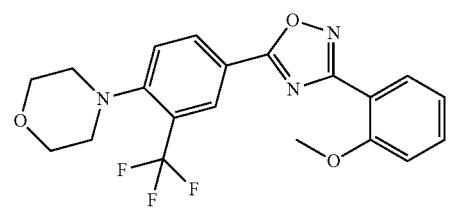
I19 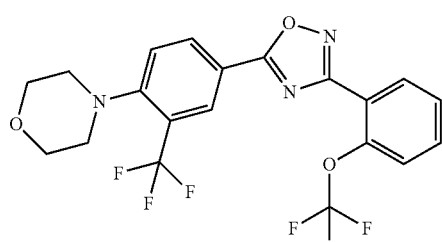
I20 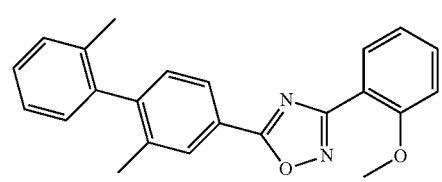
I21 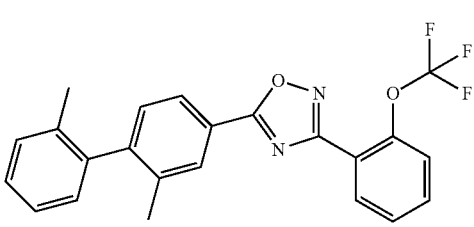
I22 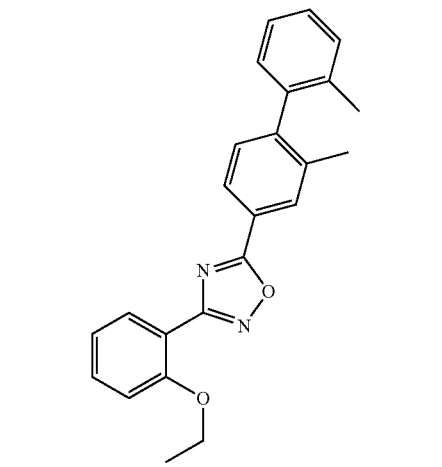
I23 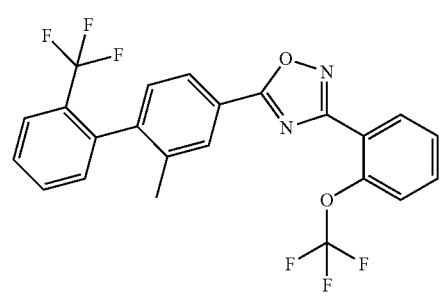
I24 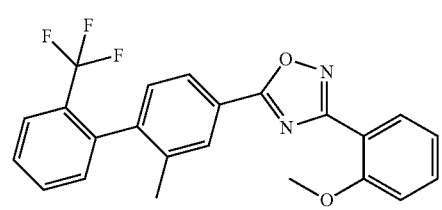

I25 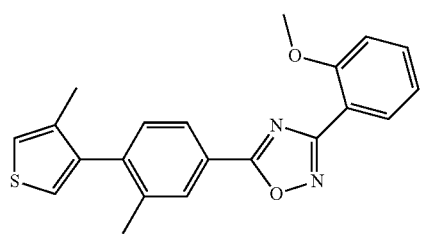
I26 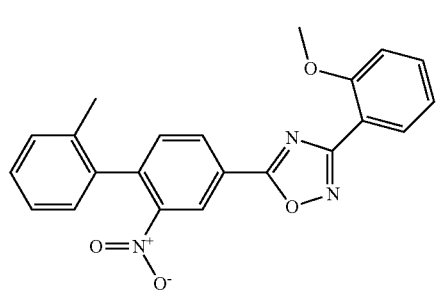
I27 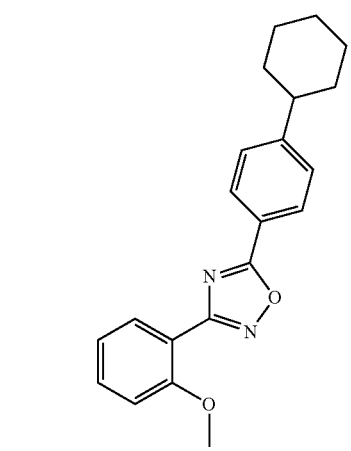
I28 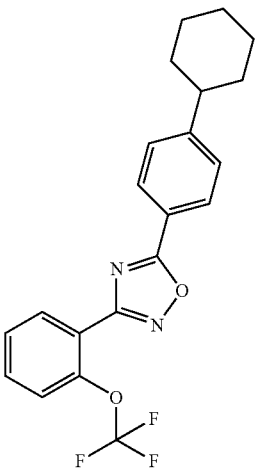
I29 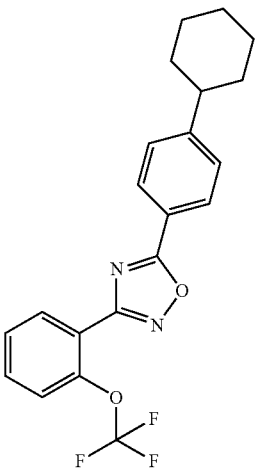
I30 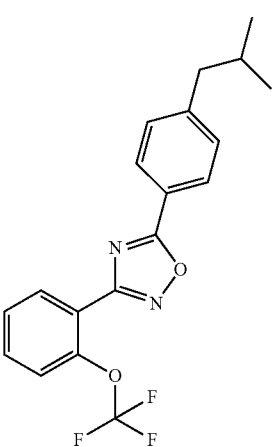
I31 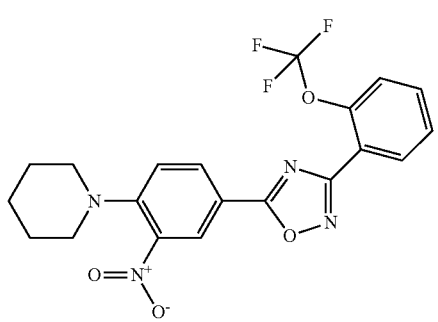
I32 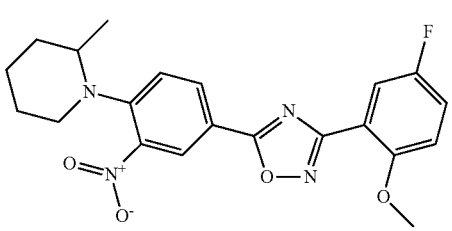

169
-continued

170
-continued

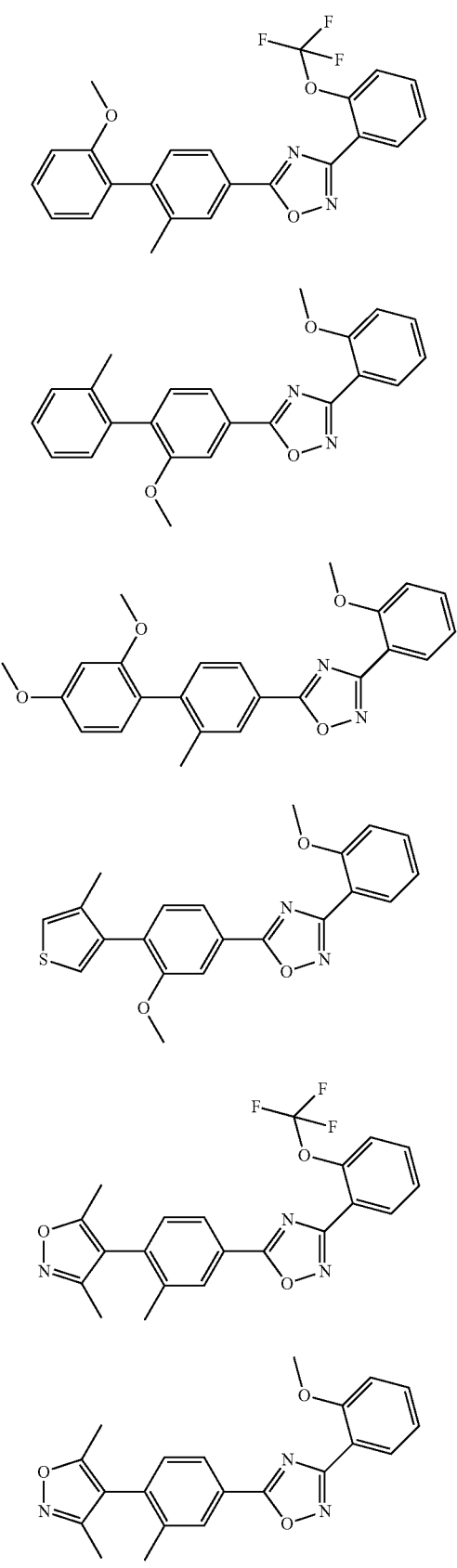
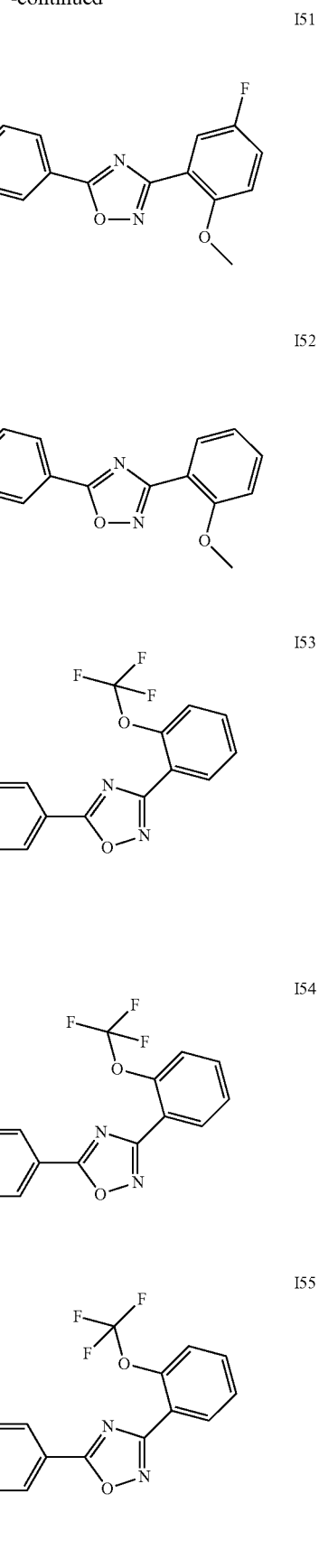

US 8,889,668 B2
173
-continued
174
-continued
I56
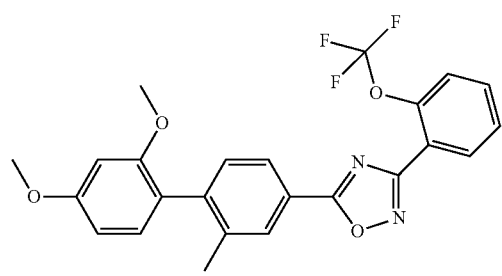 [SMILES: COc1ccc(-c2ccc(-c3nc(-c4ccccc4OC(F)(F)F)no3)cc2C)c(OC)c1]
I57
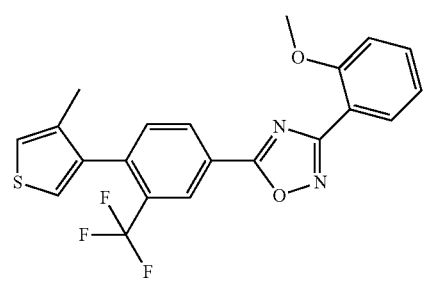 [SMILES: COc1ccccc1-c1noc(-c2ccc(-c3cscc3C)c(C(F)(F)F)c2)n1]
I58
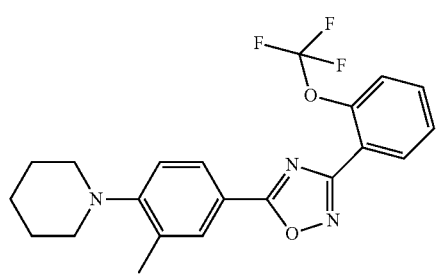 [SMILES: Cc1cc(-c2nc(-c3ccccc3OC(F)(F)F)no2)ccc1N1CCCCC1]
I59
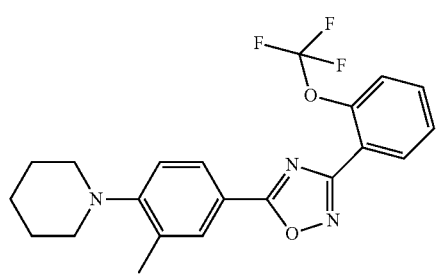 [SMILES: Cc1cc(-c2nc(-c3ccccc3OC(F)(F)F)no2)ccc1N1CCCCC1]
I60
I61
I62
I63
I64
I65
I66
I67

-continued
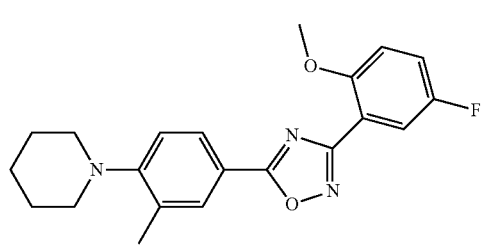 [SMILES: COc1ccc(F)cc1-c1noc(-c2ccc(N3CCCCC3)c(C)c2)n1]
I68
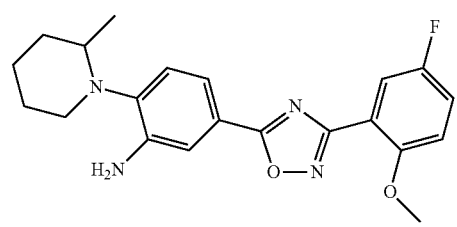 [SMILES: COc1ccc(F)cc1-c1noc(-c2ccc(N3CCCCC3C)c(N)c2)n1]
I69
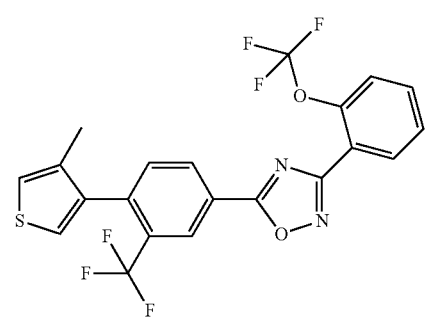 [SMILES: Cc1cscc1-c1ccc(-c2nc(-c3ccccc3OC(F)(F)F)no2)cc1C(F)(F)F]
I70
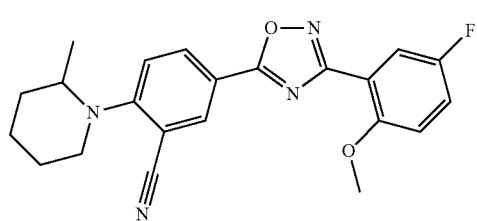 [SMILES: COc1ccc(F)cc1-c1noc(-c2ccc(N3CCCCC3C)c(C#N)c2)n1]
I71
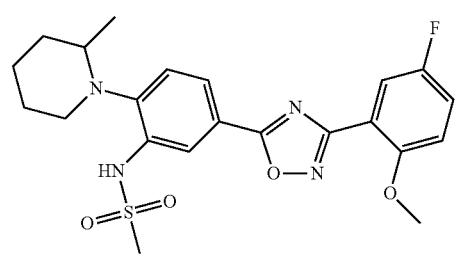 [SMILES: COc1ccc(F)cc1-c1noc(-c2ccc(N3CCCCC3C)c(NS(C)(=O)=O)c2)n1]
I72
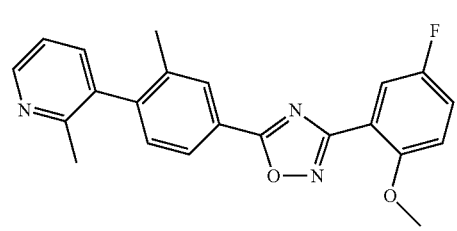
I73
-continued
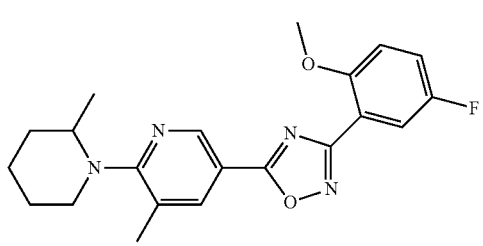 [SMILES: COc1ccc(F)cc1-c1noc(-c2cnc(N3CCCCC3C)c(C)c2)n1]
I74
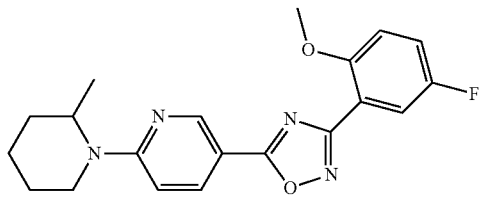 [SMILES: COc1ccc(F)cc1-c1noc(-c2ccc(N3CCCCC3C)nc2)n1]
I75
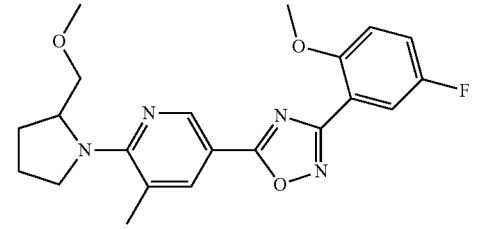
I76
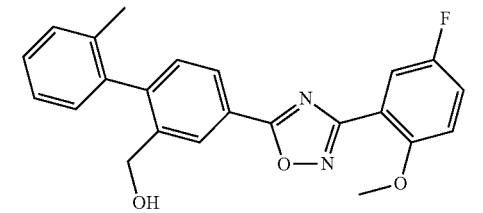 [SMILES: COc1ccc(F)cc1-c1noc(-c2ccc(-c3ccccc3C)c(CO)c2)n1]
I77
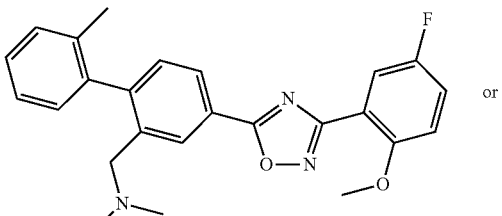
I78 or
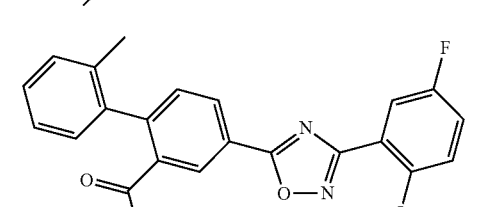
I79
and pharmaceutically acceptable solvates, tautomers, salts and stereoisomers thereof, including mixtures thereof in all ratios.
* * * * *

UNITED STATES PATENT AND TRADEMARK OFFICE
CERTIFICATE OF CORRECTION

PATENT NO. : 8,889,668 B2
APPLICATION NO. : 13/711934
DATED : November 18, 2014
INVENTOR(S) : Cyril Montagne et al.

It is certified that error appears in the above-identified patent and that said Letters Patent is hereby corrected as shown below:

In the Specification

Column 6,
Line 56, "Formula (II)" should read --Formula (Ii)--.

Column 17,
Line 46, "–O[C(R$^3$)$_2$]$_n$CON(R$^3$)$_2$." should read -- –O[C(R$^3$)$_2$]$_n$–CON(R$^3$)$_2$.--.

Column 28,
Lines 8-12,

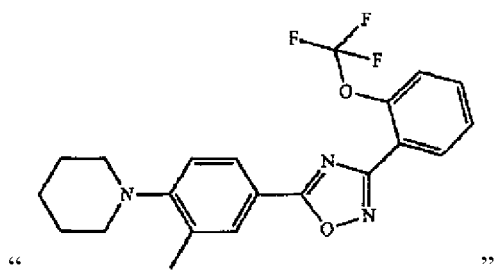

" "

should read

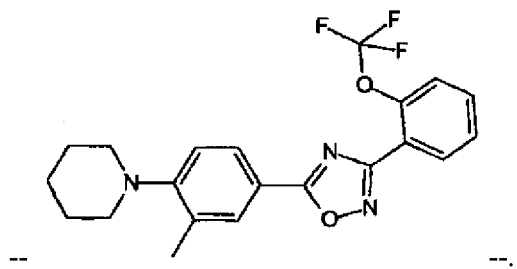

-- --.

Column 72,
Line 33, "chromatography c-hexane/ethyl" should read --chromatography (c-hexane/ethyl--.

Signed and Sealed this
Twenty-eighth Day of July, 2015

Michelle K. Lee
*Director of the United States Patent and Trademark Office*

Column 73,
Line 31, "chromatography c-hexane/ethyl" should read --chromatography (c-hexane/ethyl--.

Column 75,
Line 30, "chromatography c-hexane/ethyl" should read --chromatography (c-hexane/ethyl--.

Column 80,
Line 32, "chromatography c-hexane/ethyl" should read --chromatography (c-hexane/ethyl--.

Column 84,
Line 27, "(131.13 μA;" should read --(131.13 μl;--.
Line 29, "(267.05 μA;" should read --(267.05 μl;--.
Line 31, "chromatography c-hexane/ethyl" should read --chromatography (c-hexane/ethyl--.

Column 88,
Line 30, "chromatography c-hexane/ethyl" should read --chromatography (c-hexane/ethyl--.
Line 65, "chromatography c-hexane/ethyl" should read --chromatography (c-hexane/ethyl--.

Column 89,
Line 31, "chromatography c-hexane/ethyl" should read --chromatography (c-hexane/ethyl--.
Line 66, "chromatography c-hexane/ethyl" should read --chromatography (c-hexane/ethyl--.

Column 92,
Line 30, "chromatography c-hexane/ethyl" should read --chromatography (c-hexane/ethyl--.

Column 94,
Line 32, "chromatography c-hexane/ethyl" should read --chromatography (c-hexane/ethyl--.
Line 66, "chromatography c-hexane/ethyl" should read --chromatography (c-hexane/ethyl--.

Column 96,
Line 66, "chromatography c-hexane/ethyl" should read --chromatography (c-hexane/ethyl--.

Column 97,
Line 31, "chromatography c-hexane/ethyl" should read --chromatography (c-hexane/ethyl--.
Line 65, "chromatography c-hexane/ethyl" should read --chromatography (c-hexane/ethyl--.

Column 98,
Line 32, "chromatography c-hexane/ethyl" should read --chromatography (c-hexane/ethyl--.
Line 66, "chromatography c-hexane/ethyl" should read --chromatography (c-hexane/ethyl--.

Column 99,
Line 32, "chromatography c-hexane/ethyl" should read --chromatography (c-hexane/ethyl--.
Line 66, "chromatography c-hexane/ethyl" should read --chromatography (c-hexane/ethyl--.

Column 100,
Line 31, "chromatography c-hexane/ethyl" should read --chromatography (c-hexane/ethyl--.
Line 65, "chromatography c-hexane/ethyl" should read --chromatography (c-hexane/ethyl--.

Column 101,
Line 32, "chromatography c-hexane/ethyl" should read --chromatography (c-hexane/ethyl--.

Column 103,
Line 31, "chromatography c-hexane/ethyl" should read --chromatography (c-hexane/ethyl--.

Column 104,
Line 31, "chromatography c-hexane/ethyl" should read --chromatography (c-hexane/ethyl--.
Line 66, "chromatography c-hexane/ethyl" should read --chromatography (c-hexane/ethyl--.

Column 106,
Line 57, "chromatography c-hexane/ethyl" should read --chromatography (c-hexane/ethyl--.

Column 107,
Line 66, "chromatography c-hexane/ethyl" should read --chromatography (c-hexane/ethyl--.

Column 108,
Lines 33-34, "chromatography c-hexane/ethyl" should read --chromatography (c-hexane/ethyl--.
Line 66, "chromatography c-hexane/ethyl" should read --chromatography (c-hexane/ethyl--.

Column 109,
Line 32, "chromatography c-hexane/ethyl" should read --chromatography (c-hexane/ethyl--.
Line 66, "chromatography c-hexane/ethyl" should read --chromatography (c-hexane/ethyl--.

Column 110,
Line 26, "chromatography c-hexane/ethyl" should read --chromatography (c-hexane/ethyl--.

Column 113,
Line 1, "355-GTPγS" should read --35S-GTPγS--.

Column 125,
Compound 132,

"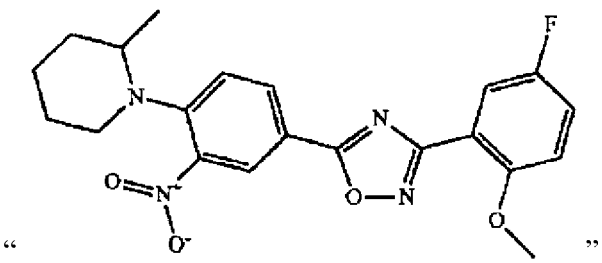"

should read

CERTIFICATE OF CORRECTION (continued)
U.S. Pat. No. 8,889,668 B2

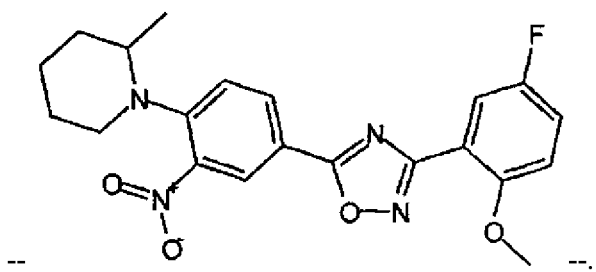

Column 125,
Compound I33,

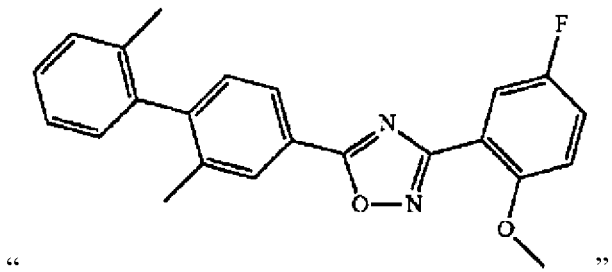

"

should read

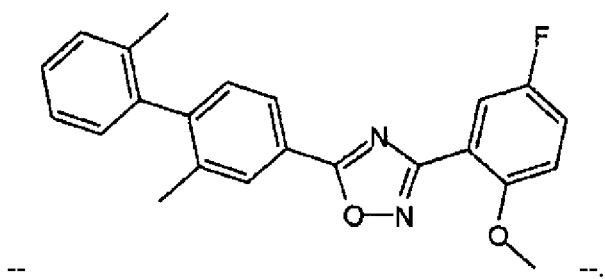

--.

Column 135,
Compound I58,

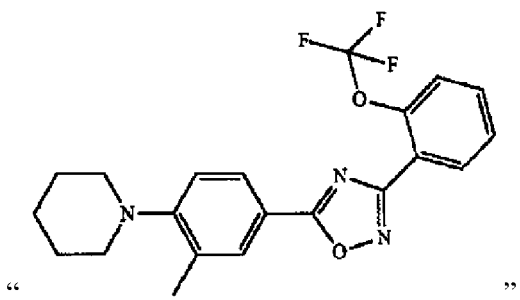

"                              "

should read

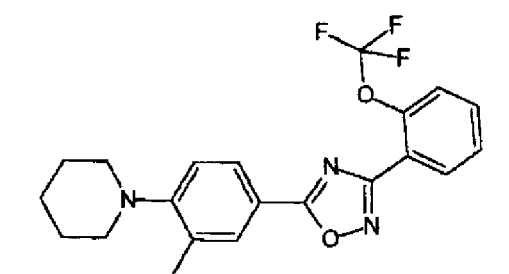

--                              --.

CERTIFICATE OF CORRECTION (continued)
U.S. Pat. No. 8,889,668 B2

In the Claims

Column 145,
Claim 1, Lines 46-47, "and an effective amount of an additional active ingredient, $R^1$, $R^2$ denote H, Hal, $CF_3$, $OCF_3$, CN, or $NO_2$," should read
--and an effective amount of an additional active ingredient,
 wherein:
 $R^1$, $R^2$ denote H, Hal, $CF_3$, $OCF_3$, CN, or $NO_2$,--.

Column 146,
Claim 3, Line 37, "one another F," should read --one another are F,--.

Column 146,
Claim 3, Lines 49-55,

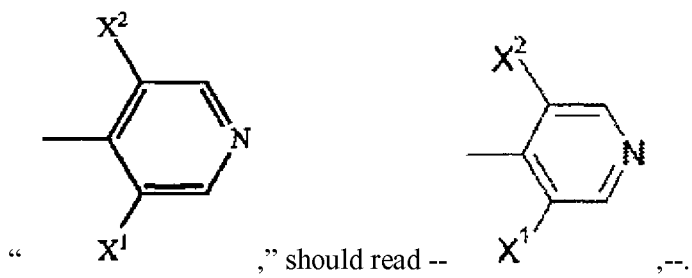

" " ," should read -- ,--.

Column 157,
Claim 6, Lines 38-47,

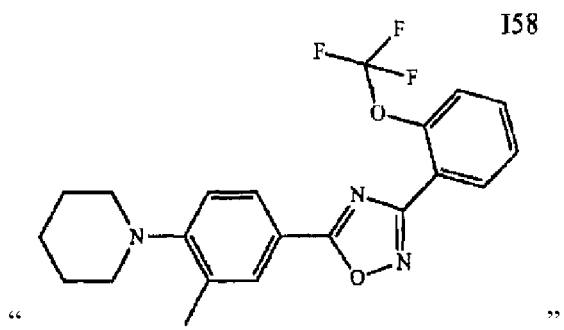

" "
should read

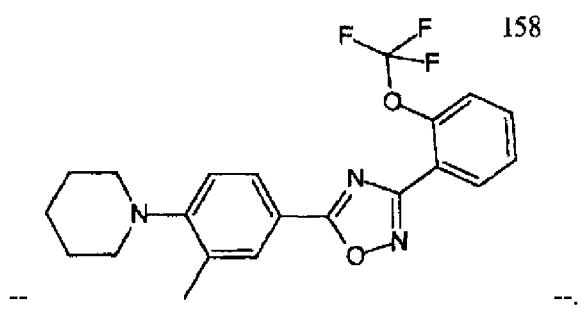

-- --.

Column 161,
Claim 7, Line 21, "or NO₂" should read --or NO$_2$,--.
Claim 7, Line 34, "or –C≡O– groups," should read --or –C≡C– groups,--.
Column 162,
Claim 9, Line 9, "one another F," should read --one another are F,--.
Column 162,
Claim 10, Lines 23-28,
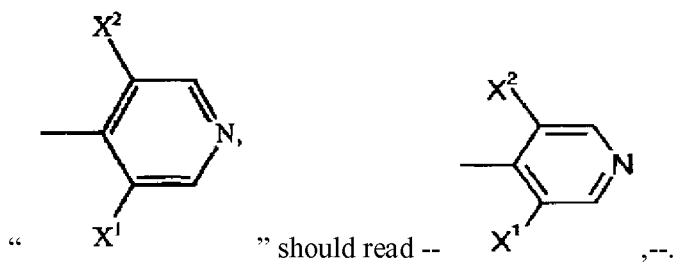 " should read --
Column 173,
Claim 12, Lines 25-35,
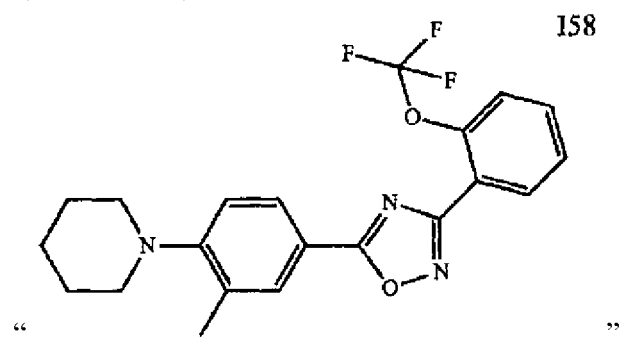
" should read
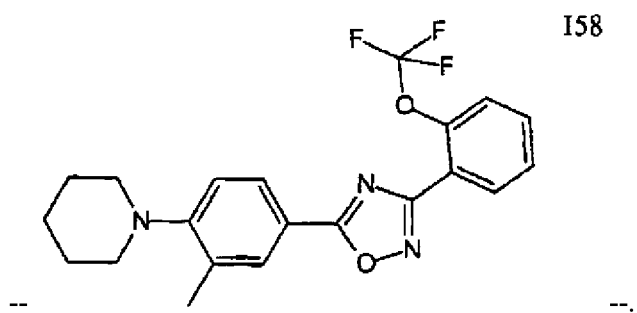
--.

CERTIFICATE OF CORRECTION (continued)
U.S. Pat. No. 8,889,668 B2

Column 175,
Claim 12, Lines 52-60,

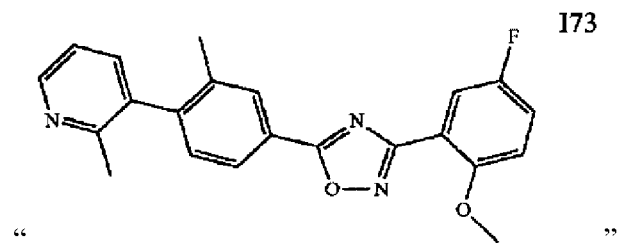

" "

should read

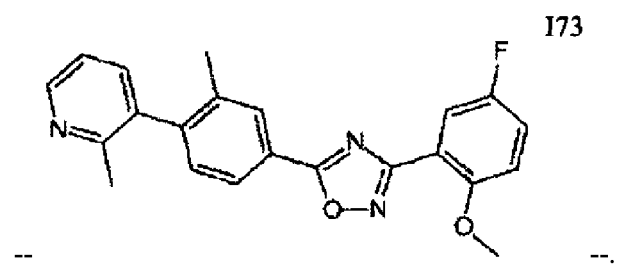

-- --.